US011833188B2

(12) United States Patent
Schiffman et al.

(10) Patent No.: US 11,833,188 B2
(45) Date of Patent: Dec. 5, 2023

(54) METHODS AND COMPOSITIONS FOR PREVENTING OR TREATING CANCER

(71) Applicants: UNIVERSITY OF UTAH RESEARCH FOUNDATION, Salt Lake City, UT (US); TECHNION RESEARCH & DEVELOPMENT FOUNDATION LIMITED, Haifa (IL)

(72) Inventors: Joshua Schiffman, Salt Lake City, UT (US); Avi Schroeder, Haifa (IL); Lisa Abegglen, Salt Lake City, UT (US)

(73) Assignees: UNIVERSITY OF UTAH RESEARCH FOUNDATION, Salt Lake City, UT (US); TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 658 days.

(21) Appl. No.: 16/894,698

(22) Filed: Jun. 5, 2020

(65) Prior Publication Data

US 2020/0368316 A1 Nov. 26, 2020

Related U.S. Application Data

(62) Division of application No. 15/767,099, filed as application No. PCT/US2016/055921 on Oct. 7, 2016, now Pat. No. 10,709,761.

(60) Provisional application No. 62/379,179, filed on Aug. 24, 2016, provisional application No. 62/239,103, filed on Oct. 8, 2015.

(51) Int. Cl.

| | |
|---|---|
| ***A61K 38/17*** | (2006.01) |
| ***A61K 31/7105*** | (2006.01) |
| ***A61K 31/711*** | (2006.01) |
| ***A61K 9/127*** | (2006.01) |
| ***A61K 45/06*** | (2006.01) |
| ***C07K 14/47*** | (2006.01) |
| ***A61K 9/51*** | (2006.01) |
| ***A61K 48/00*** | (2006.01) |
| ***A61P 35/00*** | (2006.01) |

(52) U.S. Cl.

CPC .......... *A61K 38/1758* (2013.01); *A61K 9/127* (2013.01); *A61K 9/51* (2013.01); *A61K 9/5146* (2013.01); *A61K 31/711* (2013.01); *A61K 31/7105* (2013.01); *A61K 45/06* (2013.01); *A61K 48/00* (2013.01); *A61P 35/00* (2018.01); *C07K 14/47* (2013.01); *C07K 14/4746* (2013.01)

(58) Field of Classification Search

CPC .............. A61K 31/7105; A61K 31/711; A61K 38/1758; A61K 45/06; A61K 9/127; A61K 9/51; A61K 9/5146; A61K 48/00; A61K 35/28; A61P 35/00; C07K 14/47; C07K 14/4746; C07K 14/4702; A01K 67/0273; C12N 15/90; C12N 2501/60; C12N 2501/602; C12N 2501/603; C12N 2501/604; C12N 2501/606; C12N 2501/998; C12N 2506/45; C12N 2510/00; C12N 2740/16043; C12N 5/0604; C12N 5/0605; C12N 5/0606; C12N 5/0696

USPC .............................. 435/455, 458; 424/932.21

See application file for complete search history.

(56) References Cited

U.S. PATENT DOCUMENTS

| | | | |
|---|---|---|---|
| 8,507,437 | B2 | 8/2013 | Labhasetwar |
| 2002/0132977 | A1 | 9/2002 | Yuan et al. |
| 2010/0143358 | A1 | 6/2010 | Weisbart |

FOREIGN PATENT DOCUMENTS

| | | | |
|---|---|---|---|
| CN | 104208066 | A | 12/2014 |
| JP | 2001522871 | A | 11/2001 |
| JP | 2011516542 | A | 5/2011 |
| WO | WO 1998/004291 | A1 | 2/1998 |
| WO | 2009/090049 | A1 | 7/2009 |
| WO | 2012/170513 | A3 | 1/2013 |

OTHER PUBLICATIONS

AACR, "Cancer Discovery—Illuminating Cancer Resistance in Elephants," article (Oct. 22, 2015) vol. 5, Iss. 12, 2, p. 1229.

Abegglen et al. "Potential Mechanisms for Cancer Resistance in Elephants and Comparative Cellular Response to DNA Damage in Humans," article (2015) vol. 314, pp. 1850-1860 and Supplementary Content, American Medical Association.

Almazov et al., "Use of p53 for Therapy of Human Cancer," Mol. Biol (Mosk), 2007, 41(6):947-963.

Caulin, Peto's Paradox and the Evolution of Cancer Suppression, 2014, Publicly Accessible Penn Dissertations, 1228, 205 pages.

Garcia-Cao et al. "Super p53' mice exhibit enhanced DNA damage response, are tumor resistant and age normally," article (2002) vol. 21, No. 22, pp. 6225-6235, The EMBO Journal.

Hansen et al., "Antibody-Mediated p53 Protein Therapy Prevents Liver Metastasis In vivo," article, Cancer Research (2007) 67:4, pp. 1769-1774, AACR.

Lafevre-Bernt et al., "Recombinant, refolded tetrameric p53 and gonadotropin-releasing hormone-p53 slow proliferation and induce apoptosis in p53-deficient cancer cells," article (2008) Mol Cancer Ther; 7(6) pp. 1420-1429, AACR.

Lane et al., "p53-based Cancer Therapy," article (2010) pp. 1-24, Cold Sprin Harbor Laboratory Press.

(Continued)

*Primary Examiner* — Janet L Epps-Smith

(74) *Attorney, Agent, or Firm* — Michael Best & Friedrich LLP

(57) ABSTRACT

The present disclosure is directed to methods and compositions for inhibiting a cancer cell using nucleic acid sequences encoding elephant p53 or elephant p53 amino acid sequences.

23 Claims, 14 Drawing Sheets

Specification includes a Sequence Listing.

(56) References Cited

OTHER PUBLICATIONS

Mendrysa et al. "Tumor suppression and normal aging in mice with constitutively high page 53 activity," article, Genes & Development (2006) vol. 20, pp. 16-21, Cold Spring Harbor Laboratory Press.
Nakase et al., "p53 gene therapy of human osteosarcoma using a transferrin-modified cationic liposome," article (2005) Mol Cancer Ther; 4(4) pp. 625-631, AACR.
Sulak et al. "TP53 copy number expansion is associated with the evolution of increased body size and an enhanced DNA damage response in elephants," article (Sep. 19, 2016) vol. 5, pp. 1-30, eLife Sciences.
Sulak et al. "TP53 copy number expansion correlates with the evolution of increased body size and an enhanced DNA damage response in elephants," article (Oct. 6, 2015) 48 pages, bioRxiv, http://dx.doi.org/10.1101/028522.
Suzuki et al., "Recent Advances in p53 Research and Cancer Treatment," article ID 978312, 7 pages (2011) Hindawi Publishing Corporation Journal of Biomedicine and Biotechnology.
Vinyals et al., "Failure of wild-type p53 gene therapy in human cancer cells expressing a mutant p53 protein," article, Gene Therapy, (1999) 6, pp. 22-33, Stockton Press.
PCT/US2016/055921 ISR/WO International Search Report and Written Opinion of the International Searching Authority dated Jan. 30, 2017 (9 pages).
PCT/US2016/055921 IPRP International Preliminary Report on Patentability dated Apr. 19, 2018 (6 pages).
Australian Patent Office Examination Report No. 1 for Application No. 2016335701 dated Dec. 12, 2018 (3 pages).
Canadian Patent Office Action for Application No. 3,001,054 dated Jan. 8, 2019 (5 pages).
Japanese Patent Office Action for Application No. 2018-538063 dated Jan. 29, 2019 (14 pages, English translation included).
European Patent Office Supplementary Search Report for Application No. 16854394.0 dated Mar. 14, 2019 (12 pages).
EBI Accession No. KF715855 (2015).
EBI Accession No. KF715856 (2015).
EBI Accession No. KF715857 (2015).
EBI Accession No. KF715858 (2015).
EBI Accession No. KF715859 (2015).
EBI Accession No. KF715860 (2015).
EBI Accession No. KF715861 (2015).
EBI Accession No. KF715862 (2015).
EBI Accession No. KF715863 (2015).
EBI Accession No. KF715864 (2015).
EBI Accession No. KF715865 (2015).
EBI Accession No. KF715866 (2015).
EBI Accession No. KF715867 (2015).
EBI Accession No. KF715868 (2015).
EBI Accession No. KF715869 (2015).
EBI Accession No. KF715870 (2015).
EBI Accession No. KF715871 (2015).
EBI Accession No. KF715872 (2015).
Israeli Patent Office Action for Application No. 258512 dated Apr. 3, 2019 (3 pages, English translation only).
Russian Patent Office Action for Application No. 2018116896 dated Apr. 12, 2019 (8 pages, English translation included).
Brazilian Patent Office Action for Application No. 112018007173-0 dated Sep. 1, 2020 (12 pages, partial English translation included).
Canadian Patent Office Action for Application No. 3,001,054 dated Sep. 9, 2020 (6 pages).
Chappell et al., "p53 expression controls prostate cancer sensitivity to chemotherapy and the MDM2 inhibitor Nutlin-3," Cell Cycle, 2012, 11(24): 4579-4588.
Chinese Patent Office Action for Application No. 201680066779.4 dated Mar. 9, 2022 (10 pages including English translation).
Intellectual Property Office India Examination Report for Application No. 201817016788 dated Mar. 24, 2022 (9 pages).
Korean Patent Office Notice of Preliminary Rejection for Application No. 10-2018-7012840 dated Feb. 24, 2021 (7 pages including English translation).
Canadian Patent Office Action for Appplication No. 3,001,054 dated Mar. 30, 2021 (3 pages).
Chinese Patent Office Second Office Action for Application No. 201680066779.4 dated May 10, 2021 (21 pages Including English translation).
Mexican Patent Office Action for Application No. MX/a/2018/004187 dated Apr. 9, 2021 (5 pages including brief English summary).
Korean Patent Office Action for Application No. 10-2018-7012840 dated Jul. 14, 2020 (17 pages, English translation Included).
Chinese Patent Office Action for Application No. 201680066779.4 dated Jul. 24, 2020 (21 pages, English translation Included).
China National Intellectual Property Administration Third Office Action for Application No. 201680066779.4 dated Nov. 9, 2021 (10 pages including English translation).

1.5% agarose gel

10% polyacrylamide gel

FIG. 5A
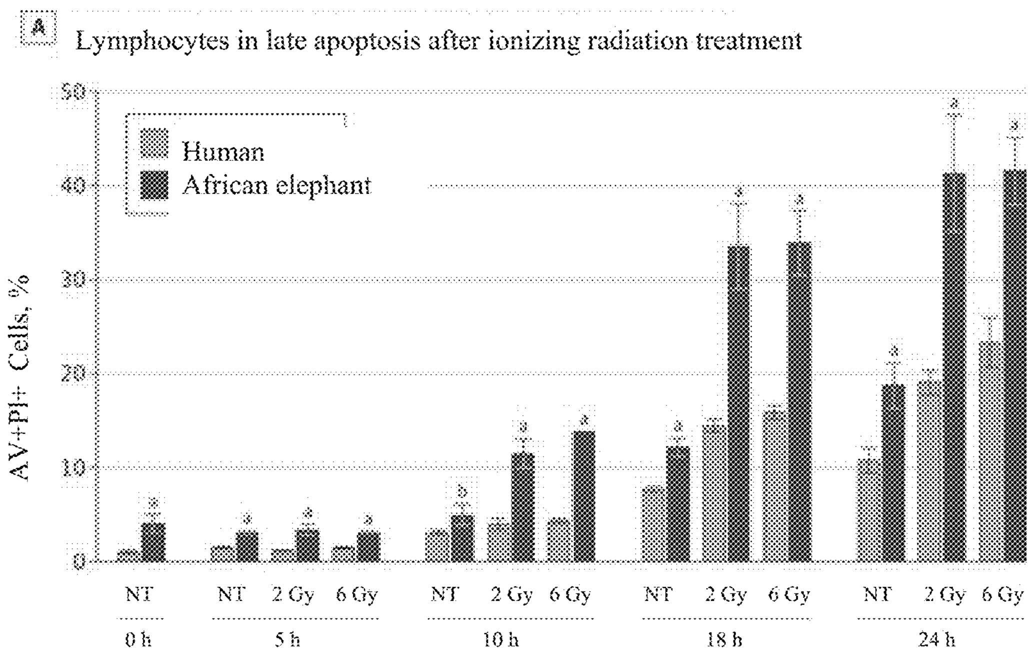
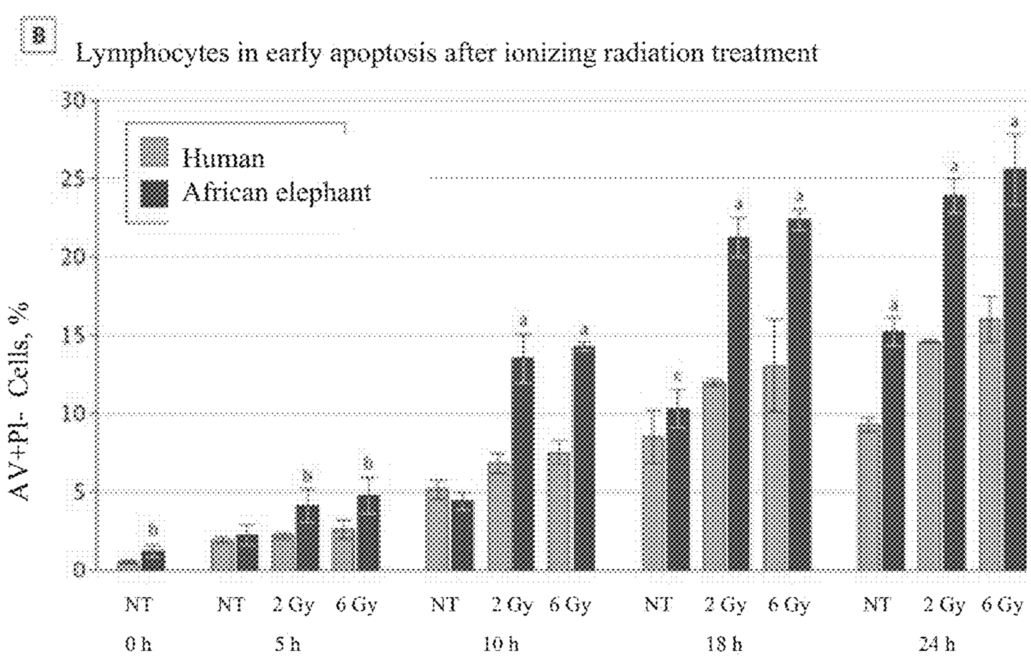
FIG. 5B

FIG. 6A
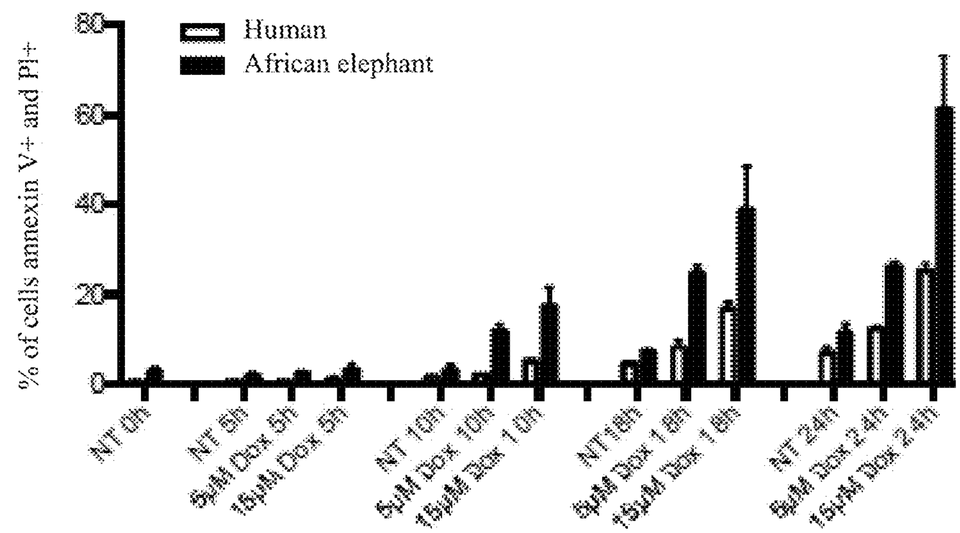
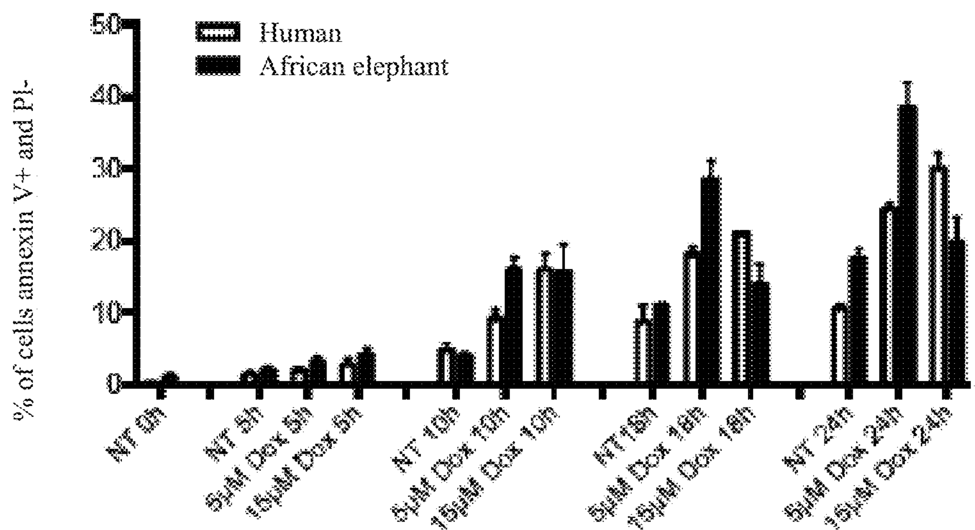
FIG. 6B

FIG. 10A
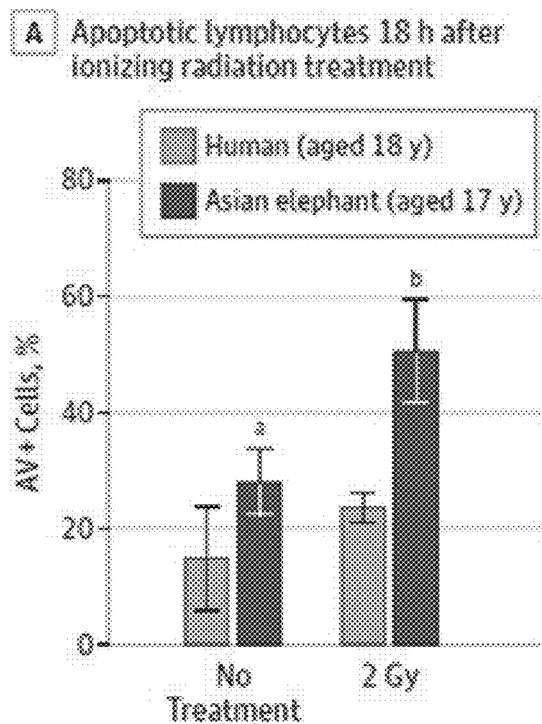
FIG. 10B
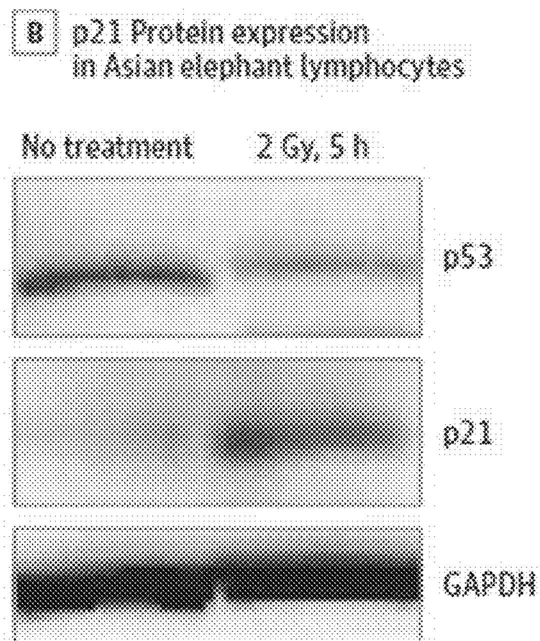
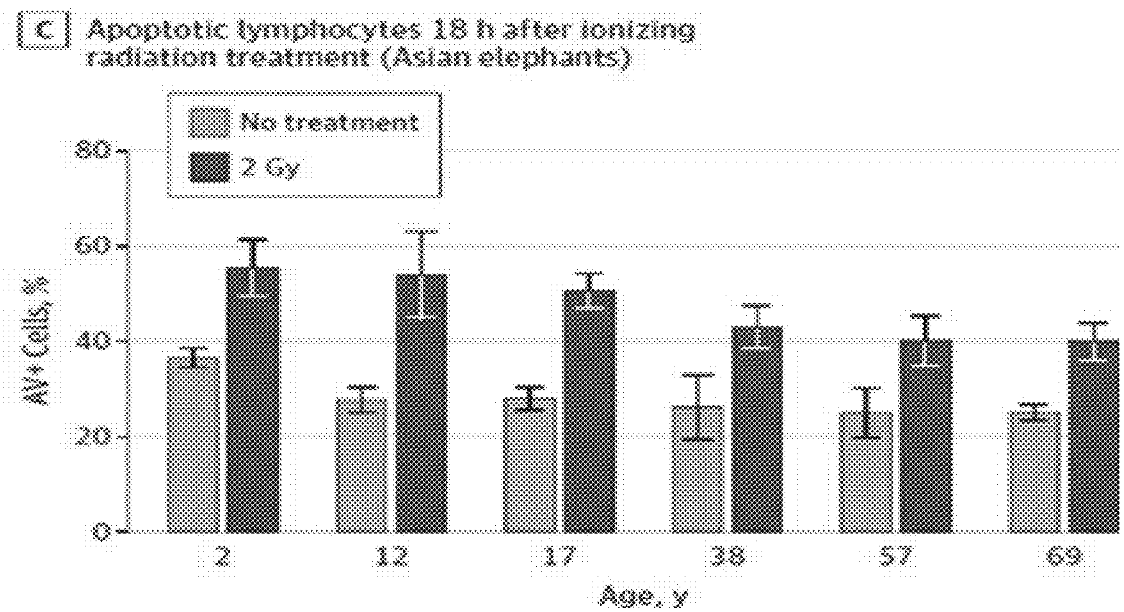
FIG. 10C

FIG. 11A
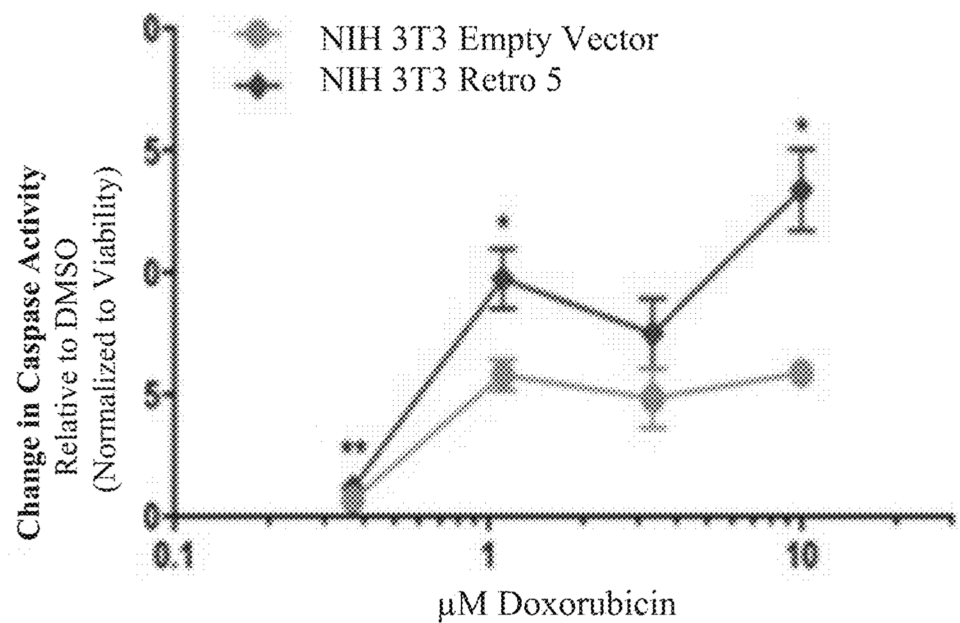
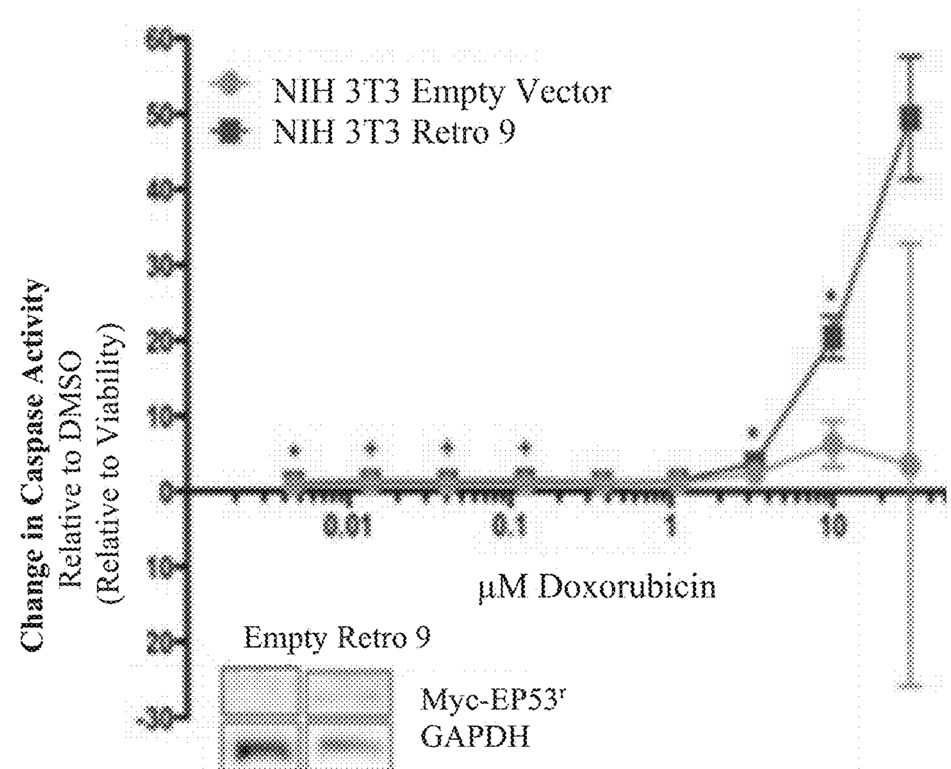
FIG. 11B

FIG. 12A
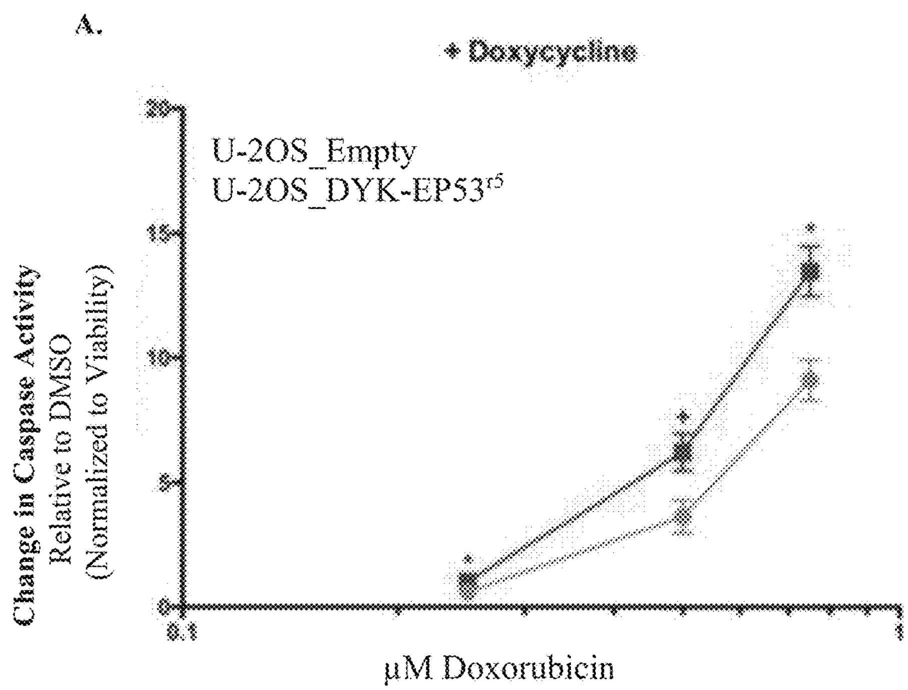
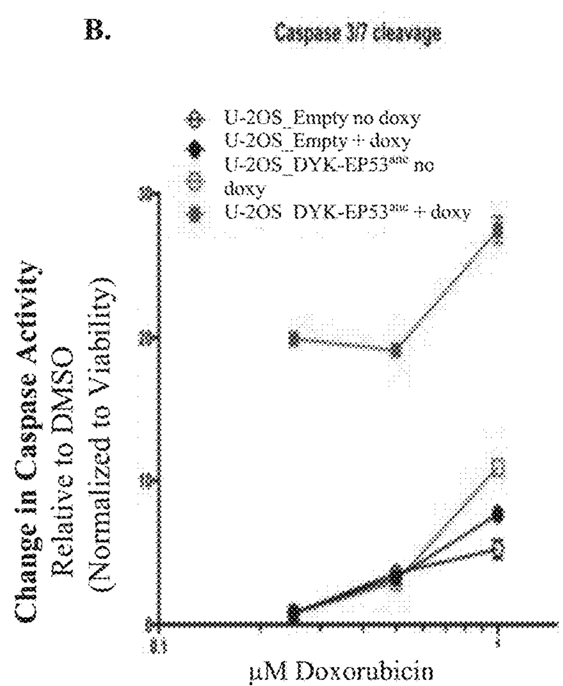
FIG. 12B
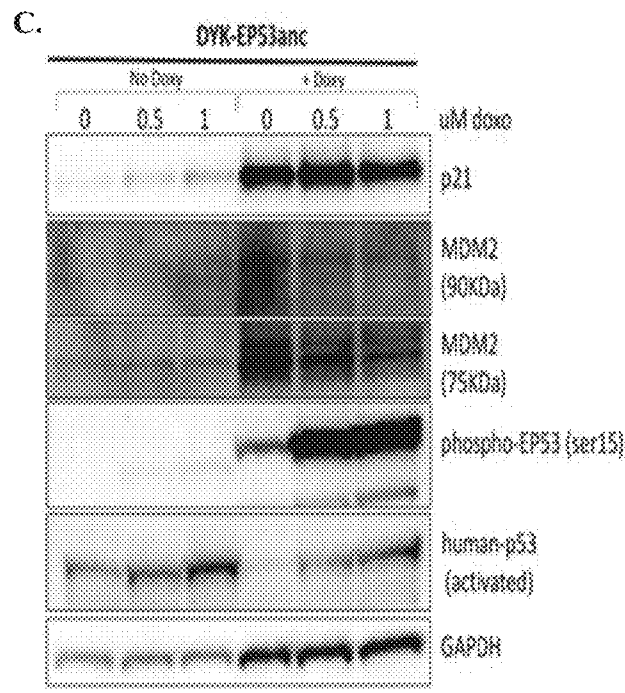
FIG. 12C

FIG. 14A
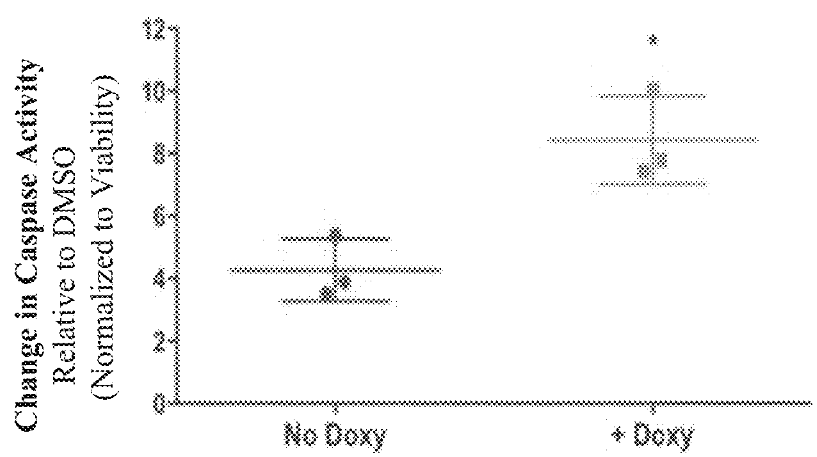
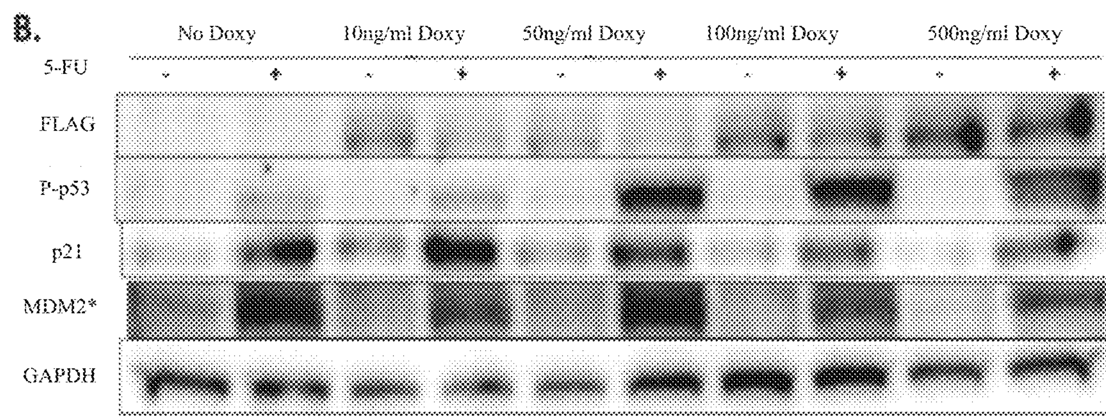
FIG. 14B

METHODS AND COMPOSITIONS FOR PREVENTING OR TREATING CANCER

CROSS-REFERENCE TO RELATED APPLICATION(S)

This is a divisional of U.S. patent application Ser. No. 15/767,099, filed on Apr. 9, 2018, which is a U.S. national stage entry of International Patent Application No. PCT/US2016/055921, filed on Oct. 7, 2016, which claims priority to U.S. Provisional Patent Application No. 62/239,103, filed on Oct. 8, 2015, and U.S. Provisional Patent Application No. 62/379,179, filed on Aug. 24, 2016, the entire contents of all of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 184,774 bytes ASCII (Text) file named "026389-9173_ST25.txt," created on Oct. 6, 2016.

BACKGROUND OF THE INVENTION

Multicellular organisms have intrinsic defenses to protect against the development of mutations and cancer. One such defense mechanism is the signaling pathways regulated by tumor protein p53 (encoded by the gene TP53), which is a critical suppressor of cancer. Referred to as the "guardian of the genome," p53 is able to halt cell division when DNA damage is detected and either initiate correction of the mutation, or trigger apoptosis if the damage is irreparable (Blagosklonny. *Int J Cancer,* 98: 161-166(2002)). Humans contain one copy (two alleles) of TP53, and both functioning alleles are crucial to prevent cancer development. The absence of even one functional allele leads to Li-Fraumeni Syndrome (LFS), a cancer predisposition in which patients have a 90% chance of developing cancer during their lifetime (McBride et al. *Nat Rev Clin Oncol;* 11(5): 260-271 (2014)). Inactivation of p53 also can lead to cancer (Lane, D P. *Nature;* 358(6381): 15-16 (2014); Hanahan et al. *Cell;* 144(5): 646-674 (2011)), and in humans p53 function naturally decreases with age (Feng et al., *PNAS;* 104(42): 16633-16638 (2007)), leaving half of all men and a third of all women susceptible to developing cancer during their lifetime (*American Cancer Society; Cancer Facts & Figures* (2015)). Mutations of p53 have been identified in numerous human cancers (Hollstein et al., *Science;* 253(5015): 49-53 (1991)).

Researchers have naturally focused on combating cancer by utilizing the protective properties of p53. For example, retrovirus- and adenovirus-mediated TP53-gene therapies have been developed to deliver human p53 to cancer cells (Cai et al. *Hum Gene Ther:* 4: 617-624 (1993); Brandt et al. *Am J Epidemiol;* 90: 484-500 (1969)), and the accumulation of p53 can be induced by disrupting its negative regulation by mouse double minute 2 (MDM2) (Vassilev et al. *Science;* 3i03: 844-848 (2004)). However these therapies have primarily focused on restoring the activity of wild type p53 in humans, or eliminating cancer cells with mutant p53.

Given that each cell division can potentially introduce a new genetic mutation, it was originally suspected that in larger organisms (which naturally require a greater number of cell divisions) there would be an increase in the number of mutated cells (Tomasetti et al., *Science;* 347(6217): 78-81 (2015)). If all mammalian cells are equally susceptible to oncogenic mutations, then cancer risk should increase with body size (number of cells) and species lifespan (number of cell divisions). However this theory was disproved over 35 years ago, as cancer incidence across animals does not appear to increase for larger body size and lifespan (Caulin et al., *Trends Ecol Evolut;* 26(4): 175-182 (2011); Peto et al., *Br J Cancer;* 32(4): 411-426 (1975)). The cellular and molecular mechanisms of this resistance to cancer in larger animals are not clearly understood, however a recent study has shown that elephants are especially resistant to developing cancer (Abegglen et al. *JAMA;* 314(17): 1850-60 (2015)). It was also discovered that elephants carry extra copies of the TP53 gene. Follow up studies showed that elephant p53 (EP53) is especially effective at killing cancer cells, even when the cancer cells already contained human p53.

There remains a need for compositions and methods to more effectively restore p53 function to cancerous cells. The invention provides such compositions and methods.

BRIEF SUMMARY OF THE INVENTION

The present disclosure provides a method of inhibiting cancer which comprises contacting a cancer cell with (a) one or more nucleic acid sequences each encoding an elephant p53 protein, or (b) one or more elephant p53 proteins, whereby the cancer is inhibited.

The present disclosure also provides a composition comprising a pharmaceutically acceptable carrier and (a) one or more nucleic acid sequences each encoding an elephant p53 protein or (b) one or more elephant p53 proteins.

BRIEF DESCRIPTION OF THE DRAWINGS

FIG. 5A is a bar graph showing the percentage of elephant peripheral blood lymphocytes compared to human peripheral blood lymphocytes undergoing late apoptosis in response to 2 Gy and 6 Gy ionizing radiation. FIG. 5B is a bar graph showing the percentage of elephant peripheral blood lymphocytes compared to human peripheral blood lymphocytes undergoing early apoptosis in response to 2 Gy and 6 Gy ionizing radiation.

FIG. 6A is a bar graph showing that lymphocytes from an African elephant exhibit greater levels of late apoptosis after exposure to doxorubicin. FIG. 6B is a bar graph showing that lymphocytes from an African elephant exhibit greater levels of early apoptosis after exposure to doxorubicin.

FIG. 10A is a bar graph showing the percentage of apoptotic cells in lymphocytes from a human and an Asian elephant, 18 hours after 2 Gy ionizing radiation treatment. FIG. 10B is an image of a western blot showing p21 protein expression in Asian elephant lymphocytes 5 hours after 2 Gy ionizing radiation. FIG. 10C is a bar graph showing the percentage of apoptotic lymphocytes in Asian elephants, sorted by age groups, 18 hours after ionizing radiation treatment.

FIG. 11A is a line graph showing an increase is caspase activity in NIH 3T3 cells transfected with $EP53^{r5}$ following treatment with doxorubicin. FIG. 11B is a line graph showing an increase is caspase activity in NIH 3T3 cells transfected with $EP53^{r9}$ following treatment with doxorubicin.

FIG. 12A is a line graph showing an increase in caspase activity in U-2OS cells transfected with $EP53^{r6}$ following treatment with doxorubicin. FIG. 12B is a line graph showing an increase in caspase activity in U-2OS cells induced with $EP53^{anc}$ following treatment with doxorubicin. FIG. 12C is an image of a western blot showing that U-2OS cells induced with $EP53^{anc}$ and treated with doxorubicin to induce DNA damage exhibit an increase in p53 target genes, p21 and MDM2.

FIG. 14A is a dot plot showing that HCT 116 cells transfected with $EP53^{r9}$ exhibit an increase in caspase activity following treatment with doxorubicin. FIG. 14B is a western blot showing that HCT 116 cells transfected with $EP53^{r9}$ exhibit an increase in $EP53^{r9}$ expression that correlates with increasing doses of doxycycline.

DETAILED DESCRIPTION OF THE INVENTION

Figure 1:
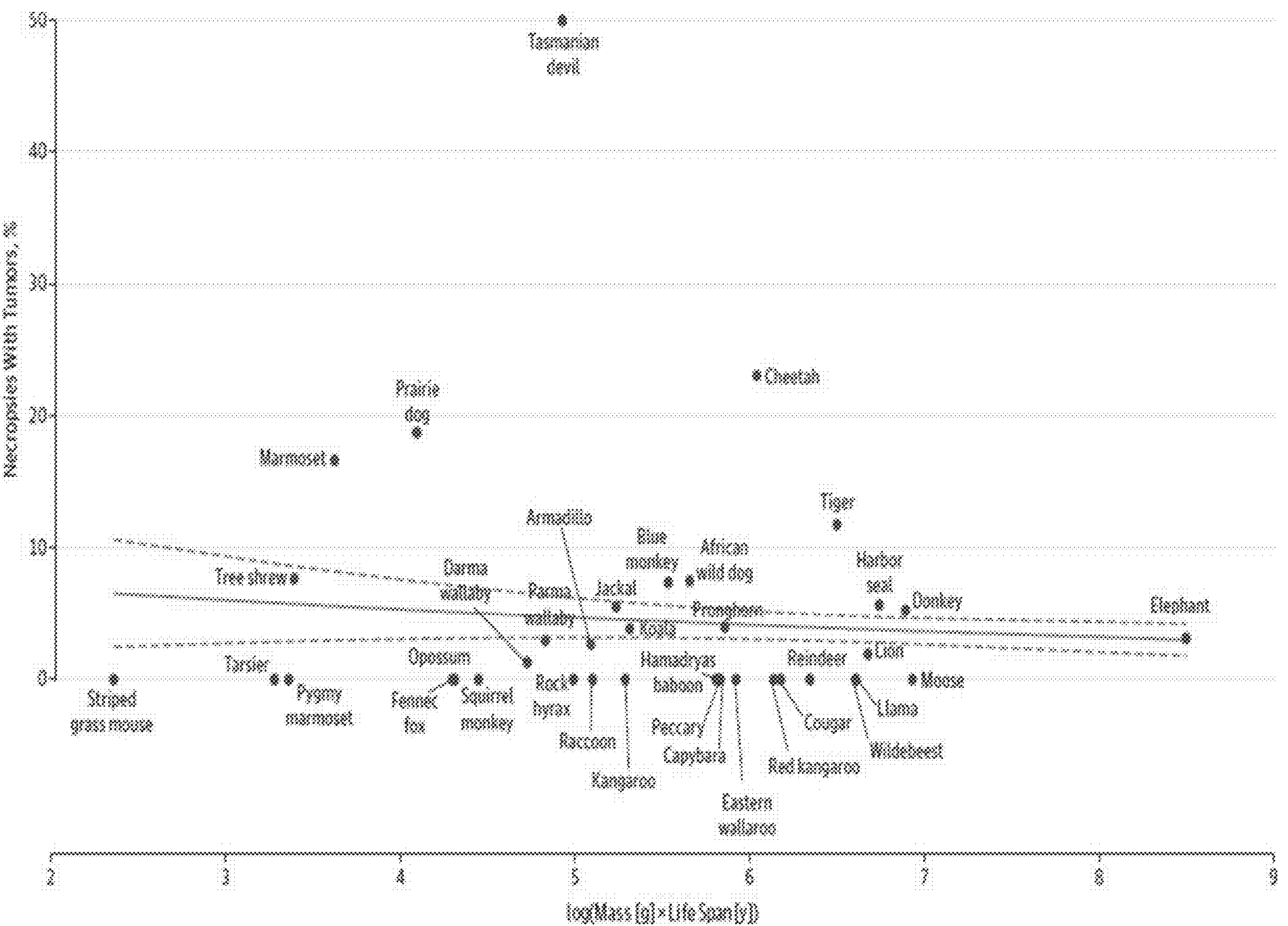
FIG. 1 is a plot of the log(mass×life span) of 33 different mammalian species relative to the percentage of necropsies performed on each species that exhibited tumors.

The present disclosure is predicated, at least in part, on the discovery that African elephants are more resistant to cancer than humans. Cancer mortality occurs in about 11% to 25% of humans, while cancer occurs in about 3% to 6% of elephants. This increased resistance to cancer may partially be explained by the increase in genetic copies of the TP53 gene in elephants, which encodes the p53 protein. While humans only have one copy of TP53 (two alleles), elephants have at least 20 copies (40 alleles) of the elephant p53 (EP53) gene. In cell culture studies, it was found that elephant lymphocytes were more likely to execute apoptosis in response to DNA damage from ionizing radiation exposure, suggesting a lower threshold for DNA damage before elephant p53-mediated apoptosis is triggered. Elephant p53 appears to be more effective than human p53 at detecting DNA damage and removing mutated cells from an organism. The use of elephant p53 has not previously been explored as a mechanism for targeting human cancers.

Elephant p53 Sequences

The present disclosure provides a method of inhibiting cancer, which comprises contacting a cancer cell with one or more nucleic acid sequences each encoding an elephant p53 protein, or one or more elephant p53 proteins.

Nucleic acids can be single stranded or double stranded, or can contain portions of both double stranded and single stranded sequences. The nucleic acid can be DNA, and contain deoxyribonucleotides, or RNA, and contain ribonucleotides. Nucleic acids can be obtained by chemical synthesis methods or by recombinant methods. A particular nucleic acid sequence can encompass conservatively modified variants thereof (e.g., codon substitutions), alleles, orthologs, single nucleotide polymorphisms (SNPs), and complementary sequences as well as the sequence explicitly indicated.

A cancer cell may be contacted with any suitable nucleic acid sequence encoding an elephant p53 protein in any suitable combination. For example, in some embodiments, the cancer cell may be contacted with one nucleic acid sequence encoding an elephant p53 protein. In other embodiments, the cancer cell is contacted with multiple nucleic acid sequences, each encoding an elephant p53 protein. As elephants comprise at least 20 copies of the TP53 gene, the cancer cell may be contacted with 2 to 25 nucleic acid sequences (e.g., 2, 3, 4, 5, 6, 7, 8, 9, 10, 11, 12, 13, 14, 15, 16, 17, 18, 19, 20, 21, 22, 23, 24, or 25 nucleic acid sequences) each encoding an elephant p53 protein. In one embodiment, the one or more nucleic acid sequences encoding an elephant p53 protein is a retrogene. As used herein, the term "retrogene" refers to an RNA transcribed from a DNA gene copied back into the genome by reverse transcription. A retrogene may lack introns. The cancer cell may be contacted with multiple nucleic acid sequences each of which comprise the same retrogene, multiple different retrogenes, or combinations thereof. In addition or alternatively, the nucleic acid sequence encoding an elephant p53 protein may be an ancestral gene. As used herein, the term "ancestral gene" refers to a common gene from which a family of genes descends. An ancestral gene may be derived from ancestral gene resurrection or ancestral gene restoration, wherein the ancestral protein is inferred by means of phylogenetic methods, and a DNA molecule coding for that protein is synthesized (Chang et al., *Integr Comp Biol;* 43(4): 500-507 (2003)). The cancer cell may be contacted with multiple nucleic acid sequences each of which comprise the same ancestral gene, multiple different ancestral genes, or combinations thereof. In other embodiments, the cancer cell may be contacted with a combination of one or more p53-encoding retrogenes and one or more p53-encoding ancestral genes.

Examples of nucleic acid sequences of retrogenes encoding elephant p53 proteins include, but are not limited to, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, and SEQ ID NO: 76. An example of a nucleic acid sequence of an ancestral gene encoding an elephant p53 protein includes, but is not limited to, SEQ ID NO: 2.

For delivery to cells (e.g., cancer cells), the one or more nucleic acid sequences may be incorporated into a gene transfer vector. A "gene transfer vector" or "vector" is any molecule or composition that has the ability to carry genetic materials (e.g., a nucleic acid sequence), into a suitable host cell where the synthesis of the encoded protein takes place. Suitable vectors include, but are not limited to, plasmids, viral vectors, liposomes, lipids, polymers, inorganic nanoparticles, or chimeric vectors comprising any combination of the foregoing (e.g., a plasmid-lipid complex or a plasmid-polymer complex). Suitable viral vectors include, for example, retroviral vectors, herpes simplex virus (HSV)-based vectors, parvovirus-based vectors, sendai virus (SeV)-based vectors, adeno-associated virus (AAV)-based vectors, AAV-adenoviral chimeric vectors, and adenovirus-based vectors, and can be prepared using standard recombinant DNA techniques described in, for example, Sambrook et al., *Molecular Cloning, a Laboratory Manual,* $4^{th}$ edition, Cold Spring Harbor Press, Cold Spring Harbor, N.Y. (2012), and Ausubel et al., *Current Protocols in Molecular Biology*, Greene Publishing Associates and John Wiley & Sons, New York, N.Y. (2016). Suitable polymers, lipids, and inorganic nanoparticles are described in, for example, Peer et al., *Nature Nanotechnology,* 2:751-760 (2007), and Boussif et al., *Proceedings of the National Academy of Sciences of the United States of America,* 92: 7297-7301 (1995)).

In other embodiments, the cancer cell may be contacted with one or more elephant p53 proteins. A cancer cell may be contacted with any suitable elephant p53 protein in any suitable combination. As discussed above, because elephants comprise at least 20 copies of the TP53 gene, the cancer cell may be contacted with 2 to 25 p53 proteins (e.g., 2, 3, 4, 5, 6, 7, 8, 9, 10, 11, 12, 13, 14, 15, 16, 17, 18, 19, 20, 21, 22, 23, 24, or 25 proteins). The one or more elephant p53 proteins may be encoded by one or more retrogenes, such as those described herein. For example, the cancer cell may be contacted with multiple proteins, each of which is encoded by the same retrogene, multiple different retrogenes, or combinations thereof. In addition or alternatively, the one or more elephant p53 proteins may be encoded by an ancestral gene, such as those described herein. The cancer cell may be contacted with multiple p53 proteins, each of which is encoded by the same ancestral gene, multiple different ancestral genes, or combinations thereof. In other embodiments, the cancer cell may be contacted with a combination of one or more retrogene-encoded p53 proteins and one or more ancestral gene-encoded p53 proteins.

Examples of retrogene-encoded elephant p53 amino acid sequences, but are not limited to, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, and SEQ ID NO: 77. An example of an ancestral gene-encoded elephant p53 amino acid sequence includes, but is not limited to SEQ ID NO: 3.

Compositions

In certain embodiments, the one or more elephant TP53 nucleic acid sequences encoding the one or more elephant p53 proteins are in the form of a composition. Thus, the present disclosure also provides a composition comprising a pharmaceutically acceptable carrier and (a) one or more nucleic acid sequences each encoding an elephant p53 protein or (b) one or more elephant p53 proteins. Any suitable pharmaceutically-acceptable carrier may be used in the context of the present disclosure, and such carriers are well known in the art. The choice of carrier will be determined, in part, by the particular site to which the composition is to be administered and the particular method used to administer the composition. Exemplary formulations for the composition include, but are not limited to, oral, injectable, and aerosol formulations.

Formulations suitable for oral administration may comprise (a) liquid solutions, such as an effective amount of the one or more nucleic acid sequences or proteins dissolved in diluents, such as water, saline, or a beverage, (b) capsules, sachets, or tablets, each containing a predetermined amount of the one or more nucleic acid sequences or proteins, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the one or more nucleic acid sequences or proteins in a flavor, usually sucrose and acacia or tragacanth, as well as pastilles comprising the active ingredient in an inert base, such as gelatin and glycerin, or sucrose and acacia, emulsions, gels, and the like containing, in addition to the one or more nucleic acid sequences or proteins, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for aerosol administration comprising the one or more nucleic acid sequences or proteins, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for topical administration may include creams, lotions, gels, ointments, or the like. Other suitable formulations are possible, for example, suppositories can be prepared by use of a variety of bases such as emulsifying bases or water-soluble bases. Formulations suitable for vaginal administration can be presented as pessaries, tampons, creams, gels, pastes, foams, or spray formulas containing, in addition to the one or more nucleic acid sequences or proteins, such carriers as are known in the art to be appropriate.

In an embodiment, suitable formulations of the composition may comprise a phase transition temperature that is equal to or lower than the thermal stability of the protein. For example, a protein with a thermal stability of 25° C. may be formulated with a phospholipid comprising a melting temperature of 23° C. (e.g., 1,2-Dimyristoyl-sn-glycero-3-phosphocholine (DMPC)). Suitable phospholipids are well known in the art.

In one aspect of the above method, the composition comprises a liposome. The term "liposome" as used herein refers to an artificially prepared vesicle composed of a lipid bilayer. The term "lipid bilayer" as used herein refers to a membrane made of two layers of lipid molecules. The lipid bilayer may have a similar thickness to that of a naturally existing bilayer, such as a cell membrane, a nuclear membrane, and a virus envelope. For example, the lipid bilayer may have a thickness of about 10 nm or less, for example, in a range of about 1 nm to about 9 nm, about 2 nm to about 8 nm, about 2 nm to about 6 nm, about 2 nm to about 4 nm, or about 2.5 nm to about 3.5 nm. The lipid bilayer is a barrier that retains nucleic acids, proteins, ions, and other molecules while also preventing them from diffusing into undesirable areas.

The "lipid molecules" forming the lipid bilayer may comprise a molecule including a hydrophilic head and a hydrophobic tail. The lipid molecule may comprise from about 14 to about 50 carbon atoms. Examples of the lipid molecules which may form a lipid bilayer include phospholipids, lipids conjugated to polyethylene glycol (PEG), cholesterol, or any combination thereof. A liposome may be classified as a unilamellar vesicle or a multilamellar vesicle. A unilamellar vesicle, as defined herein, is a single bilayer of an amphiphilic lipid or a mixture of such lipids, containing aqueous solution inside the chamber. A multilamellar vesicle consists of many concentric amphiphilic lipid bilayers.

In another aspect of the above method, the liposome may be a micelle, a bicelle, or a lipid nanodisc. As used herein, "micelle" refers to an aggregate of surfactant molecules comprising a hydrophobic interior. In some embodiments, the micelle may be comprised within the hydrophilic interior space of a liposome. A "bicelle" is a disc-shaped micelle. A micelle or a bicelle may comprise a hydrophobic nucleic acid, protein, ion, or other molecule. The term "nanodisc," as used herein, refers to at least one phospholipid bilayer, wherein the hydrophobic edge is stabilized by at least one amphipathic protein.

In some embodiments, the one or more nucleic acid sequences or one or more elephant p53 amino acid sequences are encapsulated within a liposome.

In another embodiment, the one or more nucleic acid sequences or one or more elephant p53 proteins may be encapsulated within a nanoparticle. A "nanoparticle," as defined herein, is a three-dimensional particle having at least one dimension that is less than 100 nm. In the context of the present disclosure, a nanoparticle may comprise a hydrophobic core and a hydrophilic layer surrounding the core. A nanoparticle may also comprise an external surface decorated with one or more moieties. As used herein, a "moiety" is a part or functional group of a molecule. The one or more moieties may be embedded in the nanoparticle core, contained within the core, attached to a molecule that forms at least a portion of the core, attached to a molecule attached to the core, or directly attached to the core. A moiety may be chosen so as to reduce the interaction of the nanoparticle with the reticuloendothelial system. Such moieties include, for example, polyethylene glycol (PEG).

In an embodiment, the one or more moieties may comprise a targeting moiety. As used herein, a "targeting moiety" directs a nanoparticle to a specific cell type, e.g., a cancer cell. The targeting moieties preferably extend outwardly from the core so that they are available for interaction with cellular components or so that they affect the surface properties of the nanoparticle. In an embodiment, the targeting moieties may be tethered to the core or components that interact with the core. The targeting moiety may comprise a small molecule carrier, such as, a cholesterol, a sugar, or insulin, to facilitate metabolic uptake of the nanoparticle. The targeting moiety may additionally comprise an antibody or a ligand that is specific for a molecule, e.g., a receptor, on the outside of the targeted cell. The one or more targeting moieties may target the nanoparticle to a specific cellular organelle, such that the nanoparticle accumulates in a specific cellular organelle, relative to other organelles or cytoplasm, at a greater concentration than a substantially similar non-targeted nanoparticle. A substantially similar non-targeted nanoparticle includes the same components in substantially the same relative concentration (e.g., within about 5%) as the targeted nanoparticle, but lacks a targeting moiety. Cellular organelles that may be targeted by the nanoparticle include, for example, the cell membrane, nucleus, nucleolus, mitochondria, golgi apparatus, golgi vesicle, rough endoplasmic reticulum, smooth endoplasmic reticulum, lysosome, peroxisome, cytoplasm, cytosol, vacuole, and secretory vesicles.

In another embodiment, the targeting moiety, e.g., a targeting peptide, cholesterol, sugar, or polyethylene glycol, may be conjugated to a variant of an elephant p53 protein to facilitate targeting a specific cell type, and/or to increase the half-life of the protein.

The nanoparticle may also comprise one or more therapeutic agents (e.g., the elephant TP53-encoding nucleic acids or p53 proteins described herein). In an embodiment, the therapeutic agent may comprise a short peptide segment of an elephant p53 protein, e.g. a peptide 13-mer in length. The therapeutic agent may be released into a specific cell type following cellular uptake of the nanoparticle, e.g., fusion of the nanoparticle with a specific cell type. In another embodiment, the therapeutic agent may be released outside of a specific cell type, and be taken up by a cellular mechanism, such as, macropinocytosis. The therapeutic agents may be contained within the nanoparticle core and released from the core at a desired rate. In some embodiments, the core may be biodegradable, releasing the one or more therapeutic agents as the core is degraded or eroded.

The composition may further comprise one or more additional agents or additives that inhibit cancer or enhance the activity of the elephant p53 nucleic acids and proteins described herein. The agent may optionally improve the efficacy of the therapeutic agent, and/or prevent inactivation, denaturation, or degradation of the therapeutic agent. For example, the composition may further comprise a small molecule chemotherapeutic, a monoclonal antibody, or an imaging agent (e.g., contrast agent, a sugar, an iron complex, or gadolinium (Gd)).

The above-described composition, one or more elephant p53-encoding nucleic acid sequences, or one or more elephant p53 proteins can be provided in a kit, i.e., a packaged combination of reagents in predetermined amounts with instructions for performing a diagnostic assay or therapeutic method. The kit may include additives, such as stabilizers, buffers, and the like, as well as instructions for use of the kit. The relative amounts of the various reagents can be varied to provide for concentrations in solution of the reagents which substantially optimize the sensitivity of the assay.

Method of Inhibiting Cancer

The present disclosure provides a method of inhibiting cancer using the one or more nucleic acid sequences each encoding an elephant p53 protein described herein, the one or more elephant p53 proteins described herein, or compositions comprising the one or more elephant nucleic acid sequences proteins described herein. The term "inhibiting cancer," as used herein, refers to preventing, suppressing, blocking, or slowing the growth, proliferation and/or metastasis of one or more cancer cells. In some embodiments, for example, the method described herein may promote inhibition of cancer cell proliferation, inhibition of cancer cell vascularization, eradication of cancer cells, and/or a reduction in the size of at least one cancerous tumor, such that a human is treated for cancer.

The method described herein may be used to inhibit the growth, proliferation, and/or metastasis of any cancer cell type known in the art, such as, for example, bladder cancer, bone cancer, brain cancer, breast cancer, cervical cancer, colon cancer, esophageal cancer, gall bladder cancer, head and neck cancer (e.g., cancer of the oral cavity, pharynx, larynx, salivary gland, and paranasal sinuses and nasal cavity), leukemia, liver cancer, lung cancer, lymphoma, melanoma, ovarian cancer, pancreatic cancer, prostate cancer, rectal cancer, renal cell carcinoma, stomach (gastric) cancer, small intestine cancer, and thyroid cancer. The cancer cell may originate from a subject as defined herein, which desirably is a mammal, and preferably is a human (e.g., a human comprising a cancer). The cancer cell may also originate from non-human animals, for example, all mammalian and non-mammalian vertebrates (such as, but not limited to, non-human primates, sheep, dogs, cats, dogs, cows, pigs, horses, rodents, poultry, amphibians, and reptiles).

In some embodiments, the cancer cell may be a population of cancer cells, such as, for example, a primary cancer or tumor, a metastatic cancer or tumor, or a cancer tumor regrowth. In one embodiment, the cancer cell or population of cancer cells comprises a defective (e.g., mutant) TP53 gene or protein, such as a TP53 gene comprising a deletion, point mutation, insertion, substitution, or genetic rearrangement of a TP53 gene which results in altered TP53 expression (e.g., over- or under-expression), expression of a p53 protein with abnormal function, or abrogation of p53 protein expression entirely. The defective gene or deleted gene may be present in one allele (heterozygous altered), or two alleles (homozygous altered). The cancer cell or population of cancer cells may comprise a normal TP53 gene or protein, with other genomic alterations throughout the cancer cell genome.

In accordance with the methods described herein, the cancer cell may be ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context.

In embodiments where the methods are conducted in vitro or ex vivo, the cancer cell may be a tumor or cancer cell line. Tumor and cancer cell lines may be obtained commercially or from public sources. Examples of commercially or publically available sources from which tumor or cancer cell lines can be purchased include, but are not limited to, the American Type Culture Collection (ATCC), Manassus, Va.; Deutsche Sammlung von Mikroorganismen and Zellkulturen GmbH (DSMZ) Braunschweig, Germany; Cell Line Service (CLS), Germany; and European Collection of Cell Cultures (ECACC), Salisbury, Great Britain.

In other embodiments, the methods described herein are performed in vivo, i.e., the one or more elephant TP53-encoding nucleic acids sequences, the one or more elephant p53 proteins, or compositions thereof are administered directly to an animal in need thereof, desirably a mammal (such as those described herein), and preferably a human suffering from cancer. The methods described herein are well suited for in vivo administration to a mammal, e.g., a human, canine, etc. The one or more elephant nucleic acid sequences, proteins, or composition can be administered to a mammal (e.g., a human, canine, etc.) using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection. In certain embodiments, the effect of delivery to the cancer cell of the one or more elephant nucleic acid sequences, proteins, or composition described herein is therapeutic, i.e., the effect partially or completely cures a disease and/or adverse symptoms attributable to the disease (e.g., cancer). To this end, the method described herein comprises administering a "therapeutically effective amount" of the one or more elephant nucleic acid sequences, proteins, or composition described herein. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the one or more elephant nucleic acid sequences, proteins, or composition to elicit a desired response in an individual. For example, a therapeutically effective amount of an elephant TP53 nucleic acid or protein may be an amount which increases p53 protein bioactivity in a human and/or enhances the p53 signaling pathways against a cancer. Desirably, the therapeutic effect results in the death of the cancer cell.

Alternatively, the pharmacologic and/or physiologic effect may be prophylactic, i.e., the effect completely or partially prevents a disease or symptom thereof (e.g., cancer). In this respect, the method described herein comprises administering a "prophylactically effective amount" of the one or more elephant nucleic acid sequences, proteins, or composition described herein. A "prophylactically effective amount" refers to an amount effective, at dosages and for periods of time necessary, to achieve a desired prophylactic result (e.g., prevention of disease onset). Preferably, the prophylactic results in the prevention of cancer.

EXAMPLES

The following examples further illustrate the invention but, of course, should not be construed as in any way limiting its scope.

Example 1

This example describes the cancer rates in different mammal species (including elephants) to determine if body mass correlates with cancer incidence.

Necropsy data was examined from zoo animals to determine if cancer incidence increases with body size or life span. Fourteen years of necropsy data collected by the San Diego Zoo (Feng et al., *PNAS;* 104(42): 16633-16638 (2007)) was compiled and the tumor incidence was calculated for 36 mammalian species, spanning up to 6 orders of magnitude in size and life span (*American Cancer Society; Cancer Facts & Figures* (2015)). Data from the Elephant Encyclopedia (Griner et al., *Pathology of Zoo Animals*; Zoological Society of San Diego (1983)) was used to analyze the cause of death for captive African (*Loxodonta africana*) and Asian (*Elephas maximus*) elephants, and to estimate the age incidence and overall lifetime cancer risk. Using a previously established cancer transformation model (de Magalhaes et al., *J Evol Biol;* 22(8): 1770-1774 (2009)), the percentage decrease in the cellular mutation rate was calculated to account for a 100× increase in cell mass (the difference between elephants and humans) without cancer development.

TABLE 1

| Age Range | Total Necropsies | # Euthanized non-cancer | # Non-cancer disease | # Exogenous mortality | # Euthanized unspecified | # Disease unspecified | # Euthanized Cancer | # Cancer | Observed % cancer [95% CI] | Inferred % cancer [95% CI] |
|---|---|---|---|---|---|---|---|---|---|---|
| 0-5 | 125 | 15 | 77 | 28 | 1 | 2 | 0 | 2 | 1.60 [0.00, 4.24] | 2.40 [0.00, 5.44] |
| 6-15 | 83 | 20 | 36 | 19 | 4 | 1 | 1 | 2 | 3.61 [0.00, 8.02] | 6.02 [0.58, 11.47] |
| 16-25 | 121 | 35 | 48 | 25 | 7 | 2 | 2 | 2 | 3.31 [0.00, 6.69] | 4.96 [0.86, 9.05] |
| 26-35 | 108 | 27 | 51 | 15 | 8 | 4 | 3 | 0 | 2.78 [0.00, 6.11] | 3.70 [0.00, 7.60] |
| 36-45 | 94 | 32 | 27 | 13 | 12 | 5 | 0 | 5 | 5.32% [0.47, 10.16] | 6.38 [1.18, 11.58] |
| 46-55 | 70 | 14 | 23 | 7 | 7 | 17 | 1 | 1 | 2.86 [0.00, 7.37] | 5.71 [0.00, 11.59] |
| 56+ | 43 | 3 | 7 | 6 | 7 | 19 | 1 | 0 | 2.33 [0.00, 8.16] | 6.98 [0.00, 15.29] |
| Lifetime [0-56+] | 644 | 146 | 269 | 113 | 46 | 50 | 8 | 12 | 3.11 [1.74, 4.47] | 4.81 [3.14, 6.49] |

The 36 mammalian species analyzed spanned from the striped grass mouse (weight of 51 g, maximum life span of 4.5 years) to the elephant (weight of 4800 kg, maximum life span of 65 years). Cancer risk did not increase with mammalian body size and maximum life span among the 36 species analyzed (e.g., for rock hyrax, 1% [95% CI, 0%-5%]; African wild dog, 8% [95% CI, 0%-16%]; and lion, 2% [95% CI, 0%-7%]) (FIG. 1). No significant relationship was found with any combinations of mass, life span, and basal metabolic rate and cancer incidence. Among the 644 annotated elephant deaths from the Elephant Encyclopedia database, the lifetime cancer incidence was found to be 3.11% (95% CI, 1.74%-4.47%) (Table 1). To obtain a more conservative estimate, an inferred cancer incidence was calculated for cases that lacked adequate details for the cause of death, leading to an estimated elephant cancer mortality rate of 4.81% (95% CI, 3.14%-6.49%). Based on an algebraic model of carcinogenesis (de Magalhaes et al., *J Evol Biol;* 22(8): 1770-1774 (2009)), a 2.17-fold decrease in mutation rate was calculated as sufficient to protect elephants from cancer development given their 100× increased cellular mass compared with humans. Overall, the cancer mortality rate for elephants was found to be less than 5% compared with a cancer mortality rate for humans of 11% to 25% (25).

The results of this example demonstrate that larger animals with longer life spans, including elephants, may develop less cancer, compared to smaller animals.

Example 2

This example describes a genomic analysis of cancer-related genes in elephants.

Genomic sequence analysis was performed on the publicly available scaffolds of the African elephant genome in the Ensembl database (release 72) and the NCBI GenBank database; specifically, cancer-related genes (including oncogenes and tumor suppressors) were examined. Sequence alignments of TP53 were explored in related species, and African and Asian elephant TP53 retrogenes were cloned and resequenced. Capillary sequencing was performed on single elephants to avoid issues of single-nucleotide polymorphisms (SNPs) between elephants. Whole genome sequencing (ILLUMINA® HISEQ 2500® Sequencing System; Illumina Inc., San Diego, Calif.) was performed on freshly extracted DNA from an African elephant at 40× average sequence coverage, with more than 100× coverage within areas of the TP53 gene.

Figure 2:
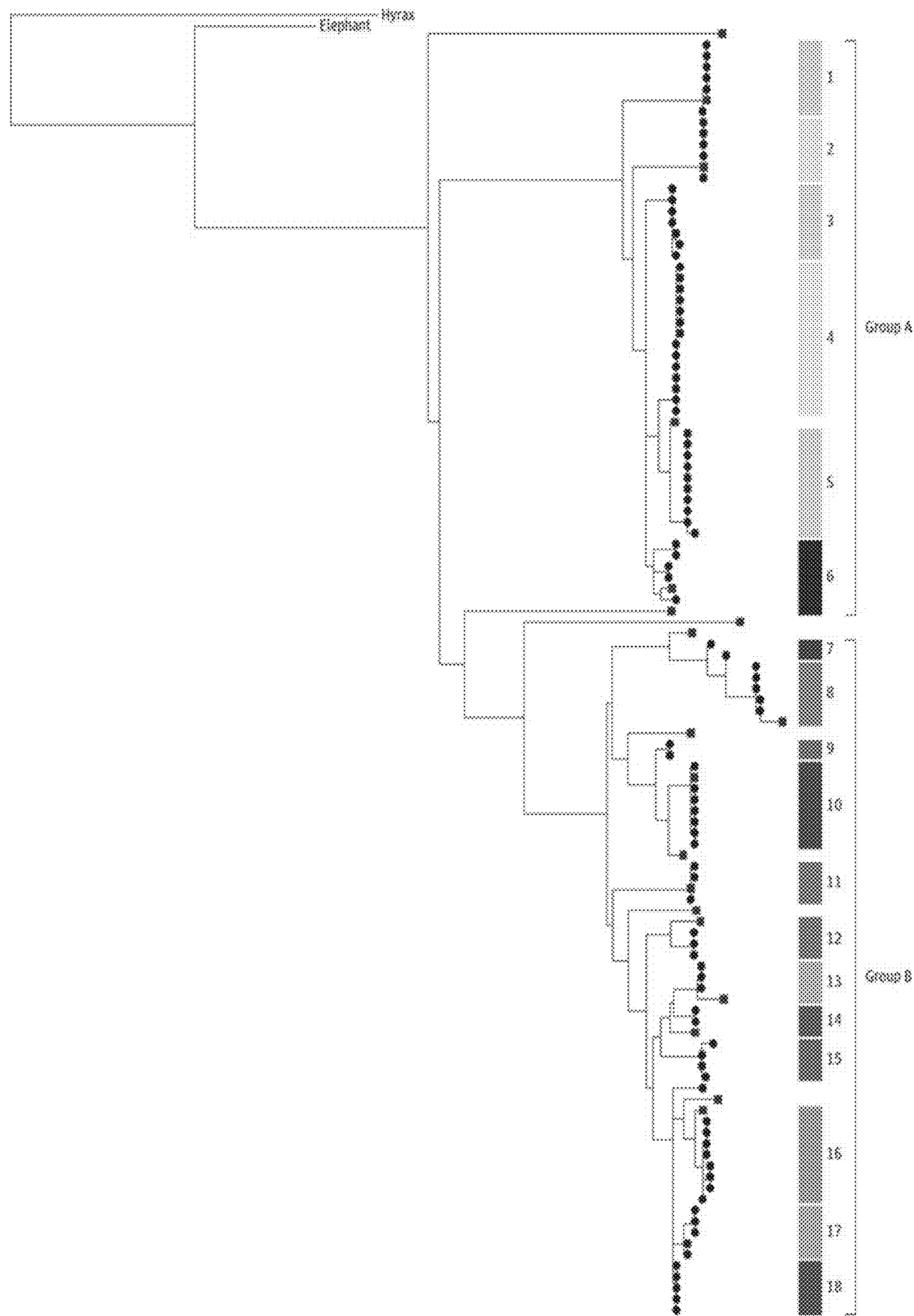
FIG. 2 is a phylogenic tree showing group A and group B TP53 retrogenes in the African elephant.

A maximum likelihood phylogeny was used to cluster the sequenced TP53 retrogene clones and to confirm the number of unique genes uncovered in the African elephant genome. The phylogeny allowed for visualization of TP53 retrogene similarity to one another as well as their relationship to the ancestral TP53 sequence in the elephant and hyrax. The capillary sequenced clones from this study are shown as circles and the published sequences from GenBank are shown as squares. The African elephant (*L. africana*) draft genome LoxAfr3 contains 19 copies of TP53 (FIG. 2). Phylogenic analysis reveals at least 18 distinct clusters of processed TP53 copies. These clusters fall into 2 groups, labeled Group A and Group B. The human haploid genome contains 1 copy of TP53, while Ensembl and GenBank annotate a large number of TP53 paralogs in the African elephant genome (12 and 20 haploid copies, respectively).

Elephant sequence alignments revealed that one TP53 copy with a comparable gene structure to TP53 was found in other mammalian species (ancestral copy).

The other 19 copies lacked true introns, suggesting that they originated from retrotransposition (retrogenes). Whole-genome sequencing with deep coverage confirmed one ancestral copy and 19 total retrogene copies, similar to the 20 total copies annotated in GenBank for TP53. Eleven of the 18 retrogenes from the capillary sequencing were similar, but not identical, to previous Gen-Bank annotations and local whole genome sequencing data. High variance in coverage across reference TP53 copies indicated additional TP53 elephant copies that may not yet have been successfully assembled.

There was no evidence for 8 of the published retrogene copies, possibly because of under-sampling of clones, misassembly in the published genome, or differences between individual elephants. An additional 7 cloned sequences had support from multiple clones but were not found in either database. It is also possible that TP53 copies in the genome may have been undetected by the polymerase chain reaction (PCR) primers. The Asian elephant DNA was also found to contain 15 to 20 copies of Group A and B TP53 retrogenes.

Figure 3A:
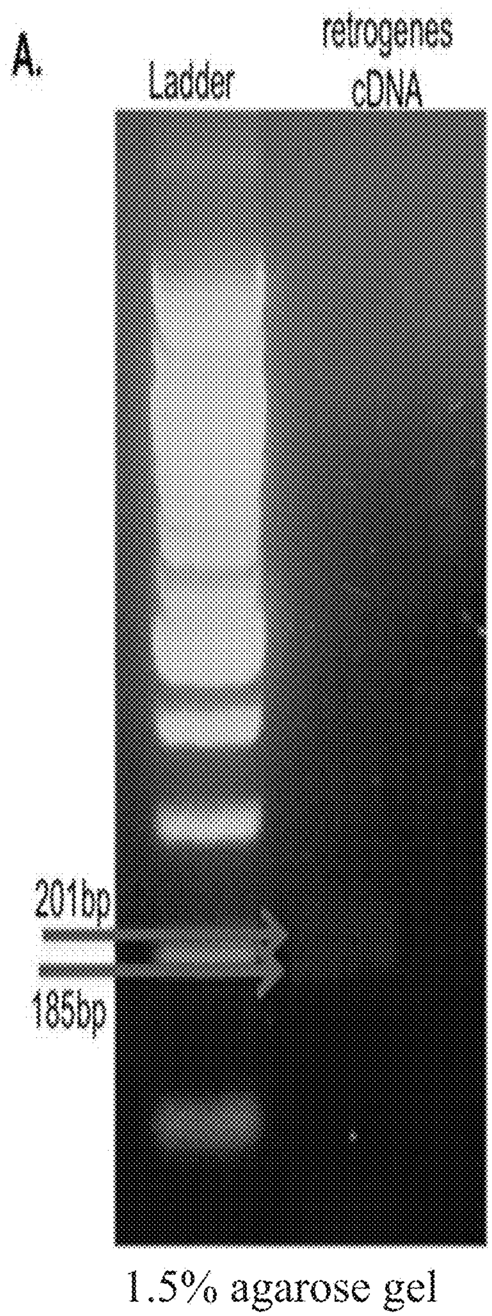
FIG. 3A is an image of an electrophoresis gel showing results of TP53-specific RT-PCR performed on PBMCs from African and Asian elephants and African elephant fibroblasts. Two bands at 201 bp and 185 bp are shown, which correlate with Group A and Group B of the elephant p53 retrogenes.
Figure 3B:
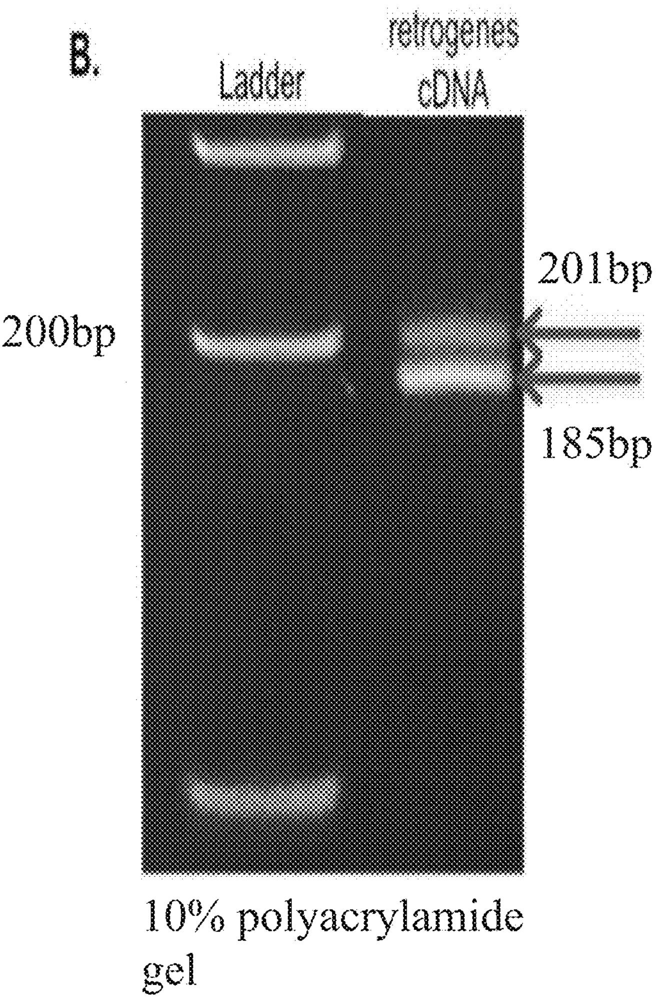
FIG. 3B is a higher resolution image of the PCR results depicted in FIG. 3A.

In order to establish whether elephants express TP53 retrogenes ($EP53^{r}$), functional molecular analysis of TP53 and its retrogenes was performed on peripheral blood mononuclear cells (PBMCs) from African and Asian elephants, and fibroblasts from an African elephant. The RNA was isolated from PBMCs and fibroblasts that were exposed to 2 Gy ionizing radiation, and reverse transcription-polymerase chain reaction (RT-PCR) was performed. The PCR primers were designed to distinguish the TP53 retrogenes from the ancestral sequence ($EP53^{anc}$) and splice variants. The RT-PCR products were observed at 201 bp and 185 bp on a gel (FIG. 3A), the expected sizes for the Group A and Group B EP53 retrogenes, respectively, and Sanger sequencing confirmed their identities as retrogenes. A higher resolution image is shown in FIG. 3B.

The results of this example suggest that elephants have 19 TP53 retrogenes ($EP53^{r}$), which can be divided into two groups (Group A and Group B), and one ancestral TP53 gene ($EP53^{anc}$).

Example 3

This example demonstrates whether elephant EP53 retrogenes transfected into human cell lines could be translated into proteins.

Mammalian expression vectors were cloned to produce elephant p53 retrogene ($EP53^{r}$) proteins fused to an epitope from the myc protein. The myc tag was used to immunoprecipitate the translated protein from cell lysates, and/or to probe for the protein on a western blot. Constructs were developed for five different $EP53^{r}$s: retrogene 1, retrogene 5, retrogene 7, retrogene 9, and retrogene 17. These retrogenes were selected because they represent the spectrum of different EP53 genes. All 5 $EP53^{r}$s were expressed as truncated proteins, compared to the full size of the EP53 protein, which runs around 53 kDa (similar to human p53).

Human embryonic kidney cells (HEK293), mouse fibroblasts (NIH 3T3), and human osteosarcoma cells (U-2OS) were transfected with one of the myc-tagged $EP53^{r}$ plasmids (myc-$EP53^{r}$). The data from the HEK293 cells are shown, and are representative of the experiments performed in the other cells types. Lipid-based transfection was performed, and the cells were also transfected with empty vector as a negative control. 24 hours after transfection, the cells were placed in media containing antibiotics to selectively kill cells that did not express the gene of interest. Once selection was complete, doxycycline was added to induce gene expression, which was confirmed by western blot.

The cancer cell lines U-2OS (osteosarcoma) and HCT116 (colon cancer) were also infected with lentiviral vectors to generate stable cell lines expressing elephant $EP53^{r}$ proteins. The plasmids used to make lentiviruses were tetracycline-inducible gene expression plasmids, in which the gene of interest is only expressed when cells are treated with doxycycline. 24 hours after viral transduction, cells were placed in media containing antibiotics to eliminate cells that did not express the gene of interest. Once selection was complete, expression of the gene of interest was confirmed by western blot.

P53 is upregulated in response to DNA damage, so to confirm that the transfected or transduced cells could express the genes of interest, the cells were treated with either MG132 (a protease inhibitor) or doxorubicin (intercalates with DNA to prevent macromolecular biosynthesis) to induce DNA damage. For tetracycline inducible cells, the cells were treated with doxycycline for 24-48 hours prior to treatment with MG132 or doxorubicin. After the induction of DNA damage, the cells were harvested and pelleted. The cell pellets were frozen, and then lysed in cell lysis buffer containing phosphatase and protease inhibitors. The cell lysates were run on SDS-PAGE protein gels, and then transferred to PVDF membranes (western blots). The membranes were blocked, and then probed with primary antibodies to determine the p53 protein levels. The blots were probed with secondary HRP-conjugated antibodies, and the protein levels were detected using a substrate and a chemiluminometer. GAPDH was used as a loading control for each western blot. The blots were also probed for phosphorylated $EP53^{r}$ at the serine-15 residue (phospho-$EP53^{r}$). DNA damage induces the phosphorylation of p53, which reduces the interaction of this protein with its negative regulator, mouse double minute 2 (MDM2) (Milczarek et al. Life Sci; 60: 1-11 (1997)).

Figure 4A:
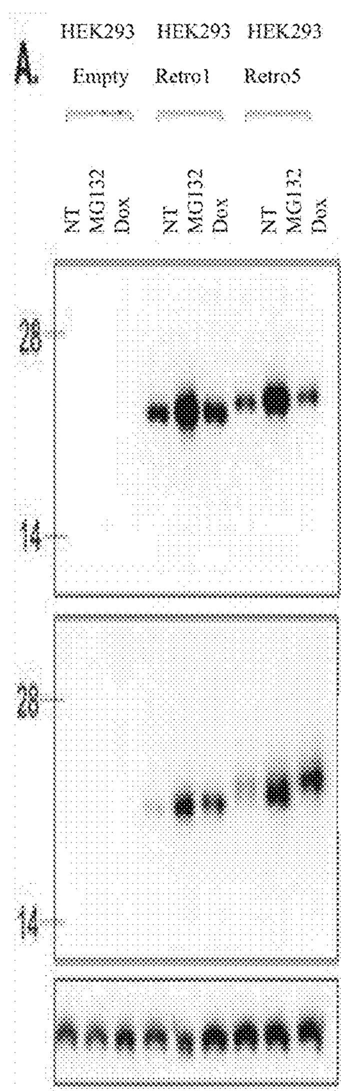
FIG. 4A and FIG. 4B are images of western blots showing that HEK293 cells transfected with EP53 retrogenes increase the expression of the proteins in response to DNA damage induced by MG132 or doxorubicin.
Figure 4B:
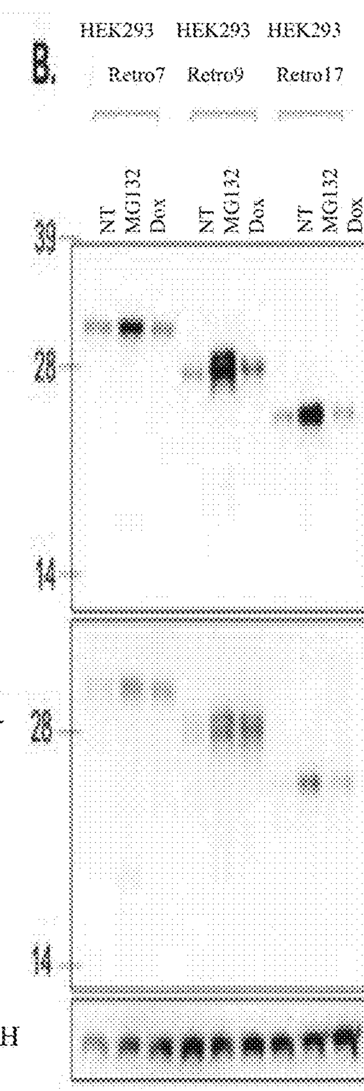
Figure 4C:
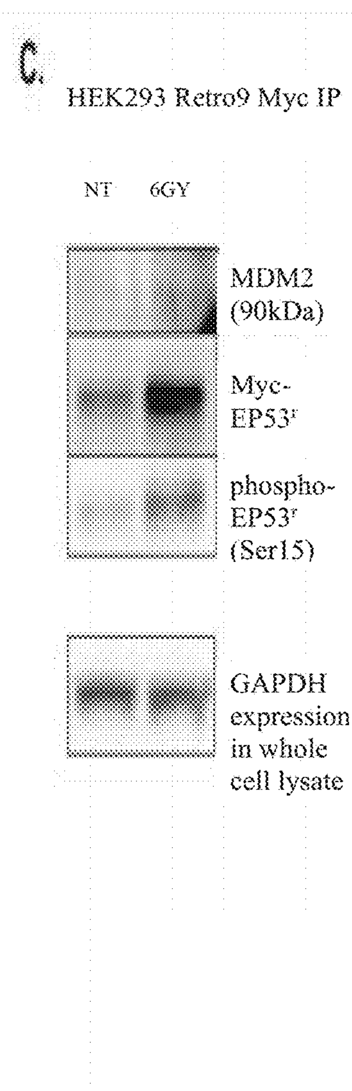
FIG. 4C is an image of a western blot showing that HEK293 cells transfected with $EP53^{r9}$ are able to upregulate the protein, and increase expression of the phosphorylated protein, in response to DNA damage from ionizing radiation.

Following treatment of the transfected cells with 10 μM MG132 or 1 μM doxorubicin, an increase in protein labeling was observed for all five $EP53^{r}$s in HEK293 cells, as well as an increase in the labeling for phospho-$EP53^{r}$ (FIGS. 4A and 4B). This suggested successful transfer of the genes to the cells, and that the $EP53^{r}$ genes could be translated into proteins. The increase in phospho-$EP53^{r}$ confirmed that MG132 was preventing proteasomal degradation of the elephant protein. It was next determined whether the $EP53^{r}$s could interact with the negative regulator, MDM2. To determine if the $EP53^{r}$s could bind MDM2, HEK293 cells were transfected with $EP53^{r9}$, and subjected to 6 Gy ionizing radiation to induce DNA damage. The expressed $EP53^{r9}$ protein was then immunoprecipitated with an antibody to the myc tag, and run on a western blot. Immunoblots showed that 6 Gy ionizing radiation increased $EP53^{r9}$ expression and phosphorylation, indicative of protein stabilization upon DNA damage, and additionally that MDM2 co-immunoprecipitated with myc-$EP53^{r9}$, indicating that the two proteins do interact (FIG. 4C).

The results of this example demonstrate that myc-$EP53^{r}$s can be transfected into cells and generate protein in response to DNA damage, and interact with MDM2.

Example 4

This example describes the cellular response to DNA damage in peripheral blood lymphocytes of elephants and humans.

Experiments were performed on peripheral blood lymphocytes (PBLs) from three groups of subjects: African and Asian elephants, a representative clinical cohort of patients with Li-Fraumeni Syndrome (LFS) enrolled in the Cancer Genetics Study at the University of Utah, and age-matched human controls without a significant family history of cancer (also enrolled in the Cancer Genetics Study). Patients with LFS were selected for inclusion as a representative sample based on their TP53 mutation status, varied cancer history, and availability for blood draws. Follow-up laboratory experiments were also performed on African elephant fibroblasts, human fibroblasts, and HEK293 cells to confirm the results.

Ionizing radiation (0.5, 2, 5, 6, 10, and 20 Gy) or doxorubicin (0.005-30 μM) were used to induce DNA damage in the cultured primary PBLs, which were then evaluated for signs of apoptosis, DNA repair efficiency, and cell cycle arrest. Apoptosis was evaluated by measuring the number of cells that stained for Annexin V (AV) and propidium iodide (PI); cells were categorized as being in late apoptosis if they were AV+ PI+, and in early apoptosis if they were AV+ PI−. Apoptosis was also measured either using APO-TOX GLO™ (Promega, Madison, Wis.) or CASPASE-GLO® 3/7 Assay (Promega) and CELLTITER-GLO® (Promega). The results were normalized to cell viability either using counts from the MULTI-TOX-FLUOR™ assay (Promega) included with APO-TOX GLO™, or using CELLTITER-GLO® when caspase activity was measured. Statistically significant differences in apoptosis were calculated in GRAPHPAD PRISM®.

Following 2 Gy and 6 Gy ionizing radiation, African elephant PBLs exhibited apoptosis at significantly elevated rates, compared with human PBLs, after 18 hours (late apoptosis: 33.20% compared to 14.07%, respectively; P<0.001 (FIG. 5A); early apoptosis: 21.07% compared to 11.73%, respectively; P<0.001(FIG. 5B)). African elephant lymphocytes also exhibited a significant increase in late (FIG. 6A) and early (FIG. 6B) apoptosis at 18 and 24 hours when exposed to 5 μM of doxorubicin.

Figure 7:
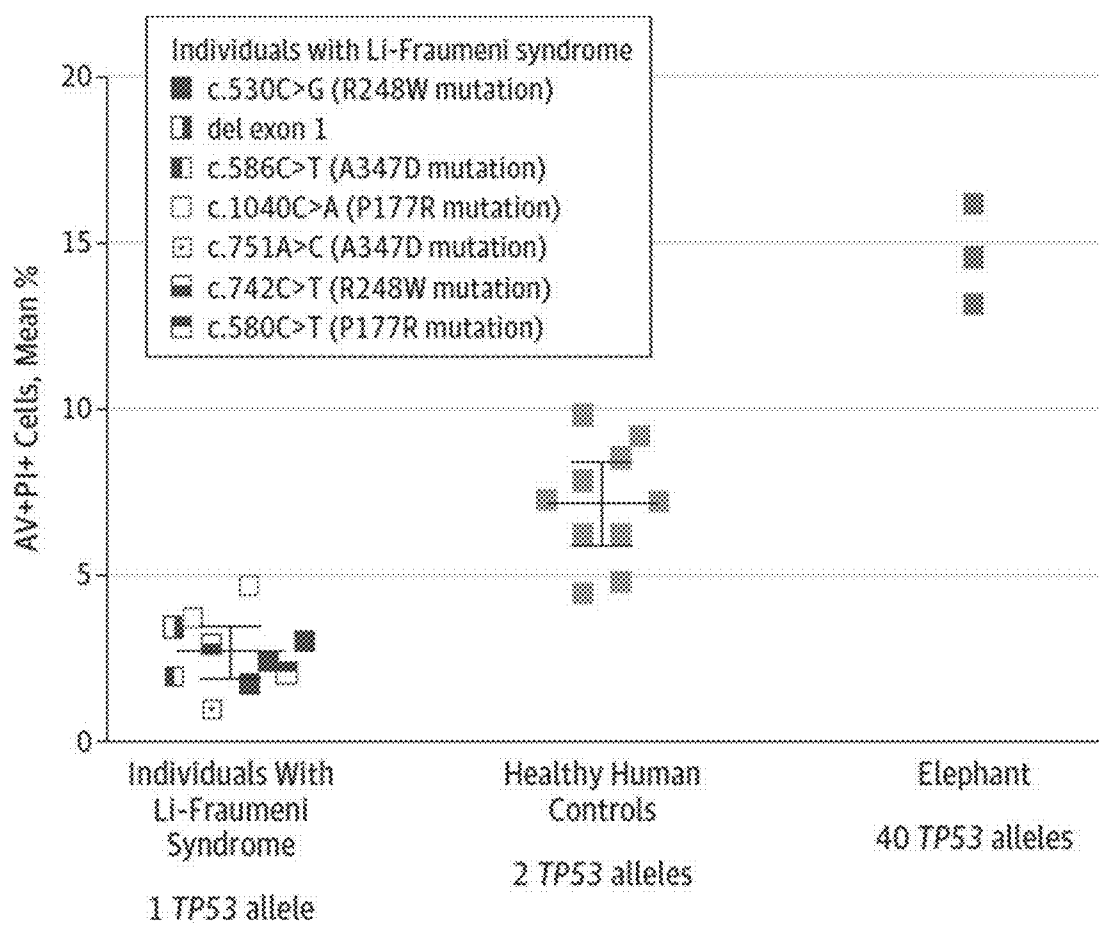
FIG. 7 is a scatter plot showing the percentage of peripheral blood lymphocytes undergoing late apoptosis following exposure to 2 Gy ionizing radiation, from patients with Li-Fraumeni syndrome, 10 healthy controls, and 1 African elephant.

Peripheral blood lymphocytes from individuals with LFS (n=10), healthy controls (n=10), and 1 African elephant, treated with 2 Gy of ionizing radiation revealed different levels of apoptosis (apoptosis calculated by subtracting the percentage of AV+PI+ cells treated with 2 Gy ionizing radiation, from the percentage of AV+PI+ cells cultured without treatment). Cells of patients with LFS underwent significantly less apoptosis compared with healthy human PBLs (2.71% relative to 7.17%; P<0.001) and elephant PBLs (14.64%; P<0.001) (FIG. 7).

Figure 8:
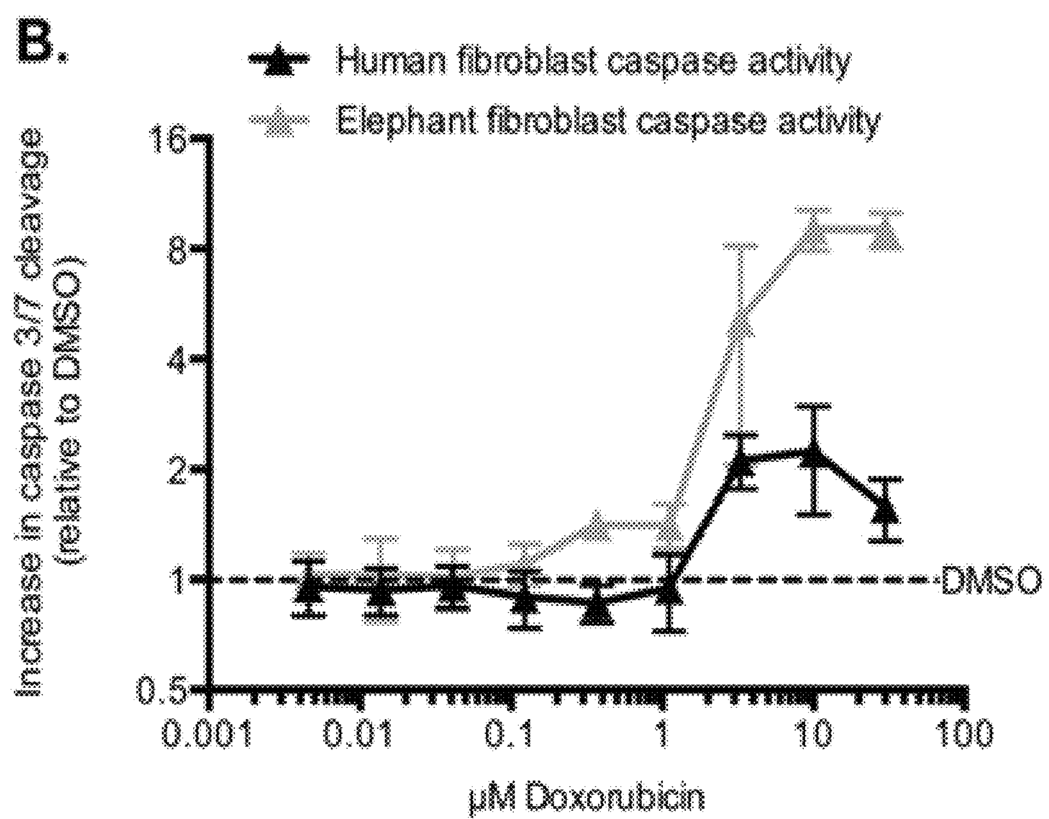
FIG. 8 is a line graph showing that elephant fibroblasts exhibit greater caspase 3/7 cleavage than human fibroblasts following exposure to doxorubicin.

Similar to lymphocytes, a higher rate of apoptosis (as a metric of increased caspase 3/7 cleavage) was also observed in elephant fibroblasts (FIG. 8) subjected to DNA damage by 10 μM and 30 μM doxorubicin (elephant: 9.1-fold increase; human: 2.24-fold increase; P<0.001). The elephant fibroblasts cells additionally showed reduced viability consistent with cell cycle arrest after 0.5 Gy of ionizing radiation (elephant: 80.81% compared to human: 95.87%; P=0.01).

Figure 9:
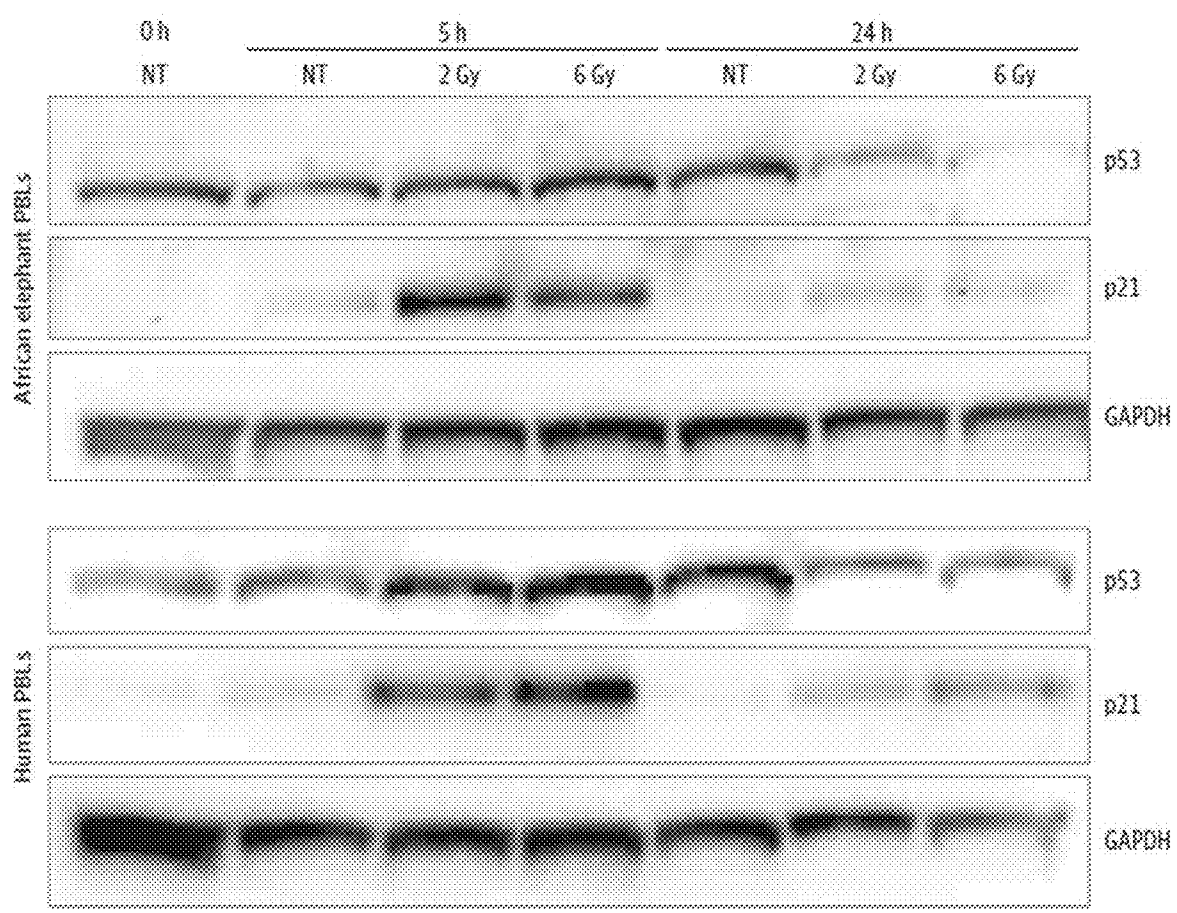
FIG. 9 is an image of a western blot showing an increase in p53 and p21 protein expression 5 hours and 24 hours after 2 Gy and 6 Gy ionizing radiation.

P53 plays a critical role in p21 and MDM2 protein induction following DNA damage (Macleod et al, *Genes Dev;* 9(8): 935-944 (1995); Yoon et al. *PNAS;* 99(24): 15632-15637 (2002)), so p21 expression was evaluated on immunoblots to validate that the DNA damage response in elephant cells to radiation was dependent on P53. Both elephant and human PBLs showed an increase in p53 and p21 protein expression following ionizing radiation exposure (FIG. 9). More p21 protein expression was observed at 5 hours in elephant PBLs treated with 0.5 Gy of ionizing radiation compared with human PBLs (20.1-fold increase relative to 3.5-fold increase; P=0.004). Elephant fibroblasts also showed increased p21 protein expression following 2 Gy of ionizing radiation at 5 hours (1.9-fold increase) compared with no increase in human fibroblasts.

As a post hoc analysis, the same experiments were repeated in PBLs from multiple Asian elephants (n=6) of different ages (2, 12, 17, 38, 57, and 69 years old). Asian elephant lymphocytes also demonstrated an increased rate of apoptosis (50.63% relative to human cells 23.67%; P<0.001) when exposed to 2 Gy of ionizing radiation (FIG. 10A) and an increase in p21 expression (FIG. 10B). Additionally, the apoptotic response in PBLs decreased with the age of Asian elephants when tested with both a linear regression and a Jonckheere-Terpstra test, which allows for nonlinear relationships (FIG. 10C) (2-year-old elephant with 2 Gy radiation at 18 hours, 52.53% [95% CI, 35.86%-69.2%] and 69-year-old elephant, 40.03% [95% CI, 30.64%-49.43%]; P=0.002 by linear regression; P<0.001 by Jonckheere-Terpstra test).

HEK293 cells express adenovirus proteins that naturally inhibit the function of p53; however the mouse fibroblast cell line, NIH3T3, expresses a functional TP53 gene. Therefore additional studies were conducted in NIH3T3 cells to test the effect on cell survival of $EP53^{r5}$ and $EP53^{r9}$ expression in cells that also express functional wild type TP53. NIH3T3 cells were transfected with $EP53^{r5}$ or $EP53^{r9}$ and then treated with doxorubicin to induce DNA damage. As shown in FIG. 11, a significant increase in caspase activity of the NIH 3T3 cells transfected with $EP53^{r5}$ (FIG. 11A) and $EP53^{r9}$ (FIG. 11B) was observed relative to control cells, suggesting that $EP53^{r5}$ and $EP53^{r9}$ expression increases apoptosis in cells that already express functional TP53.

TABLE 2

| | % of viable cells with the indicated # of pH2AX foci | | | | | | | |
|---|---|---|---|---|---|---|---|---|
| | 0-5 foci | | 6-10 foci | | 11-15 foci | | 16-20+ foci | |
| Treatment | Human | Elephant | Human | Elephant | Human | Elephant | Human | Elephant |
| NT 1 h | 97.3 | 98.7 | 2.7 | 1.3 | 0.0 | 0.0 | 0.0 | 0.0 |
| NT 5 h | 97.7 | 98.0 | 2.3 | 1.3 | 0.0 | 0.7 | 0.0 | 0.0 |
| NT 24 h | 99.7 | 99.7 | 0.3 | 0.3 | 0.0 | 0.0 | 0.0 | 0.0 |
| 2GY 1 h | 23.0 | 26.3 | 25.3 | 33.7 | 19.0 | 17.0 | 32.7 | 23.0 |
| 2GY 5 h | 46.7 | 51.0 | 32.7 | 39.0 | 14.3 | 9.0 | 6.3 | 1.0 |
| 2GY 24 h | 94.3 | 92.3 | 5.3 | 7.3 | 0.3 | 0.0 | 0.0 | 0.0 |

The efficiency of DNA repair was next evaluated by determining the number of phospho-histone H2AX (pH2AX) labeled foci, an indicator of double-stranded breaks in the DNA. The cells were cultured for 1, 5, 10, 18, 24, and 72 hours after the induction of DNA damage by 2 Gy ionizing radiation, and then evaluated. Lymphocytes undergo p53-dependent apoptosis in response to DNA damage (Heinrichs et al. *Oncogene;* 22(4): 555-571 (2003); Lowe et al. *Cell;* 74(6): 957-967 (1993)), while fibroblasts undergo both p53-dependent apoptosis and cell cycle arrest (Antoccia et al. *J Radiat Res;* 50(5): 457-468 (2009); Kastan et al. *Cell;* 71(4): 587-597 (1992); Attardi et al. *Oncogene;* 23(4): 973-980 (2004)); both elephant cell types were tested accordingly.

Ionizing radiation did not cause a significant difference in the percentage of cells with labeled pH2AX foci in human and elephant PBLs, indicating that the increased apoptosis in elephants cannot be attributed to more DNA damage (Table 2). Cells were binned by the number of pH2AX foci (0-5, 6-10, 11-15, 16-20+), and demonstrated no significant difference in the rate of DNA damage repair between humans and elephants.

TABLE 3

| Gene Name | Log 2 Increase Compared to NT | Adjusted P Value |
|---|---|---|
| MDM2 | 2.62 | 1.24E−166 |
| CCNG1 | 2.13 | 2.68E−140 |
| TP53INP1 | 2.69 | 1.31E−134 |
| DIS3 | 1.53 | 1.70E−88 |
| PLXNB2 | 3.51 | 3.54E−86 |
| BAX | 1.83 | 2.77E−78 |
| PHLDA3 | 5.79 | 3.85E−72 |
| DNA2 | 2.19 | 2.15E−68 |
| RPS27L | 2.04 | 3.83E−60 |
| ZNF608 | 1.73 | 1.07E−58 |
| ZMAT3 | 2.83 | 2.24E−54 |
| CHST14 | 2.63 | 1.04E−51 |
| SDK2 | 3.31 | 8.14E−46 |
| FAT1 | 2.40 | 2.27E−45 |
| TNS1 | 3.93 | 4.51E−37 |
| IZUMO4 | 3.05 | 1.13E−30 |
| POLH | 1.73 | 1.78E−30 |
| PVRL4 | 2.92 | 3.59E−29 |
| PLXNA2 | 2.78 | 3.04E−28 |
| SNAI3 | 2.94 | 5.57E−28 |

To identify changes in gene expression in elephant cells in response to DNA damage, elephant peripheral blood lymphocytes were treated with 2 Gy ionizing radiation. Irradiated and untreated cells were cultured at 37° C. for 5 hours. RNA was extracted from the cells and treated with DNase to remove genomic DNA. RNA-sequencing was performed, and the top 20 most upregulated genes in elephant cells after exposure to radiation were compiled. In Table 3, genes highlighted in gray are known targets or regulators of p53 in human cells. These results suggest that DNA damage induces p53-dependent signaling pathways in elephant cells, similar to the p53-signaling pathways induced by DNA damage in human cells.

The results of this example demonstrate that elephant cells execute higher levels of apoptosis in response to DNA damage, and that when EP53 proteins are transduced into human cells, these cells are able to execute higher levels of apoptosis in response to DNA damage.

Example 5

This example evaluates whether EP53 expression could increase apoptosis of the human cancer line, U-2OS (osteosarcoma) transfected with various EP53 genes.

U-2OS cells were transfected with $EP53^{r5}$ or EP53 ancestral ($EP53^{anc}$), and then treated with doxycycline to induce $EP53^{r}$ expression. The cells were then treated with doxorubicin to damage the DNA. As shown in FIG. 12A, a significant increase in caspase activity was observed in the $EP53^{r5}$-transduced cell line compared to control cells with an empty vector, suggesting that $EP53^{r5}$ expression increases apoptosis of cancer cells that also express functional TP53.

U-2OS cells were also transduced with $EP53^{anc}$. These cells were then induced to express $EP53^{anc}$, and treated with doxorubicin to trigger DNA damage. As shown in FIG. 12B, cells induced to express $EP53^{anc}$ had a 20-fold increase in caspase activity, compared to cells transduced with an empty vector. These cells exhibited more phosphor-$EP53^{anc}$, as was an increase in the p53 target genes, p21 and MDM2 (FIG. 12C). Cells that expressed $EP53^{anc}$ also expressed less endogenous human p53. Even in the absence of doxorubicin treatment, U-2OS cells expressing $EP53^{anc}$ underwent significant apoptosis compared to cells that were transduced with empty vector.

Figure 13:
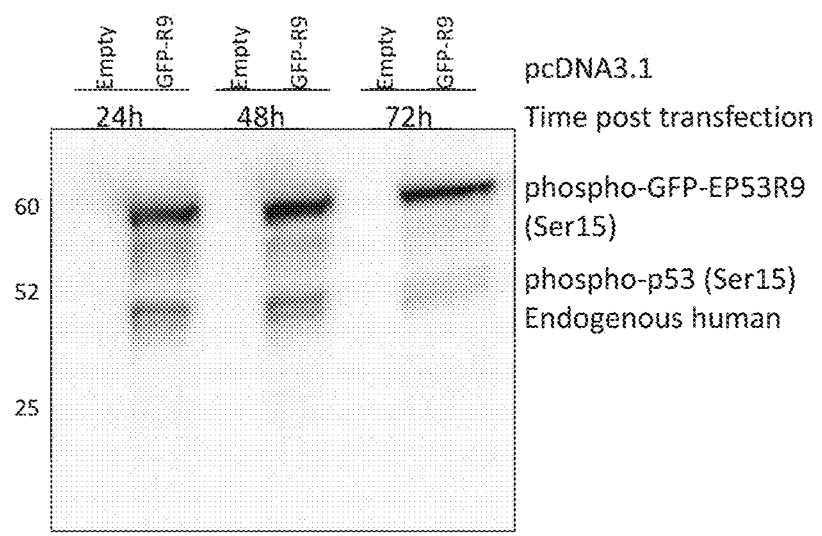
FIG. 13 is a western blot showing that U-2OS cells transfected with GFP-labeled $EP53^{r9}$ exhibit an increase in phosphorylated-$EP53^{r9}$, with a concomitant decrease in phosphorylated-human P53.

Additional experiments were conducted in which U-2OS cells were transfected with $EP53^{r9}$ tagged with GFP (GFP-$EP53^{r9}$). After 24, 48, or 72 hours post-transfection, the cells were harvested and the whole cell lysates were processed for western blotting. The blots were probed for phospho-$EP53^{r9}$, as well as endogenous human phosphor-p53. It was found that in addition to increased expression of EP53r9, the U-2OS cells exhibited restoration of the wild type p53 response, which induced apoptosis of these cells (FIG. 13).

U-2OS cells were also transfected with $EP53^{anc}$ and human TP53, and the cell viability after induction with doxycycline was observed after 72 hours. It was found that in cells transfected with elephant p53, cell viability dropped to 35.6% (SEM 1.85), whereas cells transduced with human p53 only dropped to 46.1% (SEM 1.12) cell viability, suggesting that elephant p53 is able to kill more human cancer cells than human p53 alone. The U-2OS cells transfected with $EP53^{anc}$ also saw an increase in caspase activity (14.22%, SEM 0.23) relative to cells transfected with human p53 (10.89%, SEM 0.12), consistent with an increase in apoptotic activity following induction of elephant p53 proteins.

To examine the effect of $EP53^{r9}$ expression on cellular senescence of human colon cancer cells, HCT116 cancer cells were transduced with a tetracycline-inducible vector encoding $EP53^{r9}$. Protein expression was then induced with doxycycline, and cells were then treated with doxorubicin to damage the DNA. HCT116-$EP53^{r9}$ cells exhibited significantly more caspase activity compared to control cells (FIG. 14A). Western blots were performed to confirm expression of $EP53^{r9}$ in these cells (FIG. 14B). It was found that cells treated with increasing concentrations of doxycycline expressed more endogenous human phosphorylated-p53 (Ser15) compared to cells that did not express $EP53^{r9}$. The cells were transduced with flag-tagged $EP53^{r9}$, and an antibody to flag was used to verify expression of $EP53^{r9}$. Cells were treated with 5-FU to activate the p53 pathway. These results suggest that $EP53^{r9}$ increased apoptosis by increasing the amount of activated endogenous p53 in these cells.

The results of this example demonstrate that induction of EP53 in cancer cell lines causes a significant increase in apoptosis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a pharmaceutically acceptable carrier and (a) one or more nucleic acids each having a sequence encoding an elephant p53 protein, selected from the group consisting of SEQ ID NO: 2, SEQ ID NO: 12, and SEQ ID NO: 20, or (b) one or more elephant p53 proteins each having a sequence selected from the group consisting of SEQ ID NO: 3, SEQ ID NO: and 13, SEQ ID NO: 21.

2. The composition of claim 1, which comprises one or more nucleic acid sequences each encoding an elephant p53 protein.

3. The composition of claim 1, which comprises one or more elephant p53 proteins.

4. The composition of claim 1, wherein the composition further comprises a liposome.

5. The composition of claim 4, wherein the one or more nucleic acid sequences or one or more P53 proteins are encapsulated within the liposome.

6. The composition of claim 1, wherein the composition further comprises a nanoparticle.

7. The composition of claim 6, wherein the nanoparticle comprises one or more fillers selected from the group consisting of a lipid, a polymer, a metal, and a carbon nanostructure.

8. The composition of claim 6, wherein the one or more nucleic acid sequences or one or more p53 proteins are encapsulated within a nanoparticle.

9. The composition of claim 6, wherein the nanoparticle comprises an external surface decorated with a moiety for reducing an interaction with the reticuloendothelial system.

10. The composition of claim 9, wherein the moiety comprises polyethylene glycol.

11. The composition of claim 9, wherein the moiety comprises a targeting moiety.

12. The composition of claim 11, wherein the targeting moiety increases affinity of the nanoparticle for a cancer cell.

13. The composition of claim 1, which further comprises one or more additives selected from the group consisting of a small molecule chemotherapeutic, a monoclonal antibody, and an imaging agent.

14. The composition of claim 13, wherein the imaging agent comprises a contrast agent comprising gadolinium (Gd), a sugar, or an iron complex.

15. The composition of claim 1, wherein the one or more nucleic acids are retrogenes or the one or more elephant p53 proteins are encoded by a retrogene.

16. The composition of claim 1, wherein the one or more nucleic acids are ancestral genes or the one or more elephant p53 proteins are encoded by an ancestral gene.

17. The composition of claim 1, which comprises two or more elephant p53 proteins, wherein at least two of the elephant p53 proteins have different sequences selected from the group consisting of SEQ ID NO: 3, SEQ ID NO: 13, and SEQ ID NO: 21 and combinations thereof.

18. The composition of claim 17, wherein the two or more elephant p53 proteins are encoded by retrogenes.

19. The composition of claim 17, wherein at least one of the two or more elephant p53 proteins is an ancestral p53 protein.

20. The composition of claim 1, wherein one or more of the elephant p53 proteins comprise an amino acid sequence of SEQ ID NO: 3.

21. The composition of claim 1, wherein the one or more nucleic acids are provided in an expression vector.

22. The composition of claim 1, wherein the one or more nucleic acids are recombinant.

23. The composition of claim 1, wherein the one or more elephant p53 proteins are recombinant.

* * * * *

SEQUENCE LISTING

```
<160> NUMBER OF SEQ ID NOS: 77

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
```

210 215 220

Val Gly Ser Asp Cys Thr Thr Ile His Tyr Asn Tyr Met Cys Asn Ser
225 230 235 240

Ser Cys Met Gly Gly Met Asn Arg Arg Pro Ile Leu Thr Ile Ile Thr
245 250 255

Leu Glu Asp Ser Ser Gly Asn Leu Leu Gly Arg Asn Ser Phe Glu Val
260 265 270

Arg Val Cys Ala Cys Pro Gly Arg Asp Arg Arg Thr Glu Glu Glu Asn
275 280 285

Leu Arg Lys Lys Gly Glu Pro His His Glu Leu Pro Pro Gly Ser Thr
290 295 300

Lys Arg Ala Leu Pro Asn Asn Thr Ser Ser Ser Pro Gln Pro Lys Lys
305 310 315 320

Lys Pro Leu Asp Gly Glu Tyr Phe Thr Leu Gln Ile Arg Gly Arg Glu
325 330 335

Arg Phe Glu Met Phe Arg Glu Leu Asn Glu Ala Leu Glu Leu Lys Asp
340 345 350

Ala Gln Ala Gly Lys Glu Pro Gly Gly Ser Arg Ala His Ser Ser His
355 360 365

Leu Lys Ser Lys Lys Gly Gln Ser Thr Ser Arg His Lys Lys Leu Met
370 375 380

Phe Lys Thr Glu Gly Pro Asp Ser Asp
385 390

<210> SEQ ID NO 2
<211> LENGTH: 1173
<212> TYPE: DNA
<213> ORGANISM: Loxodonta africana

<400> SEQUENCE: 2
atggaggagc cccagtcaga tctcagcacc gagctccctc tgagtcaaga gacgttttca 60
tacttatggg aactccttcc tgagaatccg gttctgtccc ccacactacc cccggcagtg 120
gaggtcatgg acgatctgct actctcagaa gacactgcaa actggctaga aagccaagtg 180
gaggctcagg gaatgtccac aacccctgca ccagccaccc ctacaccggt ggcccccgca 240
ccagccacct cctggaccct gtcatcttcc gtcccttccc aaaagaccta ccctggcacc 300
tatggtttcc gtctgggctt cctacattct gggacagcca agtccgtcac ctgcacgtac 360
tcccctgacc ttaacaagct gttttgccag ctggcaaaaa cctgcccagt gcagctgtgg 420
gtcgcctcac cacccccgcc cggcacccgt gttcgcacca tggccatcta caagaagtca 480
gagcatatga cggaggtcgt caagcgctgc ccccaccatg agcgctgctc tgactctagc 540
gatggcctgg cccctcctca gcacctcatc cgggtggaag gaaacctgcg tgctgagtat 600
ctggaggaca gcatcactct ccgacacagt gtggtggtgc cctacgagcc gcccgaggtc 660
gggtctgact gtaccaccat ccacttcaac ttcatgtgta acagctcctg catggggggc 720
atgaaccggc ggcccatcct caccatcatc acactggaag actccagtgg taatctgctg 780
ggacgtaaca gctttgaggt gcgcatttgt gcctgtcctg gaagagacag acgtacagaa 840
gaagaaaatt tccacaagaa gggagagcct tgcccagagc cgccaccccc tgggaggagc 900
actaagcgag cactgcccac caacaccagc tcctctaccc agccaaagaa gaagccactg 960
gatgaagaat atttcaccct tcagatccgt gggcgtgaac gcttcaagat gttcctagag 1020
ctaaatgagg ccttggagct gaaggatgcc caggctggga aggagccaga ggggagccgg 1080

-continued

```
gctcactcca gcccttcgaa gtctaagaag ggacagtcta cctcccgcca taaaaaacca   1140

atgttcaaga gagagggacc tgactcagac tga                                1173


<210> SEQ ID NO 3
<211> LENGTH: 390
<212> TYPE: PRT
<213> ORGANISM: Loxodonta africana

<400> SEQUENCE: 3

Met Glu Glu Pro Gln Ser Asp Leu Ser Thr Glu Leu Pro Leu Ser Gln
1               5                   10                  15

Glu Thr Phe Ser Tyr Leu Trp Glu Leu Leu Pro Glu Asn Pro Val Leu
            20                  25                  30

Ser Pro Thr Leu Pro Pro Ala Val Glu Val Met Asp Asp Leu Leu Leu
        35                  40                  45

Ser Glu Asp Thr Ala Asn Trp Leu Glu Ser Gln Val Glu Ala Gln Gly
    50                  55                  60

Met Ser Thr Thr Pro Ala Pro Ala Thr Pro Thr Pro Val Ala Pro Ala
65                  70                  75                  80

Pro Ala Thr Ser Trp Thr Leu Ser Ser Ser Val Pro Ser Gln Lys Thr
                85                  90                  95

Tyr Pro Gly Thr Tyr Gly Phe Arg Leu Gly Phe Leu His Ser Gly Thr
            100                 105                 110

Ala Lys Ser Val Thr Cys Thr Tyr Ser Pro Asp Leu Asn Lys Leu Phe
        115                 120                 125

Cys Gln Leu Ala Lys Thr Cys Pro Val Gln Leu Trp Val Ala Ser Pro
    130                 135                 140

Pro Pro Pro Gly Thr Arg Val Arg Thr Met Ala Ile Tyr Lys Lys Ser
145                 150                 155                 160

Glu His Met Thr Glu Val Val Lys Arg Cys Pro His His Glu Arg Cys
                165                 170                 175

Ser Asp Ser Ser Asp Gly Leu Ala Pro Pro Gln His Leu Ile Arg Val
            180                 185                 190

Glu Gly Asn Leu Arg Ala Glu Tyr Leu Glu Asp Ser Ile Thr Leu Arg
        195                 200                 205

His Ser Val Val Val Pro Tyr Glu Pro Pro Glu Val Gly Ser Asp Cys
    210                 215                 220

Thr Thr Ile His Phe Asn Phe Met Cys Asn Ser Ser Cys Met Gly Gly
225                 230                 235                 240

Met Asn Arg Arg Pro Ile Leu Thr Ile Ile Thr Leu Glu Asp Ser Ser
                245                 250                 255

Gly Asn Leu Leu Gly Arg Asn Ser Phe Glu Val Arg Ile Cys Ala Cys
            260                 265                 270

Pro Gly Arg Asp Arg Arg Thr Glu Glu Glu Asn Phe His Lys Lys Gly
        275                 280                 285

Glu Pro Cys Pro Glu Pro Pro Pro Pro Gly Arg Ser Thr Lys Arg Ala
    290                 295                 300

Leu Pro Thr Asn Thr Ser Ser Ser Thr Gln Pro Lys Lys Lys Pro Leu
305                 310                 315                 320

Asp Glu Glu Tyr Phe Thr Leu Gln Ile Arg Gly Arg Glu Arg Phe Lys
                325                 330                 335

Met Phe Leu Glu Leu Asn Glu Ala Leu Glu Leu Lys Asp Ala Gln Ala
            340                 345                 350

Gly Lys Glu Pro Glu Gly Ser Arg Ala His Ser Ser Pro Ser Lys Ser
```

```
        355                 360                 365

Lys Lys Gly Gln Ser Thr Ser Arg His Lys Lys Pro Met Phe Lys Arg
    370                 375                 380

Glu Gly Pro Asp Ser Asp
385                 390


<210> SEQ ID NO 4
<211> LENGTH: 1129
<212> TYPE: DNA
<213> ORGANISM: Loxodonta africana

<400> SEQUENCE: 4

atggaggagc ccgagtcaga tctcagtact gagctccctc tgagtcaaga gactttttg      60

tacttgggga aactccttcc tgagaagctg gttctgtccc cctcactgtc cccagcagcg    120

gaggcaggag acgatctgct actcccagaa gatgctgcag actggctaga aagccaagct    180

ggggctcaag aaacatcagc agcccctgca ccagccaccc ttataccagc ctcctcctgg    240

acactctcgt cctctgtccc ttcccagaag acctactgca gcaactgtgg tttccgtctt    300

ggcttcctgc attctgggac agccaagtct gtcacctgca tgtactcccc tgaccttaac    360

aagctgtttt gccagctggc aaagacctgt ccagtgcagc cgtagctcag ctcaccaccc    420

caccccagca cctgtgttca caccatggcc atctaccaga cgtcagcata tgacagaggt    480

catgcagcac tgcccccacc ttgagtgctg ctctgactat agcgacggcc tggccgctcc    540

tcagcatctt atccaggtgg gagaaatcct gtgtgctgat atttgtagga caccatcact    600

ctttgacata gtgtggggta ccctatgagc tacctcaggt cggctctgac taccaccatc    660

cacttcaact tcatgtgtag cagctcctgc aagggggga ggaacccatc ctcaccatca    720

tcacactgga agactccagt ggtaatctgc taggacacaa cagtttcgaa gtgcatattt    780

gtacctgttc tgggagagac agacgtacag aggaagaaaa tttccacaac aagtgggagc    840

caccctctga gaggatcact aagtaagcac tgccaccagc actagctccc ctaccgagcc    900

aaagaagaag ccagtggatg aaaaatattt cacccttcag atccatgggc atgaatgatt    960

caagatattc ctagagttga atgaggcact ggagctgaag gatgcccagg ctgggaagca   1020

gccagagggg agcagggctc aatgcagcct tccaaactct aagaaagggg aatctaccac   1080

ccactgtaaa aaactaatgt tcaagagaga ggggcctgac tcagactga               1129


<210> SEQ ID NO 5
<211> LENGTH: 361
<212> TYPE: PRT
<213> ORGANISM: Loxodonta africana

<400> SEQUENCE: 5

Met Glu Glu Pro Glu Ser Asp Leu Ser Thr Glu Leu Pro Leu Ser Gln
1               5                   10                  15

Glu Thr Phe Leu Tyr Leu Gly Lys Leu Leu Pro Glu Lys Leu Val Leu
            20                  25                  30

Ser Pro Ser Leu Ser Pro Ala Ala Glu Ala Gly Asp Asp Leu Leu Leu
        35                  40                  45

Pro Glu Asp Ala Ala Asp Trp Leu Glu Ser Gln Ala Gly Ala Gln Glu
    50                  55                  60

Thr Ser Ala Ala Pro Ala Pro Ala Thr Leu Ile Pro Ala Ser Ser Trp
65                  70                  75                  80

Thr Leu Ser Ser Ser Val Pro Ser Gln Lys Thr Tyr Cys Ser Asn Cys
                85                  90                  95
```

```
Gly Phe Arg Leu Gly Phe Leu His Ser Gly Thr Ala Lys Ser Val Thr
            100                 105                 110

Cys Met Tyr Ser Pro Asp Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Thr Ser Ala Tyr Asp Arg Gly His
145                 150                 155                 160

Ala Ala Leu Pro Pro Pro Val Leu Leu Leu Arg Arg Pro Gly Arg Ser
                165                 170                 175

Ser Ala Ser Tyr Pro Gly Gly Arg Asn Pro Val Cys Tyr Leu Asp Thr
            180                 185                 190

Ile Thr Leu His Ser Val Gly Tyr Pro Met Ser Tyr Leu Arg Ser Ala
        195                 200                 205

Leu Thr Thr Thr Ile His Phe Asn Phe Met Cys Ser Ser Ser Cys Lys
    210                 215                 220

Gly Gly Arg Asn Pro Ser Ser Pro Ser Ser His Trp Lys Thr Pro Val
225                 230                 235                 240

Val Ile Cys Asp Thr Thr Val Ser Lys Cys Ile Phe Val Pro Val Leu
                245                 250                 255

Gly Glu Thr Asp Val Gln Arg Lys Lys Ile Ser Thr Thr Ser Gly Ser
            260                 265                 270

His Pro Leu Arg Gly Ser Leu Ser Lys His Cys His Gln His Leu Pro
        275                 280                 285

Tyr Arg Ala Lys Glu Glu Ala Ser Gly Lys Ile Phe His Pro Ser Asp
    290                 295                 300

Pro Trp Ala Met Ile Gln Asp Ile Pro Arg Val Glu Gly Thr Gly Ala
305                 310                 315                 320

Glu Gly Cys Pro Gly Trp Glu Ala Ala Arg Gly Glu Gln Gly Ser Met
                325                 330                 335

Gln Pro Ser Lys Leu Glu Arg Gly Ile Tyr His Pro Leu Lys Thr Asn
            340                 345                 350

Val Gln Glu Arg Gly Ala Leu Arg Leu
        355                 360


<210> SEQ ID NO 6
<211> LENGTH: 1136
<212> TYPE: DNA
<213> ORGANISM: Loxodonta africana

<400> SEQUENCE: 6

atggaggagc ccgagtcaga tctcagtact gagctccttc tgagtcaaga gactttttcg      60

tacttgggga aactccttcc tgagaagctg gttctgtccc cctcactgtc cccagcagcg     120

gaggcagtag acgatctgct actcccagaa gatgctgcag actggctaga aagccaagct     180

ggggctcaag gaatatcagc agcccctgca ccagccaccc ttacaccagc cacctcctag     240

acactttcat cctctgtccc ttcccagaag acctactgca gcaactgtgg tttccatctt     300

ggcttcctgc attctgggac agccaagtct gtcacctgca cgtactcccc tgaccttaac     360

aagctgttct gccagctggc aaagacctgt ccagtgcagc cgtagctcag ctcaccaccc     420

cactccaccc cagcacctgt gttcacacca tggccatcta ccagatgtca gcacatgaca     480

gaggtcgtgc agcactgccc ccatcttgag tgctactccg actatagcga tggcctggcc     540

gctcctcagc atcttatcca ggtgggagga atcctgcgtg ctgatatttg taggacacca     600
```

```
ttactcttcg acatagtgtg gggtacccta tgagctacct caggtcggtt ctgactacca    660

ccatccactt caacttcatg tgtagcagct cctgcatggg gggggggaac ccatcctcac    720

catcatcaca ctggaagact ccgatggtaa tctgctagga cacaacagtt tcgaggtgca    780

tatttgtact gttctgggag agacagacgt acagaggaag aaaattttcc acaacaagtg    840

gggagccagc ctctgagagg atcactgagt aagcactgcc caccagcacc agctcctcta    900

ccgagccaaa gaagaagcca gtggacgaaa aatatttcac ccttaagatc catgggcatg    960

aatgcttcaa gatgttccta gagttgaacg aggcattgga gctgaaggat gcccaggctg   1020

ggaagcagtc agaggggagc agggatcaat gcagccttcc aaactctagg aaaggggaat   1080

ctaccaccca ctgtaaaaaa ctaatgttca agagagaggg gcctgactca gactga       1136
```

<210> SEQ ID NO 7
<211> LENGTH: 369
<212> TYPE: PRT
<213> ORGANISM: Loxodonta africana

<400> SEQUENCE: 7

```
Met Glu Glu Pro Glu Ser Asp Leu Ser Thr Glu Leu Leu Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Ala Ala Pro Ala Pro Ala Thr Leu Thr Pro Ala Thr Ser Thr
65                  70                  75                  80

Leu Ser Ser Ser Val Pro Ser Gln Lys Thr Tyr Cys Ser Asn Cys Gly
                85                  90                  95

Phe His Leu Gly Phe Leu His Ser Gly Thr Ala Lys Ser Val Thr Cys
            100                 105                 110

Thr Tyr Ser Pro Asp Leu Asn Lys Leu Phe Cys Gln Leu Ala Lys Thr
        115                 120                 125

Cys Pro Val Gln Pro Leu Ser Ser Pro Pro His Ser Thr Pro Ala Pro
    130                 135                 140

Val Phe Thr Pro Trp Pro Ser Thr Arg Cys Gln His Met Thr Glu Val
145                 150                 155                 160

Val Gln His Cys Pro His Leu Glu Cys Tyr Ser Asp Tyr Ser Asp Gly
                165                 170                 175

Leu Ala Ala Pro Gln His Leu Ile Gln Val Gly Gly Ile Leu Arg Ala
            180                 185                 190

Asp Ile Cys Arg Thr Pro Leu Leu Phe Asp Ile Val Trp Gly Thr Leu
        195                 200                 205

Ala Thr Ser Gly Arg Phe Leu Pro Pro Ser Thr Ser Thr Ser Cys Val
    210                 215                 220

Ala Ala Pro Ala Trp Gly Gly Gly Thr His Pro His His His His Thr
225                 230                 235                 240

Gly Arg Leu Arg Trp Ser Ala Arg Thr Gln Gln Phe Arg Gly Ala Tyr
                245                 250                 255

Leu Tyr Cys Ser Gly Arg Asp Arg Arg Thr Glu Glu Glu Asn Phe Pro
            260                 265                 270

Gln Gln Val Gly Ser Gln Pro Leu Arg Gly Ser Leu Ser Lys His Cys
```

```
        275                 280                 285

Pro Pro Ala Pro Ala Pro Leu Pro Ser Gln Arg Arg Ser Gln Trp Thr
    290                 295                 300

Lys Asn Ile Ser Pro Leu Arg Ser Met Gly Met Asn Ala Ser Arg Cys
305                 310                 315                 320

Ser Ser Thr Arg His Trp Ser Arg Met Pro Arg Leu Gly Ser Ser Gln
                325                 330                 335

Arg Gly Ala Gly Ile Asn Ala Ala Phe Gln Thr Leu Gly Lys Gly Asn
            340                 345                 350

Leu Pro Pro Thr Val Lys Asn Cys Ser Arg Glu Arg Gly Leu Thr Gln
        355                 360                 365

Thr


<210> SEQ ID NO 8
<211> LENGTH: 1130
<212> TYPE: DNA
<213> ORGANISM: Loxodonta africana

<400> SEQUENCE: 8

atggaggagc ctcagtcaga tctcagtact gagctccctc tgagtcaaga gactttttca      60

tgcttgggga aactccttcc tgagaagctg gttctgtccc cctcactgtc cccagcagcg     120

gaggcagtag acgatctgct actcccagaa gatgctgcag actgcctaga aagccaagct     180

ggggctcaag gaatatcagc agcccctgca ccagccaccc ttacaccagc caccgcctgg     240

acactctcat cctctgtccc ttcccagaag acctactgca gcaactgtgg tttccgtctt     300

ggcttcctgc attctgggac agccaagtct gtcacctgca tgtactcccc tggccttaac     360

aagctgtttt gccagctggc aaagacctgt ccagtgcaac cgtagctcag ctcaccaccc     420

caccccagca cctgtgttca caccatggcc atctaccaga tgtcagcata tgacagaggt     480

cgtgcagcac tgcccccacc ttgagtgctg ctccgactat agcgatggcc tggccgctcc     540

tcagcatctt atccaggtgg gaggaatcct gcgtgctgat atttgtagga caccatcact     600

cttcgacata gtgtggggta tcctatgagc tacctcaggt cggttctgac taccaccatc     660

cacttcaact tcatgtgtag cagctcctgc atggggcggg gcgaacccat cctcaccatc     720

atcacactgg aagactccga tggtaatctg ctaggacaca acagtttcga ggtgcatatt     780

tgtactgttc tgggagagac agacgtacag aggaagaaaa tttccacaac aagtgggagc     840

caccctctga gaggatcact aagtaagcac tgcgcaccag caccagctcc tctaccgagc     900

caaagaagaa gccagtggat gaaaaatatt tcacccttaa gatccgtggg catgaatgct     960

tcaagatgtt cctagagttg aatgaggcat tggagctgaa ggatgcccag gctgggaagc    1020

agccagaagg gagcagggct caatgcagcc ttccaaactc taagaaaggg gaatctacca    1080

cccactgtaa aaaactaatg ttcaagagag aggggcctga ctcagactga               1130


<210> SEQ ID NO 9
<211> LENGTH: 367
<212> TYPE: PRT
<213> ORGANISM: Loxodonta africana

<400> SEQUENCE: 9

Met Glu Glu Pro Gln Ser Asp Leu Ser Thr Glu Leu Pro Leu Ser Gln
1               5                   10                  15

Glu Thr Phe Ser Cys Leu Gly Lys Leu Leu Pro Glu Lys Leu Val Leu
            20                  25                  30
```

```
Ser Pro Ser Leu Ser Pro Ala Ala Glu Ala Val Asp Asp Leu Leu Leu
        35                  40                  45

Pro Glu Asp Ala Ala Asp Cys Leu Glu Ser Gln Ala Gly Ala Gln Gly
    50                  55                  60

Ile Ser Ala Ala Pro Ala Pro Ala Thr Leu Thr Pro Ala Thr Ala Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Met Ser Ala Tyr Asp Arg Gly Arg
145                 150                 155                 160

Ala Ala Leu Pro Pro Pro Val Leu Leu Arg Leu Arg Trp Pro Gly Arg
                165                 170                 175

Ser Ser Ala Ser Tyr Pro Gly Gly Arg Asn Pro Ala Cys Tyr Leu Asp
            180                 185                 190

Thr Ile Thr Leu Arg His Ser Val Gly Tyr Pro Met Ser Tyr Leu Arg
        195                 200                 205

Ser Val Leu Thr Thr Thr Ile His Phe Asn Phe Met Cys Ser Ser Ser
    210                 215                 220

Cys Met Gly Arg Gly Glu Pro Ile Leu Thr Ile Ile Thr Leu Glu Asp
225                 230                 235                 240

Ser Asp Gly Asn Leu Leu Gly His Asn Ser Phe Glu Val His Ile Cys
                245                 250                 255

Thr Val Leu Gly Glu Thr Asp Val Gln Arg Lys Lys Ile Ser Thr Thr
            260                 265                 270

Ser Gly Ser His Pro Leu Arg Gly Ser Leu Ser Lys His Cys Ala Pro
        275                 280                 285

Ala Pro Ala Pro Leu Pro Ser Gln Arg Arg Ser Gln Trp Met Lys Asn
    290                 295                 300

Ile Ser Pro Leu Arg Ser Val Gly Met Asn Ala Ser Arg Cys Ser Ser
305                 310                 315                 320

Met Arg His Trp Ser Arg Met Pro Arg Leu Gly Ser Ser Gln Lys Gly
                325                 330                 335

Ala Gly Leu Asn Ala Ala Phe Gln Thr Leu Arg Lys Gly Asn Leu Pro
            340                 345                 350

Pro Thr Val Lys Asn Cys Ser Arg Glu Arg Gly Leu Thr Gln Thr
        355                 360                 365


<210> SEQ ID NO 10
<211> LENGTH: 1130
<212> TYPE: DNA
<213> ORGANISM: Loxodonta africana

<400> SEQUENCE: 10

atggaggagg ctcagtcaga tctcagtact gagctccctc tgagtcaaga gactttttca      60

tgcttgggga aactccttcc tgagaaggtg gttctgtccc cctcactgtc cccagcagcg     120

gaggcagtag acgatctgct actcccagaa gatgctgcag actgcctaga aagccaagct     180

ggggctcaag gaatatcagc agcccctgca ccagccaccc ttacaccagc cacctcctgg     240
```

```
acactctcat cctctgtccc ttcccagaag acctactgca gcaactgtgg tttccgtctt    300

ggcttcctgc attctgggac agccaagtct gtcacctgca tgtactcccc tggccttaac    360

aagctgtttt gccagctggc aaagacctgt ccagtgcagc cgtagctcac ctcaccagcc    420

caccccagca cctgtgttca caccatggcc atctaccaga tgtcagcata tgacagaggt    480

cgtgcagcac tgcccccacc ttgagtgctg ctccgactat agcgatggcc tggccgctcc    540

tcagcatctt atccaggtgg gaggaatcct gcgtgctgat atttgtagga caccatcact    600

cttcgacata gtgtggggta tcctatgagc tacctcaggt cggttctgac taccaccatc    660

cacttcaact tcatgtgtag cagctcctgc atggggcggg gggaacccat cctcaccatc    720

atcacactgg aagactccga tggtaatctg ctaggacaca acagtttcga ggtgcatatt    780

tgtactgttc tgggagagac agacgtacag aggaagaaaa tttccacaac aagtgggagc    840

caccctctga gaggatcact aagtaagcac tgcccaccag caccagctcc tctaccgagc    900

caaagaagaa gccagcggat gaaaaatatt tcacccttaa gatccgtggg catgaatgct    960

tcaagatgtt cctagagttg aatgaggcat tggagctgaa ggatgcccag gctgggaagc   1020

agccagaagg gagcagggct cgatgcagcc ttccaaactc taagaaaggg gaatctacca   1080

cccactgtaa aaaactaatg ttcaagagag aggggcctga ctcagactga              1130
```

<210> SEQ ID NO 11
<211> LENGTH: 367
<212> TYPE: PRT
<213> ORGANISM: Loxodonta africana

<400> SEQUENCE: 11

```
Met Glu Glu Ala Gln Ser Asp Leu Ser Thr Glu Leu Pro Leu Ser Gln
1               5                   10                  15

Glu Thr Phe Ser Cys Leu Gly Lys Leu Leu Pro Glu Lys Val Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Cys Leu Glu Ser Gln Ala Gly Ala Gln Gly
    50                  55                  60

Ile Ser Ala Ala Pro Ala Pro Ala Thr Leu Thr Pro Ala Thr Ser Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Thr Ser Pro Ala His Pro Ser Thr Cys
    130                 135                 140

Val His Thr Met Ala Ile Tyr Gln Met Ser Ala Tyr Asp Arg Gly Arg
145                 150                 155                 160

Ala Ala Leu Pro Pro Pro Val Leu Leu Arg Leu Arg Trp Pro Gly Arg
                165                 170                 175

Ser Ser Ala Ser Tyr Pro Gly Gly Arg Asn Pro Ala Cys Tyr Leu Asp
            180                 185                 190

Thr Ile Thr Leu Arg His Ser Val Gly Tyr Pro Met Ser Tyr Leu Arg
        195                 200                 205

Ser Val Leu Thr Thr Thr Ile His Phe Asn Phe Met Cys Ser Ser Ser
    210                 215                 220
```

```
Cys Met Gly Arg Gly Glu Pro Ile Leu Thr Ile Ile Thr Leu Glu Asp
225                 230                 235                 240

Ser Asp Gly Asn Leu Leu Gly His Asn Ser Phe Glu Val His Ile Cys
                245                 250                 255

Thr Val Leu Gly Glu Thr Asp Val Gln Arg Lys Lys Ile Ser Thr Thr
            260                 265                 270

Ser Gly Ser His Pro Leu Arg Gly Ser Leu Ser Lys His Cys Pro Pro
        275                 280                 285

Ala Pro Ala Pro Leu Pro Ser Gln Arg Arg Ser Gln Arg Met Lys Asn
    290                 295                 300

Ile Ser Pro Leu Arg Ser Val Gly Met Asn Ala Ser Arg Cys Ser Ser
305                 310                 315                 320

Met Arg His Trp Ser Arg Met Pro Arg Leu Gly Ser Ser Gln Lys Gly
                325                 330                 335

Ala Gly Leu Asp Ala Ala Phe Gln Thr Leu Arg Lys Gly Asn Leu Pro
            340                 345                 350

Pro Thr Val Lys Asn Cys Ser Arg Glu Arg Gly Leu Thr Gln Thr
        355                 360                 365
```

<210> SEQ ID NO 12
<211> LENGTH: 1129
<212> TYPE: DNA
<213> ORGANISM: Loxodonta africana

<400> SEQUENCE: 12

```
atggaggagc ccaagtcaga tctcagtact gagctccctc tgagtcaaga gactttttca     60

tacttgggga aactccttcc tgagaagctg gttctgtccc cctcactgtc cccagcagcg    120

gaggcagtag acgatctgct gctcccagaa gatgctgcag actgcctaga aagccaagct    180

ggggctcaag aaatatcagc agcccctgca ccagccacac ttacaccagc cacctcctgg    240

acactctcat cctctgtccc ttcccagaag acctactgca gcaactgtgg tttccgtctt    300

ggcttcctgc attctgggac agccaagtct gtcacctgca tgtactcccc tggccttaac    360

aagctgtttt gccagctggc aaagacctgt ccagtgcagc cgtagctcag ctcaccaccc    420

caccccagca cctgtgttca caccatggcc atctaccaga tgtcagcata tgacagaggt    480

cgtgcagcac tgcccccacc ttgagtgctg ctctgactat accgatggcc tggccgctcc    540

tcagcatctt atccaggtgg gaggaatcct gcgtgctgat atttgtagga caccatcact    600

cttcaacata gtgtggggta ccctatgagc tacctcaggt cggttctgac taccaccatc    660

cacttcaact tcatgtgtag caggctcctg catggggggg ggaacccatc ctcaccatca    720

tcacactgga agactccgat ggtaatctgc taggacacaa cagtttcgag gtgcatattt    780

gtactgttct gggagagaca gatgtacaga ggaagaaaat ttccacaaca agtgggagcc    840

accctctgag aggatcacta agtaagcact gcacaccagc accagctcct ctactgagcc    900

aaagaagaag ccagtggatg aaaaatattt cacccttaag atccgtgggc atgaatgttt    960

caagatgttc ctagagttga atgaggcatt ggagctgaag gatgcccagg ctgggaagca   1020

gccagagggg agcagggctc aatgcagcct tccaaactct aagaaagggg aatctaccac   1080

ccactgtaaa aaactaatgt tcaagagaga ggggcctgac tcagactga               1129
```

<210> SEQ ID NO 13
<211> LENGTH: 360
<212> TYPE: PRT
<213> ORGANISM: Loxodonta africana

<400> SEQUENCE: 13

```
Met Glu Glu Pro Lys Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Cys Leu Glu Ser Gln Ala Gly Ala Gln Glu
    50                  55                  60

Ile Ser Ala Ala Pro Ala Pro Ala Thr Leu Thr Pro Ala Thr Ser Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Met Ser Ala Tyr Asp Arg Gly Arg
145                 150                 155                 160

Ala Ala Leu Pro Pro Pro Val Leu Leu Leu Tyr Arg Trp Pro Gly Arg
                165                 170                 175

Ser Ser Ala Ser Tyr Pro Gly Gly Arg Asn Pro Ala Cys Tyr Leu Asp
            180                 185                 190

Thr Ile Thr Leu Gln His Ser Val Gly Tyr Pro Met Ser Tyr Leu Arg
        195                 200                 205

Ser Val Leu Thr Thr Thr Ile His Phe Asn Phe Met Cys Ser Arg Leu
    210                 215                 220

Leu His Gly Gly Gly Asn Pro Ser Ser Pro Ser Ser His Trp Lys Thr
225                 230                 235                 240

Pro Met Val Ile Cys Asp Thr Thr Val Ser Arg Cys Ile Phe Val Leu
                245                 250                 255

Phe Trp Glu Arg Gln Met Tyr Arg Gly Arg Lys Phe Pro Gln Gln Val
            260                 265                 270

Gly Ala Thr Leu Glu Asp His Val Ser Thr Ala His Gln His Gln Leu
        275                 280                 285

Leu Tyr Ala Lys Glu Glu Ala Ser Gly Lys Ile Phe His Pro Asp Pro
    290                 295                 300

Trp Ala Met Phe Gln Asp Val Pro Arg Val Glu Gly Ile Gly Ala Glu
305                 310                 315                 320

Gly Cys Pro Gly Trp Glu Ala Ala Arg Gly Glu Gln Gly Ser Met Gln
                325                 330                 335

Pro Ser Lys Leu Glu Arg Gly Ile Tyr His Pro Leu Lys Thr Asn Val
            340                 345                 350

Gln Glu Arg Gly Ala Leu Arg Leu
        355                 360
```

<210> SEQ ID NO 14
<211> LENGTH: 1129
<212> TYPE: DNA
<213> ORGANISM: Loxodonta africana

<400> SEQUENCE: 14

```
atggaggagc ccaagtcaga tctcagtact gagctccctc tgagtcaaga gactttttca     60
tacttgggga aactccttcc tgagaagctg gttctgtccc cctcactgtc cccagcagcg    120
gaggcagtag acgatctgct gctcccagga gatgctgcag actgcctaga aagccaagct    180
ggggctcaag gaatatcagc agcccctgca ccagccaccc ttacaccagc cacctcctgg    240
acactctcat cctctgtccc ttcccagaag acctactgca gcaactgtgg tttccgtctt    300
ggcttcctgc attctgggac agccaagtct gtcacctgca tgtactcccc tggccttaac    360
aagctgtttt gccagctggc aaagacctgt ccagtgcagc cgtagctcag ctcaccaccc    420
caccccagca cctgtgttca caccatggcc atctaccaga cgtcagcata tgacagaggt    480
ggtgcagcac tgcccccacc ttgagtgctg ctccgactat agcgatggcc tggccgctcc    540
tcagcatctt atccaggtgg gaggaatcct gcgtgctgat atttgtagga caccatcact    600
cttcgacata gtgtggggta ccctatgagc tacctcaggt cggttctgac taccaccatc    660
cacttcaact tcatgtgtag cagctcctgc gtgggggcgg gaaacccatc ctcaccatca    720
tcacactgga agactccgat ggtaatctgc taggacacaa cagtttcgag gtgcatattt    780
gtactgttct gggagagaca gacgtacaga ggaagaaaat ttccacaaca agtgggagcc    840
accctctgag aggatcacta agtaagcact gcacaccagc accagctcct ctaccgagcc    900
aaagaagaag ccagtggatg aaaaatattt cacccttaag atccgtgggc atgaatgctt    960
caagatgttc ctagagttga atgaggcatt ggagctgaag gatgcccagg ctgggaagca   1020
gccagagggg agcagggctc aatgcagcct tccaaactct aagaaagggg aatctaccac   1080
ccactgtaaa aaactaatgt tcaagagaga ggggcctgac tcagactga               1129
```

<210> SEQ ID NO 15
<211> LENGTH: 361
<212> TYPE: PRT
<213> ORGANISM: Loxodonta africana

<400> SEQUENCE: 15

```
Met Glu Glu Pro Lys Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Gly Asp Ala Ala Asp Cys Leu Glu Ser Gln Ala Gly Ala Gln Gly
    50                  55                  60

Ile Ser Ala Ala Pro Ala Pro Ala Thr Leu Thr Pro Ala Thr Ser Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Thr Ser Ala Tyr Asp Arg Gly Gly
145                 150                 155                 160

Ala Ala Leu Pro Pro Pro Val Leu Leu Arg Leu Arg Trp Pro Gly Arg
                165                 170                 175
```

```
Ser Ser Ala Ser Tyr Pro Gly Gly Arg Asn Pro Ala Cys Tyr Leu Asp
            180                 185                 190

Thr Ile Thr Leu Arg His Ser Val Gly Tyr Pro Met Ser Tyr Leu Arg
        195                 200                 205

Ser Val Leu Thr Thr Thr Ile His Phe Asn Phe Met Cys Ser Ser Ser
    210                 215                 220

Cys Val Gly Ala Gly Asn Pro Ser Ser Pro Ser Ser His Trp Lys Thr
225                 230                 235                 240

Pro Met Val Ile Cys Asp Thr Thr Val Ser Arg Cys Ile Phe Val Leu
                245                 250                 255

Phe Trp Glu Arg Gln Thr Tyr Arg Gly Arg Lys Phe Pro Gln Gln Val
            260                 265                 270

Gly Ala Thr Leu Glu Asp His Val Ser Thr Ala His Gln His Gln Leu
        275                 280                 285

Leu Tyr Arg Ala Lys Glu Glu Ala Ser Gly Lys Ile Phe His Pro Asp
    290                 295                 300

Pro Trp Ala Met Leu Gln Asp Val Pro Arg Val Glu Gly Ile Gly Ala
305                 310                 315                 320

Glu Gly Cys Pro Gly Trp Glu Ala Ala Arg Gly Glu Gln Gly Ser Met
                325                 330                 335

Gln Pro Ser Lys Leu Glu Arg Gly Ile Tyr His Pro Leu Lys Thr Asn
            340                 345                 350

Val Gln Glu Arg Gly Ala Leu Arg Leu
        355                 360
```

<210> SEQ ID NO 16
<211> LENGTH: 1129
<212> TYPE: DNA
<213> ORGANISM: Loxodonta africana

<400> SEQUENCE: 16

```
atggaggagc ctcagtcaga tctcagcact gagctccctc tgagtcaaga gacgttttca     60

tacttgggga aactccttcc tgagaagctg gttctgtccc cctcactgtc cccagaagcg    120

gaggcagtag acaatctgct actcccagaa gatgctgcag actggctaga aagccaagct    180

ggggctcaag gaatatcaga agcccctaca ctagccacct cctggatgct gtcatcctct    240

gtcccttctc agaagacctg cccagcacct atcgtttctg tctgggcttc ttgcattctg    300

ggacagccaa gtccgtcacc tacacatact cccctgaact taacatgctg ttttgccagc    360

tggcaaaggc ctgcccagtg cagctgtggg tcacctcaac acccccgccc agcacctgtg    420

ttcacaccat ggccatctac cagacgtcag catatgatgg aggtcatgaa gcactgccgc    480

caccttgagt gccgctctga ctatagcaat tgcttggacc ctcctcagca cctcatccag    540

tgggaggaaa cctgcatgct gagtatttgg aggacaccat cactctatga catagtgtgg    600

ggtgccctag tagccaccag aggtcggttc tgactaccac catccacttc aacttcatgt    660

gtaacagctc ctgcatgggg ggcaggaacc tatcctcacc atcatcacac tggaagactc    720

caacggtaat ccgctgggac acaacagttt cgaggtgcat atttgtacct gtcctgggag    780

acacagatgt acagaggaag acagtttcca caagaagtgg gagccttgcc ctgagccagc    840

ctctgggaag gatcactaag cgaacactgc ccaccagcac cagctcctct accaagccaa    900

agaagaagcc actggataaa aaatacttca cccttcagat ccatgggcat gaatgattca    960

agatgttcct aaagctcaac gaggccttgg agctgaagga tgcccaggct gggaggcagc   1020
```

```
cagaggggag cagggctcaa cccagccttc ccaagtctaa gaaaaggcaa tctacctcct   1080

gccataaaaa aaactaatgt tctagagaga gcagcctgac tcagactga               1129


<210> SEQ ID NO 17
<211> LENGTH: 370
<212> TYPE: PRT
<213> ORGANISM: Loxodonta africana

<400> SEQUENCE: 17

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Glu Ala Glu Ala Val Asp Asn Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Met Leu Ser Ser Ser
65                  70                  75                  80

Val Pro Ser Gln Lys Thr Cys Pro Ala Pro Ile Val Ser Val Trp Ala
                85                  90                  95

Ser Cys Ile Leu Gly Gln Pro Ser Pro Ser Pro Thr His Thr Pro Leu
            100                 105                 110

Asn Leu Thr Cys Cys Phe Ala Ser Trp Gln Arg Pro Ala Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Met Lys His Cys Arg
145                 150                 155                 160

His Leu Glu Cys Arg Ser Asp Tyr Ser Asn Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Val Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr Tyr Pro His His His His Thr Gly Arg Leu Gln
225                 230                 235                 240

Arg Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Gln Glu Val Gly
            260                 265                 270

Ala Leu Pro Ala Ser Leu Trp Glu Gly Ser Leu Ser Glu His Cys Pro
        275                 280                 285

Pro Ala Pro Ala Pro Leu Pro Ser Gln Arg Arg Ser His Trp Ile Lys
    290                 295                 300

Asn Thr Ser Pro Phe Arg Ser Met Gly Met Asn Asp Ser Arg Cys Ser
305                 310                 315                 320

Ser Ser Thr Arg Pro Trp Ser Arg Met Pro Arg Leu Gly Gly Ser Gln
                325                 330                 335

Arg Gly Ala Gly Leu Asn Pro Ala Phe Pro Ser Leu Arg Lys Gly Asn
            340                 345                 350

Leu Pro Pro Ala Ile Lys Lys Thr Asn Val Leu Glu Arg Ala Ala Leu
```

```
        355                 360                 365

Arg Leu
    370


<210> SEQ ID NO 18
<211> LENGTH: 1126
<212> TYPE: DNA
<213> ORGANISM: Loxodonta africana

<400> SEQUENCE: 18

atggaggagc ctctgtcaga tctcagcact gagctccctc tgagtcaaga gacgttttca      60

tacttgggga aactccttcc tgagaagctg gttctgtccc cctcactgtc cccagcagcg     120

gaggcagtag acgatctgct actcccagaa gatgctgcag actggctaga aagccaagct     180

ggggctcaag gaatatcaga agcccctaca ctagccacct cctggacgct gtcatcctct     240

gtcccttctc aaaagaccta cccagcacct atcgtttctg tctgggcttc ttgcattctg     300

ggacagccaa gtctgtcacc tacacgtact cccctgaact taacatgctg ttttgccagc     360

tggcaaaggc ctgtccagtg cagccgtggg tcacctcaac aaccccgccc agcacctgtg     420

ttcacaccat ggccatctac cagacgtcag catatgatgg aggtcgtgaa gcactgcccc     480

caccttgagt gccgctgtga ctatagcgat tgcttggacc ctcctcagca cctcatccag     540

tgggaggaaa cctgcatgct gagtatttgg aggacaccat cactctatga catagtgtgg     600

ggtgccctat gagccaccag aggtcggttc tgactaccac catccacttc aacttcatgt     660

gtaacagctc ctgcatgggg ggcaggaacc catcctcacc atcatcactc tggaatactc     720

caatggtaat ccgctgggac acaacagttt cgaggtgcat atttgtacct gtcctgggag     780

acacagatgt acagaggaag acaatttcca gaagaagtgg gagccttgcc ctgagccacc     840

ctctgggagg atcactaagc aaacactgcc caccagcacc agctcctcta tcaagccaaa     900

gaagaagcca ctggatgaaa aatacttcac ccttcagatc catgggcatg aatgtttcaa     960

gatgttccta aagctcaacg aggccttgga gctgaaggat gcccaggctg ggaagcaacc    1020

agggggggagc agggctcaat ccagccttcc caagtctaag aaaaggcaat ctatctccca    1080

ccataaaaaa ataatgttca agagagagca gcctgactca gactga                   1126


<210> SEQ ID NO 19
<211> LENGTH: 365
<212> TYPE: PRT
<213> ORGANISM: Loxodonta africana

<400> SEQUENCE: 19

Met Glu Glu Pro Leu Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Leu Ser Pro Thr Arg Thr Pro Leu
            100                 105                 110
```

```
Asn Leu Thr Cys Cys Phe Ala Ser Trp Gln Arg Pro Val Gln Cys Ser
        115                 120                 125

Arg Gly Ser Pro Gln Gln Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Cys Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Ala Thr Arg Gly Arg
        195                 200                 205

Phe Leu Pro Pro Ser Thr Ser Thr Ser Cys Val Thr Ala Pro Ala Trp
    210                 215                 220

Gly Ala Gly Thr His Pro His His His His Ser Gly Ile Leu Gln Trp
225                 230                 235                 240

Ser Ala Gly Thr Gln Gln Phe Arg Gly Ala Tyr Leu Tyr Leu Ser Trp
                245                 250                 255

Glu Thr Gln Met Tyr Arg Gly Arg Gln Phe Pro Glu Glu Val Gly Ala
            260                 265                 270

Leu Pro Ala Thr Leu Trp Glu Asp His Ala Asn Thr Ala His Gln His
        275                 280                 285

Gln Leu Leu Tyr Gln Ala Lys Glu Glu Ala Thr Gly Lys Ile Leu His
    290                 295                 300

Pro Ser Asp Pro Trp Ala Met Phe Gln Asp Val Pro Lys Ala Gln Arg
305                 310                 315                 320

Gly Leu Gly Ala Glu Gly Cys Pro Gly Trp Glu Ala Thr Arg Gly Glu
                325                 330                 335

Gln Gly Ser Ile Gln Pro Ser Gln Val Glu Lys Ala Ile Tyr Leu Pro
            340                 345                 350

Pro Lys Asn Asn Val Gln Glu Arg Ala Ala Leu Arg Leu
        355                 360                 365


<210> SEQ ID NO 20
<211> LENGTH: 1126
<212> TYPE: DNA
<213> ORGANISM: Loxodonta africana

<400> SEQUENCE: 20

atggaggagc ctcagtcaga tctcagcact gagctccctc tgagtcaaga gacattttca      60

tacttgggga aactccttcc tgagaagctg gttctgtccc cctcactgtc cccagcagcg     120

gaggcagtag atgatctgct actcccagaa gatgctgcag actggctaga aagccaagct     180

ggggctcaag gaatatcaga agcccctaca ctagccacct cctggacgct gtcatcctct     240

gtcccttctc agaagaccta cccagcacct atcgtttctg tctgggcttc ttgcattctg     300

ggacagccaa gtctgtcacc tacacgtact cccctgaact taacatgctg ttttgccggc     360

tggcaaaggc ctgtccagtg cagctgtggg tcacctcaac acccccgccc agcacctgtg     420

ttcacaccat ggccatctac cagacgtcag catatgatgg aggtcgtgaa gcactgcccc     480

caccttgagt gccgctgtga ctatagcgat tgcttggacc ctcctcagca cctcatccag     540

taggaggaaa cctgcatgct gagtatttgg aggacaccat cactctatga catagtgtgg     600

ggtgccctag gagccaccag aggtcggttc tgactaccac catccacttc aacttcatgt     660
```

```
gtaacagctc ctgcatgggg ggcatgaacc catcctcacc atcatcactc tggaatactc    720

caatggtaat ccgctgggac acaacagttt cgaggtgcat atttgtacct gtcctgggag    780

acacagatgt acagaggaag acaatttcca gaagaagtgg gagccttgcc ctgagccacc    840

ctctgggagg atcactaagc aaacactgcc caccagcacc agctcctcta tcaagccaaa    900

gaagaagcca ctggatgaaa aatacttcac ccttcagatc catggccatg aatgtttcaa    960

gatgttccta aagctcaacg aggccttgga gctgaaggat gcccaggctg ggaagcaacc   1020

agggggaagc agggctcaat ccagccttcc caagtctaag aaaaggcaat ctatctccca   1080

ccataaaaaa ctaatgttca agaaagagca gcctgactca gactga                   1126
```

```
<210> SEQ ID NO 21
<211> LENGTH: 364
<212> TYPE: PRT
<213> ORGANISM: Loxodonta africana

<400> SEQUENCE: 21

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Gly Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Cys Asp Tyr Ser Asp Cys Leu Asp Pro Pro Gln
                165                 170                 175

His Leu Ile Gln Glu Glu Thr Cys Met Leu Ser Ile Trp Arg Thr Pro
            180                 185                 190

Ser Leu Tyr Asp Ile Val Trp Gly Ala Leu Gly Ala Thr Arg Gly Arg
        195                 200                 205

Phe Leu Pro Pro Ser Thr Ser Thr Ser Cys Val Thr Ala Pro Ala Trp
    210                 215                 220

Gly Ala Thr His Pro His His His His Ser Gly Ile Leu Gln Trp Ser
225                 230                 235                 240

Ala Gly Thr Gln Gln Phe Arg Gly Ala Tyr Leu Tyr Leu Ser Trp Glu
                245                 250                 255

Thr Gln Met Tyr Arg Gly Arg Gln Phe Pro Glu Glu Val Gly Ala Leu
            260                 265                 270

Pro Ala Thr Leu Trp Glu Asp His Ala Asn Thr Ala His Gln His Gln
        275                 280                 285

Leu Leu Tyr Gln Ala Lys Glu Glu Ala Thr Gly Lys Ile Leu His Pro
```

```
    290                 295                 300

Ser Asp Pro Trp Pro Met Phe Gln Asp Val Pro Lys Ala Gln Arg Gly
305                 310                 315                 320

Leu Gly Ala Glu Gly Cys Pro Gly Trp Glu Ala Thr Arg Gly Lys Gln
                325                 330                 335

Gly Ser Ile Gln Pro Ser Gln Val Glu Lys Ala Ile Tyr Leu Pro Pro
            340                 345                 350

Lys Thr Asn Val Gln Glu Arg Ala Ala Leu Arg Leu
        355                 360


<210> SEQ ID NO 22
<211> LENGTH: 1126
<212> TYPE: DNA
<213> ORGANISM: Loxodonta africana

<400> SEQUENCE: 22

gtggaggagc ctcagtcaga tctgagcatt gagctccctc tgagtcaaga gacattttca      60

tacttgggga aactcctttc tgagaagctg gttctatccc cctcactgtc cccagcagcg     120

gaggcagtag tcaatctgct actcccagaa gatgctgcag actggctaga aagccaaggt     180

ggggctcaag gaatatcaga agcacctaca ctagccacct cctggacgct gtcatcctct     240

gttccttctc agaagaccta cccagcacct atcatttctg tctgggcttc ttgcattctg     300

ggacagccaa gtccgtcacc tacacgtact cccctgaact taacatgctg ttttgccagc     360

tggcaaaggc ctgtccagtg cagccgtggg tcacctcaac acccccgccc agcacctgtg     420

ttcacaccat ggccatctac cagacatcag catatgatgg aggtcgtgaa gcactgcccc     480

caccttgagt gccgctctga ctatagcgat tgcttggacc ctcctcagca cctcatgcag     540

tgggaggaaa cctgcatgct gagtatttgg aggacaccat cactctatga catagtgtgg     600

ggtgccctag gagccaccag aggtcggttc tgactaccac catccacttc aacttcatgt     660

gtaacagctc ctgcatgggg cgcatgaacc cattctcacc attatgacaa tggaagactc     720

caatggtaat ccgctgggac acaacagttt cgaggtgcat atttgtacct gtcctgggag     780

acacagatgt acagaggaag acaatttcca caacaagtgg gagccttgcc ctgagccacc     840

ctctgggagg atcactacgc aaacactgcc caccagcacc agctcctcta cgaagccaaa     900

gaagaagcca ctggatgaaa aatacttcac ccttcagatc catgggcatg aatgtttcaa     960

gatgttccta aagctcaacg aggccttgga gctgaaggat gcccaggctg ggaagcagcc    1020

agaggggagc agggctcaat ctagccttcc caagtctaag aaaaggcaat ctacctcctg    1080

ccataaaaaa ctaatgttca agagagagca gcctgactca gactga                   1126


<210> SEQ ID NO 23
<211> LENGTH: 365
<212> TYPE: PRT
<213> ORGANISM: Loxodonta africana

<400> SEQUENCE: 23

Val Glu Glu Pro Gln Ser Asp Leu Ser Ile Glu Leu Pro Leu Ser Gln
1               5                   10                  15

Glu Thr Phe Ser Tyr Leu Gly Lys Leu Leu Ser Glu Lys Leu Val Leu
            20                  25                  30

Ser Pro Ser Leu Ser Pro Ala Ala Glu Ala Val Val Asn Leu Leu Leu
        35                  40                  45

Pro Glu Asp Ala Ala Asp Trp Leu Glu Ser Gln Gly Gly Ala Gln Gly
    50                  55                  60
```

```
Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Pro Ser Pro Thr Arg Thr Pro Leu
            100                 105                 110

Asn Leu Thr Cys Cys Phe Ala Ser Trp Gln Arg Pro Val Gln Cys Ser
        115                 120                 125

Arg Gly Ser Pro Gln His Pro Arg Pro Ala Pro Val Phe Thr Pro Trp
    130                 135                 140

Pro Ser Thr Arg His Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Met Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Thr His Ser His His Tyr Asp Asn Gly Arg Leu Gln Trp
225                 230                 235                 240

Ser Ala Gly Thr Gln Gln Phe Arg Gly Ala Tyr Leu Tyr Leu Ser Trp
                245                 250                 255

Glu Thr Gln Met Tyr Arg Gly Arg Gln Phe Pro Gln Gln Val Gly Ala
            260                 265                 270

Leu Pro Ala Thr Leu Trp Glu Asp His Tyr Ala Asn Thr Ala His Gln
        275                 280                 285

His Gln Leu Leu Tyr Glu Ala Lys Glu Glu Ala Thr Gly Lys Ile Leu
    290                 295                 300

His Pro Ser Asp Pro Trp Ala Met Phe Gln Asp Val Pro Lys Ala Gln
305                 310                 315                 320

Arg Gly Leu Gly Ala Glu Gly Cys Pro Gly Trp Glu Ala Ala Arg Gly
                325                 330                 335

Glu Gln Gly Ser Ile Pro Ser Gln Val Glu Lys Ala Ile Tyr Leu Leu
            340                 345                 350

Pro Lys Thr Asn Val Gln Glu Arg Ala Ala Leu Arg Leu
        355                 360                 365
```

<210> SEQ ID NO 24
<211> LENGTH: 1126
<212> TYPE: DNA
<213> ORGANISM: Loxodonta africana

<400> SEQUENCE: 24

```
atggaggagc ctcagtcaga tctcagcact gagctccctc tgagtcaaga gacgttttca      60

tacttgggga aactccttcc tgagaagctg gttctatccc cctcactgtc cccagcagcg     120

gaggcagtag tcaatctgct actcccagaa gatgctgcag actggctaga aagccaagct     180

ggggctcaag gaatatcaga agcgcctaca ctagccacct cctggacgct gtcatcctct     240

gttccttctc agaagaccta cccagcacct atcatttctg tctgggcttc ttgcattctg     300

ggacagccaa gtccgtcacc tacacgtact cccctgaact taacatgctg ttttgccagc     360

tggcaaaggc ctgtccagtg cagccatggg tcacctcaac acccccgccc agcacctgtg     420
```

```
ttcacaccat ggccatctac cagacatcag catatgatgg aggtcgtgaa gcactgcccc    480

caccttgagt gccgctctaa ctatagcgat tgcttggacc ctactcagca cctcatgcag    540

tgggaggaaa cctgcatgct gagtatttgg aggacaccat cactctatga catagtgtgg    600

ggtgccctag gagccaccag aggtcggttc tgactaccac catccacttc aacttcatgt    660

gtaacagctc ctgcatgggg cgcatgaacc cattctcacc attatgacaa tggaagactc    720

caatggtaat ccgctgggac acaacagttt cgaggtgcat atttgtacct gtcctgggag    780

acacagatgt acagaggaag acaatttcca caacaagtgg gagccttgcc ctgagccacc    840

ctctgggagg atcactacgc aaacactgcc caccagcacc agctcctcta cgaagccaaa    900

gaagaagcca ctggatgaaa aatacttcac ccttcagatc catgggcatg aatgtttcaa    960

gatgttccta aagctcaatg aggccttgga gctgaaggat gcccaggccg ggaaacagcc   1020

agaggggagc agggctcaat ctagccttcc caagtctaag aaaaggcaat ctacctcccg   1080

ccataaaaaa ctaatgttca agagagagca gcctgactca gactga                  1126


<210> SEQ ID NO 25
<211> LENGTH: 364
<212> TYPE: PRT
<213> ORGANISM: Loxodonta africana

<400> SEQUENCE: 25

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Val Asn Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Pro Ser Pro Thr Arg Thr Pro Leu
            100                 105                 110

Asn Leu Thr Cys Cys Phe Ala Ser Trp Gln Arg Pro Val Gln Cys Ser
        115                 120                 125

His Gly Ser Pro Gln His Pro Arg Pro Ala Pro Val Phe Thr Pro Trp
    130                 135                 140

Pro Ser Thr Arg His Gln His Met Met Glu Val Val Lys His Cys Pro
145                 150                 155                 160

His Leu Glu Cys Arg Ser Asn Tyr Ser Asp Cys Leu Asp Pro Thr Gln
                165                 170                 175

His Leu Met Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Thr His Ser His His Tyr Asp Asn Gly Arg Leu Gln Trp
225                 230                 235                 240

Ser Ala Gly Thr Gln Gln Phe Arg Gly Ala Tyr Leu Tyr Leu Ser Trp
```

```
                245                 250                 255

Glu Thr Gln Met Tyr Arg Gly Arg Gln Phe Pro Gln Gln Val Gly Ala
            260                 265                 270

Leu Pro Ala Thr Leu Trp Glu Asp His Tyr Ala Asn Thr Ala His Gln
        275                 280                 285

His Gln Leu Leu Tyr Glu Ala Lys Glu Glu Ala Thr Gly Lys Ile Leu
    290                 295                 300

His Pro Ser Asp Pro Trp Ala Met Phe Gln Asp Val Pro Lys Ala Gln
305                 310                 315                 320

Gly Leu Gly Ala Glu Gly Cys Pro Gly Arg Glu Thr Ala Arg Gly Glu
                325                 330                 335

Gln Gly Ser Ile Pro Ser Gln Val Glu Lys Ala Ile Tyr Leu Pro Pro
            340                 345                 350

Lys Thr Asn Val Gln Glu Arg Ala Ala Leu Arg Leu
        355                 360


<210> SEQ ID NO 26
<211> LENGTH: 1127
<212> TYPE: DNA
<213> ORGANISM: Loxodonta africana

<400> SEQUENCE: 26

atggaggagc ctcagtcaga tctcagcact gagctccctc tgagtcaagg gacgttttca      60

tacttgggga aactccttcc tgagaagctg gttctgttcc cctcactgtc cccagcagca     120

gaggcaatag acgatctgct actcccagaa gatgctgcag actggctaga aagccaagct     180

ggggctcaag gagtatcaga agcccctaca ctagccacct cctggacgct gtcatcctct     240

gtcccttctc agaagaccta cccagcacct atcgtttctg tctgggcttc ttgcattctg     300

ggacagccaa gtccgtcacc tacacgtact cccctgaact taacatgctg ttttgccagc     360

tggcaaaggc ctgtccagtg cagccgtggg tcacctcaac acccccgccc agcacctgtg     420

ttcacaccat ggccatctac cagacgtcag catatgatgg aggtcacgaa gcactgccgc     480

caccttgagt gccgctctgt actatagcga ttgcttggac cctcctcagc acctcatgca     540

gtgggaggaa acctgcatgc tgagtatttg gaggacacca tcactctatg acatagtgtg     600

gggtgcccta ggagccacca gaggtcagtt ctgactacca ccatccactt caacttcatg     660

tgtaacagct cctgcatggg gggcaggaac ccatcctcac catcatcaca ctggaagact     720

ccaatggtaa tccgctggga cacaacagtt tcgaggtgca tatttgtact tgtcctggga     780

gacacagatg tacagaggaa gacaatttcc agaagaagtg ggagccttgc cctgagccag     840

gctcggggag gatcactaag caaacactgc ccaccagcac cagctcctct accaagccaa     900

agaagaagcc actggatgaa aaatacttca ctcttcagat ccatggccat gaatgtttca     960

agatgttcct aaagctcaac gaggccttgg agctgaagga tgcccaggct gggaagcagc    1020

cagaggggag cagggctcaa tccagccttc ccaagtctaa caaaaggcaa tcttcctccc    1080

gccataaaaa actaatgttc aagagagagc agcctgactc agactga                  1127


<210> SEQ ID NO 27
<211> LENGTH: 370
<212> TYPE: PRT
<213> ORGANISM: Loxodonta africana

<400> SEQUENCE: 27

Met Glu Glu Pro Gln Ser Asp Leu Ser Thr Glu Leu Pro Leu Ser Gln
1               5                   10                  15
```

```
Gly Thr Phe Ser Tyr Leu Gly Lys Leu Leu Pro Glu Lys Leu Val Leu
            20                  25                  30

Phe Pro Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Val Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Pro Ser Pro Thr Arg Thr Pro Leu
            100                 105                 110

Asn Leu Thr Cys Cys Phe Ala Ser Trp Gln Arg Pro Val Gln Cys Ser
        115                 120                 125

Arg Gly Ser Pro Gln His Pro Arg Pro Ala Pro Val Phe Thr Pro Trp
    130                 135                 140

Pro Ser Thr Arg Arg Gln His Met Met Glu Val Thr Lys His Cys Arg
145                 150                 155                 160

His Leu Glu Cys Arg Ser Val Leu Arg Leu Leu Gly Pro Ser Ser Ala
                165                 170                 175

Pro His Ala Val Gly Gly Asn Leu His Ala Glu Tyr Leu Glu Asp Thr
            180                 185                 190

Ile Thr Leu His Ser Val Gly Cys Pro Arg Ser His Gln Arg Ser Val
        195                 200                 205

Leu Thr Thr Thr Ile His Phe Asn Phe Met Cys Asn Ser Ser Cys Met
    210                 215                 220

Gly Gly Arg Asn Pro Ser Ser Pro Ser Ser His Trp Lys Thr Pro Met
225                 230                 235                 240

Val Ile Arg Trp Asp Thr Thr Val Ser Arg Cys Ile Phe Val Leu Val
                245                 250                 255

Leu Gly Asp Thr Asp Val Gln Arg Lys Thr Ile Ser Arg Arg Ser Gly
            260                 265                 270

Ser Leu Ala Leu Ser Gln Ala Arg Gly Gly Ser Leu Ser Lys His Cys
        275                 280                 285

Pro Pro Ala Pro Ala Pro Leu Pro Ser Gln Arg Arg Ser His Trp Met
    290                 295                 300

Lys Asn Thr Ser Leu Phe Arg Ser Met Ala Met Asn Val Ser Arg Cys
305                 310                 315                 320

Ser Ser Ser Thr Arg Pro Trp Ser Arg Met Pro Arg Leu Gly Ser Ser
                325                 330                 335

Gln Arg Gly Ala Gly Leu Asn Pro Ala Phe Pro Ser Leu Thr Lys Gly
            340                 345                 350

Asn Leu Pro Pro Ala Ile Lys Asn Cys Ser Arg Glu Ser Ser Leu Thr
        355                 360                 365

Gln Thr
    370
```

<210> SEQ ID NO 28
<211> LENGTH: 1126
<212> TYPE: DNA
<213> ORGANISM: Loxodonta africana

<400> SEQUENCE: 28

```
atggaggagg ctcagtcaga tctcagcact gagctccctc tgagtcaaga gacgttttca      60
```

-continued

```
tacttgggga aactccttcc tgagaagctg gttctgttcc cctcactgtc cccagcagca    120

gaggcagtag acgatctgct actcccagaa gatgctgcag actggctaga aagccaagct    180

ggggctcaag gaatatcaga agcccctacg ctagccacct cctggacgct gtcatcctct    240

gtcccttctc agaagaccta cccagcacct atcacttctg tctgggcttc ttgcattctg    300

ggacagccaa gtctgtcacc tacacgtact cccctgaact taacgtgctg ttttgccagc    360

tggcaaaggc ctgtccagtg cagctgtggg tcacctcaac acccccgccc agcacctgtg    420

ttcacaccat ggccatctac cagatgtcag catatgatgg aggtcgtgaa gcactgcccc    480

caccttgagt gccgctctga ctatagcgat tgcttagacc ctcctcagca ccttatccag    540

tgggaggaaa cctgcatgct gagtatttgg aggacaccat cactctatga catagtgtgg    600

ggtgccctag gagccaccag aggtcggttc tgactaccac catccacttc aacttcatgt    660

gtaacagctc ctgcatgggg ggcaggaact catcctcacc atcatcacac tggaagactc    720

caatggtaat ccgctgggac acaacagttt cgaggtgcat atttgtactt gtcctgggag    780

acacagatgt acagaggaag acaatttcca taagaagtgg gagccttgcc ctgagccagg    840

ctcgggaagg atcactaagc gaacactgcc caccagcacc agctcctcta ccaagccaaa    900

gaagaagcca ctggatgaaa aatacttcac tcttcagatc catggccatg aatgcttcaa    960

gatgttccta aagctcaacg aggccttgga gctcaaggat gcccaggctg ggaagcagcc   1020

agaggggaac agggctcaat ccagccttcc caagtctaag aaaaggcaat ctacctcccg   1080

ccataaaaaa cttatgttca agagagagca gcctgactca gactga                  1126
```

<210> SEQ ID NO 29
<211> LENGTH: 365
<212> TYPE: PRT
<213> ORGANISM: Loxodonta africana

<400> SEQUENCE: 29

```
Met Glu Glu Ala Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Phe Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Thr Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Cys Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
```

-continued

```
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr His Pro His His His His Thr Gly Arg Leu Gln
225                 230                 235                 240

Trp Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Glu Val Gly Ala
            260                 265                 270

Leu Pro Ala Arg Leu Gly Lys Asp His Ala Asn Thr Ala His Gln His
        275                 280                 285

Gln Leu Leu Tyr Gln Ala Lys Glu Glu Ala Thr Gly Lys Ile Leu His
    290                 295                 300

Ser Ser Asp Pro Trp Pro Met Leu Gln Asp Val Pro Lys Ala Gln Arg
305                 310                 315                 320

Gly Leu Gly Ala Gln Gly Cys Pro Gly Trp Glu Ala Ala Arg Gly Glu
                325                 330                 335

Gln Gly Ser Ile Gln Pro Ser Gln Val Glu Lys Ala Ile Tyr Leu Pro
            340                 345                 350

Pro Lys Thr Tyr Val Gln Glu Arg Ala Ala Leu Arg Leu
        355                 360                 365


<210> SEQ ID NO 30
<211> LENGTH: 1126
<212> TYPE: DNA
<213> ORGANISM: Loxodonta africana

<400> SEQUENCE: 30

aaggaggagc ctcagtcaga tctcagcact gagctccctc tgagtcaagg gacgttttca     60

tacttgggga aactccttcc tgagaagctg gttctgttcc cctcactgtc cccagcagca    120

gaggcagtag acgatctgct actcccagaa gatgctgcag actggctaga aagccaagct    180

ggggctcaag gaatatcaga agcccctaca ctagccacct cctggacgct gtcatcctct    240

gtcccttctc agaagaccta cccagcacct atcatttctg tctgggcttc ttgcattctg    300

ggacagccaa gtctgtcacc tacacgtact cccctgaact taacatgctg ttttgccagc    360

tggcaaaggc ctgtccagtg cagctgtggg tcacctcaac acccccgccc agcacctgtg    420

ttcacaccat ggccatctac cagacgtcag catatgatgg aggtcgtgaa gcactgcccc    480

caccttgagt gccgctctga ctatagcgat tgcttagacc ctcctcagca ccttatccag    540

tgggaggaaa cctgcatgct gagtatttgg aggacaccat cactctatga catagtgtgg    600

ggtgccctag gagccaccag aggtcggttc tgactaccac catccacttc aacttcatgt    660

gtaacagctc ctgcatgggg ggcaggaacc catcctcacc atcatcacac tggaagactc    720

caatggtaat ccgctgggac acaacagttt cgaggtgcat atttgtactt gtcctgggag    780

acacagatgt acagaggaag acaatttcca taagaagtgg gagccttgcc ctgagccagg    840

ctcggggagg atcactaagc gaacactgcc caccagcacc agctcctcta ccaagccaaa    900

gaagaagcca ctggatgaaa aatacttcac tcttcagatc catggccatg aatgcttcaa    960

gatgttccta aagctcaacg aggccttgga gctcaaggat gcccaggctg ggaagcagcc   1020

agaggggaac agggctcaat ccagccttcc caagtctaag aaaaggcaat ctacctcccg   1080
```

```
ccataaaaaa cttatgttca agagagagca gcctgactca gactga              1126


<210> SEQ ID NO 31
<211> LENGTH: 365
<212> TYPE: PRT
<213> ORGANISM: Loxodonta africana

<400> SEQUENCE: 31

Lys Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Phe Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr His Pro His His His His Thr Gly Arg Leu Gln
225                 230                 235                 240

Trp Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Glu Val Gly Ala
            260                 265                 270

Leu Pro Ala Arg Leu Gly Glu Asp His Ala Asn Thr Ala His Gln His
        275                 280                 285

Gln Leu Leu Tyr Gln Ala Lys Glu Glu Ala Thr Gly Lys Ile Leu His
    290                 295                 300

Ser Ser Asp Pro Trp Pro Met Leu Gln Asp Val Pro Lys Ala Gln Arg
305                 310                 315                 320

Gly Leu Gly Ala Gln Gly Cys Pro Gly Trp Glu Ala Ala Arg Gly Glu
                325                 330                 335

Gln Gly Ser Ile Gln Pro Ser Gln Val Glu Lys Ala Ile Tyr Leu Pro
            340                 345                 350

Pro Lys Thr Tyr Val Gln Glu Arg Ala Ala Leu Arg Leu
        355                 360                 365
```

<210> SEQ ID NO 32
<211> LENGTH: 1126
<212> TYPE: DNA
<213> ORGANISM: Loxodonta africana

<400> SEQUENCE: 32

```
atggaggagc ctcagtcaga tctcagcact gagctccctc tgagtcaagg gacgttttca     60
tacttgggga aactccttcc tgagaagctg gttctgttcc cctcactgtc cccagcagca    120
gaggcagtag acgatctgct actcccagaa gatgctgcag actggctaga aagccaagct    180
ggggctcaag gaatatcaga agcccctaca ctagccacct cctggacgct gtcatcctct    240
gtcccttctc agaagaccta cccagcacct atcatttctg tctgggcttc ttgcattctg    300
ggacagccaa gtctgtcacc tacacgtact cccctgaact taacatgctg ttttgccagc    360
tggcaaaggc ctgtccagtg cagctgtggg tcacctcaac atccccgccc agcacctgtg    420
ttcacaccat ggccatctac cagacgtcag catatgatgg aggtcgtgaa gcactgcccc    480
caccttgagt gccgctctga ctatagtgat tgcttagacc ctcctcagca ccttatccag    540
tgggaggaaa cctgcatgct gagcatttgg aggacaccat cactctatga catagtgtgg    600
ggtgccctag gagccaccag aggtcggttc tgactaccac catccacttc aacttcatgt    660
gtaacagctc ctgcatgggg ggcaggaacc catcctcacc atcatcacac tggaagactc    720
caatggtaat ccgctgggac acaacagttt cgaggtgcat atttgtactt gtcctgggag    780
acacagatat acagaggaag acaatttcca taagaagtgg gagccttgcc ctgagccagg    840
ctcggggagg atcactaagt gaacactgcc caccagcacc agctcctcta ccaagccaaa    900
gaagaagcca ctggatgaaa aatacttcac tcttcagatc catggccatg aatgcttcaa    960
gatgttccta aagctcaacg aggccttgga gctcaaggat gcccagactg ggaagcagcc   1020
agaggggaac agggctcaat ccagccttcc caagtctaag aaaaggcaat ctacctcccg   1080
ccataaaaaa cttatgttca acagagagca gcctgactca gactga                  1126
```

<210> SEQ ID NO 33
<211> LENGTH: 365
<212> TYPE: PRT
<213> ORGANISM: Loxodonta africana

<400> SEQUENCE: 33

```
Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Phe Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
```

```
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr His Pro His His His His Thr Gly Arg Leu Gln
225                 230                 235                 240

Trp Ser Ala Gly Thr Gln Gln Phe Arg Gly Ala Tyr Leu Tyr Leu Ser
                245                 250                 255

Trp Glu Thr Gln Ile Tyr Arg Gly Arg Gln Phe Pro Glu Val Gly Ala
            260                 265                 270

Leu Pro Ala Arg Leu Gly Glu Asp His Val Asn Thr Ala His Gln His
        275                 280                 285

Gln Leu Leu Tyr Gln Ala Lys Glu Glu Ala Thr Gly Lys Ile Leu His
    290                 295                 300

Ser Ser Asp Pro Trp Pro Met Leu Gln Asp Val Pro Lys Ala Gln Arg
305                 310                 315                 320

Gly Leu Gly Ala Gln Gly Cys Pro Asp Trp Glu Ala Ala Arg Gly Glu
                325                 330                 335

Gln Gly Ser Ile Gln Pro Ser Gln Val Glu Lys Ala Ile Tyr Leu Pro
            340                 345                 350

Pro Lys Thr Tyr Val Gln Gln Arg Ala Ala Leu Arg Leu
        355                 360                 365
```

<210> SEQ ID NO 34
<211> LENGTH: 1121
<212> TYPE: DNA
<213> ORGANISM: Loxodonta africana

<400> SEQUENCE: 34

```
gtggaggagc ctcagtcaga tctcagcact gagctccctc tgagtcaagg gacgttttca     60

tacttgggga aactccttcc tgagaagctg gttctgtccc tctcactgtc cccagcagca    120

gaggcagtag acgatctgct actcccagaa gatgctgcag actggctaga aagccaagct    180

ggggctcaag gagtatcaga agcccctaca ctagccacct cctggacgct gtcatcctct    240

gtcccttctc agaagaccta cccagcacct atcgtttctg tctgggcttc tagcattctg    300

ggacagccca gttcgtcact tacacgtact cccctgaact taacatgctg ttttgccagc    360

tggcaaaggc ctgtccagcg cagctgtggg tcaccctcaa cacccccgcc cagcacctgt    420

gttcacacca tggccatcta ccagacgtca gcatatgatg gaggtcgtga agcactgccc    480

ccaccttgag tgccgctcta actatagcga ttgcttggac cctcctcagc acctcatcca    540

gtgggaggaa acctgcatgc tgagtatttg gaggacacca tcactctatg acatagtgtg    600

ggtgccccta ggagccacca gaggtcggtt ctgactacca ccatccactt catgtgtaac    660

agctcctgca tggggggcag gaagccatcc tcaccatcat cacactggaa gactccaaag    720

gtaatccgct gggacacaac agtttcgagg tgcatatttg tacttgtcct gggagacaca    780

gatatacaga ggaagacaat ttccataaga agtgggagcc ttgccctgag ccaggctcgg    840
```

```
ggaggatcac taagcgaaca ctgcccacca gcaccagctc ctctaccaag ccaaagaaga    900

agccactgga tgaaaaatac ttcactcttc agatccatgg ccatgaatgc ttcaagatgt    960

tcctaaagct caacgaggcc ttggagctca aggatgccca ggctgggaag cagccagagg   1020

ggagcagggc tcaatccagc cttcccaagt ctaagaaaag gcaatctacc tcccgccata   1080

aaaaacttat gttcaagaga gagcagcctg actcagactg a                       1121


<210> SEQ ID NO 35
<211> LENGTH: 368
<212> TYPE: PRT
<213> ORGANISM: Loxodonta africana

<400> SEQUENCE: 35

Val Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Ser Leu Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Val Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Ser Ile Leu Gly Gln Pro Ser Ser Ser Leu Thr Arg Thr Pro Leu
            100                 105                 110

Asn Leu Thr Cys Cys Phe Ala Ser Trp Gln Arg Pro Val Gln Arg Ser
        115                 120                 125

Cys Gly Ser Pro Ser Thr Pro Pro Pro Ser Thr Cys Val His Thr Met
    130                 135                 140

Ala Ile Tyr Gln Thr Ser Ala Tyr Asp Gly Gly Arg Glu Ala Leu Pro
145                 150                 155                 160

Pro Pro Val Pro Leu Leu Arg Leu Leu Gly Pro Ser Ser Ala Pro His
                165                 170                 175

Pro Val Gly Gly Asn Leu His Ala Glu Tyr Leu Glu Asp Thr Ile Thr
            180                 185                 190

Leu His Ser Val Gly Cys Pro Arg Ser His Gln Arg Ser Val Leu Thr
        195                 200                 205

Thr Thr Ile His Phe Met Cys Asn Ser Ser Cys Met Gly Gly Arg Lys
    210                 215                 220

Pro Ser Ser Pro Ser Ser His Trp Lys Thr Pro Lys Val Ile Arg Trp
225                 230                 235                 240

Asp Thr Thr Val Ser Arg Cys Ile Phe Val Leu Val Leu Gly Asp Thr
                245                 250                 255

Asp Ile Gln Arg Lys Thr Ile Ser Ile Arg Ser Gly Ser Leu Ala Leu
            260                 265                 270

Ser Gln Ala Arg Gly Gly Ser Leu Ser Glu His Cys Pro Pro Ala Pro
        275                 280                 285

Ala Pro Leu Pro Ser Gln Arg Arg Ser His Trp Met Lys Asn Thr Ser
    290                 295                 300

Leu Phe Arg Ser Met Ala Met Asn Ala Ser Arg Cys Ser Ser Ser Thr
305                 310                 315                 320
```

```
Arg Pro Trp Ser Ser Arg Met Pro Arg Leu Gly Ser Ser Gln Arg Gly
                325                 330                 335

Ala Gly Leu Asn Pro Ala Phe Pro Ser Leu Arg Lys Gly Asn Leu Pro
            340                 345                 350

Pro Ala Ile Lys Asn Leu Cys Ser Arg Glu Ser Ser Leu Thr Gln Thr
        355                 360                 365


<210> SEQ ID NO 36
<211> LENGTH: 1127
<212> TYPE: DNA
<213> ORGANISM: Loxodonta africana

<400> SEQUENCE: 36

atggaggagc ctcagtcaga tctcagcact gagctccctc tgagtcaaga gacgttttca     60

tacttgggga aactccttcc tgagaagctg gttctgttcc cctcactgtc cccagcagca    120

gaggcaatag acgatctgct actcccagaa gatgctgcag actggctaga aagccaagct    180

ggggctcaag gaatatcaga agcctctaca ctagccacct cctggacgct gtcatcctct    240

gtcccttctc agaagaccta cccagcacct atcgtttctg tctgggcttc ttgcattctg    300

ggacagccaa gttcgtcacc tacacgtact cccctgaact taacatgctg ttttgccagc    360

tggcaaaggc ctgtccagtg cagctgtggg tcacctcaac acccccgccc agcacctgtg    420

ttcacaccat ggccatctac cagacgtcag catatgatgg aggtcgtgaa gcattgcccc    480

ccaccttgag tgccgctctg actatagcga ttgcttggac cctcctcagc acctcatcca    540

gtgggaggaa acctgcatgc tgagtatttg gaggacacca tcactctatg acatagtgtg    600

gggtgcccta tgagccacca gaggtcggtt ctgactacca ccatccactt caacttcatg    660

tgtaacagct cctgcatggg gggcaggaag ccatcctcac catcatcaca ctggaagact    720

ccaatggtaa tccgctgaga cacaacagtt tcgaggtgca tatttgtact tgtcctggga    780

gacacagatg tacagaggaa gacaatttcc agaagaagtg ggagccttgc cctgagccag    840

gctcggggag gatcactaag cgaacactgc ccaccagcac cagctcctct accaagccaa    900

agaagaagcc actggatgaa aaatacttca ctcttcagat ccatggccat gaatgcttca    960

agatgttcct aaagctcaac gaggccttgg agttgaagga tgcccaggct gggaagcagc   1020

cagaggggag cagggctcaa tccagccttc ccaagtctaa gaaaaggcaa tctacctccc   1080

gccataaaaa acatatgttc aagagagagc agcctgactc agactga                 1127


<210> SEQ ID NO 37
<211> LENGTH: 368
<212> TYPE: PRT
<213> ORGANISM: Loxodonta africana

<400> SEQUENCE: 37

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Phe Pro Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Ser Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
```

```
                85                  90                  95

Ser Cys Ile Leu Gly Gln Pro Ser Ser Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

Pro Pro Val Pro Leu Leu Arg Leu Leu Gly Pro Ser Ser Ala Pro His
                165                 170                 175

Pro Val Gly Gly Asn Leu His Ala Glu Tyr Leu Glu Asp Thr Ile Thr
            180                 185                 190

Leu His Ser Val Gly Cys Pro Met Ser His Gln Arg Ser Val Leu Thr
        195                 200                 205

Thr Thr Ile His Phe Asn Phe Met Cys Asn Ser Ser Cys Met Gly Gly
    210                 215                 220

Arg Lys Pro Ser Ser Pro Ser Ser His Trp Lys Thr Pro Met Val Ile
225                 230                 235                 240

Arg Asp Thr Thr Val Ser Arg Cys Ile Phe Val Leu Val Leu Gly Asp
                245                 250                 255

Thr Asp Val Gln Arg Lys Thr Ile Ser Arg Arg Ser Gly Ser Leu Ala
            260                 265                 270

Leu Ser Gln Ala Arg Gly Gly Ser Leu Ser Glu His Cys Pro Pro Ala
        275                 280                 285

Pro Ala Pro Leu Pro Ser Gln Arg Arg Ser His Trp Met Lys Asn Thr
    290                 295                 300

Ser Leu Phe Arg Ser Met Ala Met Asn Ala Ser Arg Cys Ser Ser Ser
305                 310                 315                 320

Thr Arg Pro Trp Ser Arg Met Pro Arg Leu Gly Ser Ser Gln Arg Gly
                325                 330                 335

Ala Gly Leu Asn Pro Ala Phe Pro Ser Leu Arg Lys Gly Asn Leu Pro
            340                 345                 350

Pro Ala Ile Lys Asn Ile Cys Ser Arg Glu Ser Ser Leu Thr Gln Thr
        355                 360                 365


<210> SEQ ID NO 38
<211> LENGTH: 1126
<212> TYPE: DNA
<213> ORGANISM: Loxodonta africana

<400> SEQUENCE: 38

atggaagagc ctcagtcaga tctcagcact gagctccctc tgagtcaagg gacgttttca      60

tacttgggga aactccttcc tgagaagctg gttctgttcc cctcactgtc cccagcagca     120

gaggcaatag acgatctact actcccagaa gatgctgcag actggctaga aagccaagct     180

ggggctcaag gaatatcaga agcctctaca ctagccacct cctggacgct gtcatcctct     240

gtcccttctc agaagaccta cccagcacct atcgtttctg tctgggcttc ttgcattctg     300

ggacagccaa gttcgtcacc tagacgtact cccctgaact taacatgctg ttttgccagc     360

tggcaaaggc ctgtccagtg cagctgtggg tcacctcaac acccccgcca agcacctgtg     420

ttcacaccat ggccatctac cagacgtcag catatgatgg aggtcgtgaa gcactgcccc     480

caccttgagt gccgctctga ctatagcgat tgcttggacc ctcctcagca cctcatccag     540
```

```
tgggaggaaa cctgcatgct gagtatttgg aggacaccat cactctatga catagcgtgg    600

ggtgccctat gagccaccag aggtcggttc tgactaccac catccacttc aacctcatgt    660

gtaacagctc ctgcatgggg ggcaggaagc catcctcacc atcatcacac tggaagactc    720

caatggtaat ccgctgggac acaacagttt cgaggtgcat atttgtactt gtcctgggag    780

acacagatgt acagaggaag acaatttcca taagaagtgg gagccttgcc ctgagccagg    840

ctcggggagg atcactaagc gaacactgcc caccagcacc agctcctcta tcaagccaaa    900

gaagaagcca ctggatgaaa aatacttcac tcttcagatc catggccatg aatgcttcaa    960

gatgttccta aagctcaacg aggccttgga gctgaaggat gcccaggctg ggaagcagcc   1020

agaggggagc agggctcaat ccagccttcc caagtctaag aaaaggcaat ctacctcccg   1080

ccataaaaaa cttatgttca agagagagca gcctgactca gactga                  1126
```

<210> SEQ ID NO 39
<211> LENGTH: 364
<212> TYPE: PRT
<213> ORGANISM: Loxodonta africana

<400> SEQUENCE: 39

```
Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Phe Pro Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Ser Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Ser Ser Pro Arg Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Gln Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Ala Trp Gly Ala Leu Ala Thr Arg Gly Arg
        195                 200                 205

Phe Leu Pro Pro Ser Thr Ser Thr Ser Cys Val Thr Ala Pro Ala Trp
    210                 215                 220

Gly Ala Gly Ser His Pro His His His His Thr Gly Arg Leu Gln Trp
225                 230                 235                 240

Ser Ala Gly Thr Gln Gln Phe Arg Gly Ala Tyr Leu Tyr Leu Ser Trp
                245                 250                 255

Glu Thr Gln Met Tyr Arg Gly Arg Gln Phe Pro Glu Val Gly Ala Leu
            260                 265                 270
```

```
Pro Ala Arg Leu Gly Glu Asp His Ala Asn Thr Ala His Gln His Gln
        275                 280                 285

Leu Leu Tyr Gln Ala Lys Glu Glu Ala Thr Gly Lys Ile Leu His Ser
    290                 295                 300

Ser Asp Pro Trp Pro Met Leu Gln Asp Val Pro Lys Ala Gln Arg Gly
305                 310                 315                 320

Leu Gly Ala Glu Gly Cys Pro Gly Trp Glu Ala Ala Arg Gly Glu Gln
                325                 330                 335

Gly Ser Ile Gln Pro Ser Gln Val Glu Lys Ala Ile Tyr Leu Pro Pro
            340                 345                 350

Lys Thr Tyr Val Gln Glu Arg Ala Ala Leu Arg Leu
        355                 360
```

<210> SEQ ID NO 40
<211> LENGTH: 1143
<212> TYPE: DNA
<213> ORGANISM: Loxodonta africana

<400> SEQUENCE: 40

```
aagagaggag ccccagtaag atctcagcac tgacttccct ctgagccaag agaccttttc     60

atacttaggg gaactccttc ctgagaagct ggttcagtcc ccctcactgt ccccagcagt    120

ggaggtagtg gatgatctgc tactcacaga agatgttgca gactggctag aaagccaagc    180

tggggctcaa agaatatcag cagcccctgc accacccacc cctacaccag ccacctgctt    240

gaccctgtca tcctctgtcc cttcccagaa gacctaccca acacctatgg tttctgtctg    300

gacttcctac attctgggac agccatttcc gtcacctaca tgtactcccc tgaccttaac    360

aagctgtttt gccagctggc aaagacctgt ccggtgcagc tgtgggtgac ctcaccaccc    420

cggcccagca tctgtgttca caccacagcc atctaccaca agtcagcatg tgacggaggt    480

ggtgcagcac tgcccccacc ttgagtgccg ctctgactat ggcgatggcc tggcccctcc    540

tcagcatctc atccgggggg ggaggaaatc tgcttgccga gtatttggag gacaccatca    600

ctcttcgaca cggtgtgggg tgccctatga accaccagag atcggctctg actaccacca    660

tccaattcaa cttcgtgcgt aacaacttct gcatgggggg caggaatcca tcctcaccat    720

caacacactg gaagactcca aagataatct gctgggacac aacagtttcg aggtgcatat    780

ttgcacctgt cctggtagag acagacgtac agagaaagaa aatttccaca agacgtggga    840

gccttgccat gaaccacccct ctgggaggat cactaagcaa gcactgccca cgagcaccag    900

atcctctacc cagccaaaga agaagccact ggatgaaaaa tacttcaccc atcagatctg    960

tgggcatgaa tgcttcaaga cattcctaga gctgaatgaa gccttggagc tgaggatgcc   1020

cagcctggga agcagccaca ggggagcagg gctcaatcca ggcttctaaa gtctaagaaa   1080

gggccatcta cctcccgcca taaaaaacta atgttcaata gagatgggcc tgactcagac   1140

tga                                                                  1143
```

<210> SEQ ID NO 41
<211> LENGTH: 366
<212> TYPE: PRT
<213> ORGANISM: Loxodonta africana

<400> SEQUENCE: 41

```
Lys Arg Gly Ala Pro Val Arg Ser Gln His Leu Pro Ser Glu Pro Arg
1               5                   10                  15

Asp Leu Phe Ile Leu Arg Gly Thr Pro Ser Glu Ala Gly Ser Val Pro
            20                  25                  30
```

```
Leu Thr Val Pro Ser Ser Gly Gly Ser Gly Ser Ala Thr His Arg Arg
        35                  40                  45

Cys Cys Arg Leu Ala Arg Lys Pro Ser Trp Gly Ser Lys Asn Ile Ser
    50                  55                  60

Ser Pro Cys Thr Thr His Pro Tyr Thr Ser His Leu Leu Asp Pro Val
65                  70                  75                  80

Ile Leu Cys Pro Phe Pro Glu Asp Leu Pro Asn Thr Tyr Gly Phe Cys
                85                  90                  95

Leu Asp Phe Leu His Ser Gly Thr Ala Ile Ser Val Thr Tyr Met Tyr
            100                 105                 110

Ser Pro Asp Leu Asn Lys Leu Phe Cys Gln Leu Ala Lys Thr Cys Pro
        115                 120                 125

Val Gln Leu Trp Val Thr Ser Pro Pro Arg Pro Ser Ile Cys Val His
    130                 135                 140

Thr Thr Ala Ile Tyr His Lys Ser Ala Cys Asp Gly Gly Gly Ala Ala
145                 150                 155                 160

Leu Pro Pro Pro Val Pro Leu Leu Trp Arg Trp Pro Gly Pro Ser Ser
                165                 170                 175

Ala Ser His Pro Gly Gly Glu Glu Ile Cys Leu Pro Ser Ile Trp Arg
            180                 185                 190

Thr Pro Ser Leu Phe Asp Thr Val Trp Gly Ala Leu Thr Thr Arg Asp
        195                 200                 205

Arg Leu Leu Pro Pro Ser Asn Ser Thr Ser Cys Val Thr Thr Ser Ala
    210                 215                 220

Trp Gly Ala Gly Ile His Pro His His Gln His Thr Gly Arg Leu Gln
225                 230                 235                 240

Arg Ser Ala Gly Thr Gln Gln Phe Arg Gly Ala Tyr Leu His Leu Ser
                245                 250                 255

Trp Arg Gln Thr Tyr Arg Glu Arg Lys Phe Pro Gln Asp Val Gly Ala
            260                 265                 270

Leu Pro Thr Thr Leu Trp Glu Asp His Ala Ser Thr Ala His Glu His
        275                 280                 285

Gln Ile Leu Tyr Pro Ala Lys Glu Glu Ala Thr Gly Lys Ile Leu His
    290                 295                 300

Pro Ser Asp Leu Trp Ala Met Leu Gln Asp Ile Pro Arg Ala Glu Ser
305                 310                 315                 320

Leu Gly Ala Glu Asp Ala Gln Pro Gly Lys Gln Pro Gln Gly Ser Arg
                325                 330                 335

Ala Gln Ser Arg Leu Leu Lys Ser Lys Lys Gly Pro Ser Thr Ser Arg
            340                 345                 350

His Lys Lys Leu Met Phe Asn Arg Asp Gly Pro Asp Ser Asp
        355                 360                 365
```

<210> SEQ ID NO 42
<211> LENGTH: 1143
<212> TYPE: DNA
<213> ORGANISM: Loxodonta africana

<400> SEQUENCE: 42

```
acggagcagc cccagtcgga tctcagcact gagctccctc tgagtcaaga gacgttttca     60

tacttgggga aactcattcc tgagaagctg gttttgtccc cctcgttacg cccagcagta    120

gaggttgtag acgatctgct actcccagaa gatgctgcac actggctaga atgccatgtt    180

ggggttcaaa gaatatcagc agcctctgca ccagccaccc ccacacaagc cacctcctgg    240
```

```
actctgtcat cctctgtccc ttctcagaag acctacccca gcacctatgg tttctgtctg    300

ggcttcttgc attctgggac agtcaagtcc gtcacctaca cgtactcccc tgaacataac    360

atggtgtttt gccagcaggc aaagacctgt ccagtgcagc cgtgggtcac ctcaccaccc    420

ctgcccagca cctgtgttca caccatggcc atctaccaga cgtcagcata tgatggaggt    480

tgtgaagcaa tgcccccacc ttgagtgccg ctctgactat agcgattgcc tcgcccctcc    540

tcagcatctc atctaggtgg ggggaaaccc gcatgctgag tatttggagg acaccatcac    600

tctatgacat agtgtggggt gccctatgag ccaccagagg tcggttctga ctaccactat    660

ccacttcaac ttcatgtgta acagctcctg cactgggggc acgaacccat cctcaccatc    720

atcacactgg aagactccaa tggtaatctg ctggcacaca acagtttcga ggtgcgtatt    780

tgtacctgtc ctgggaaaga cagatgtaca gaggaagacg atttccacag gaaatgggag    840

ccttgacctg acccatcctc tgagaggatc actaagtgag cactgcccac cagcaccagc    900

tcaactacta agccaaagaa gccgccactg gatgaaaaat atttcaccct tcagatccgt    960

gggcatgaat gcttcaagat gttcctagag ctgaatgagg ccttggagct aaggatgccc   1020

aggctgggaa gcagccagag ggaaaagggg ctcaatccag ccttcccaag tctaagaaaa   1080

ggcaatttac ctcccgccac agaagactaa tgttcaagag agagcagcct gacttagact   1140

gat                                                                 1143
```

```
<210> SEQ ID NO 43
<211> LENGTH: 363
<212> TYPE: PRT
<213> ORGANISM: Loxodonta africana

<400> SEQUENCE: 43

Gly Ala Ala Pro Val Gly Ser Gln His Ala Pro Ser Glu Ser Arg Asp
1               5                   10                  15

Val Phe Ile Leu Gly Glu Thr His Ser Glu Ala Gly Phe Val Pro Leu
            20                  25                  30

Val Thr Pro Ser Ser Arg Gly Cys Arg Arg Ser Ala Thr Pro Arg Arg
        35                  40                  45

Cys Cys Thr Leu Ala Arg Met Pro Cys Trp Gly Ser Lys Asn Ile Ser
    50                  55                  60

Ser Leu Cys Thr Ser His Pro His Thr Ser His Leu Leu Asp Ser Val
65                  70                  75                  80

Ile Leu Cys Pro Phe Ser Glu Asp Leu Pro Gln His Leu Trp Phe Leu
                85                  90                  95

Ser Gly Leu Leu Ala Phe Trp Asp Ser Gln Val Arg His Leu His Val
            100                 105                 110

Leu Pro Thr His Gly Val Leu Pro Ala Gly Lys Asp Leu Ser Ser Ala
        115                 120                 125

Ala Val Gly His Leu Thr Thr Pro Ala Gln His Leu Cys Ser His His
    130                 135                 140

Gly His Leu Pro Asp Val Ser Ile Trp Arg Leu Ser Asn Ala Pro Thr
145                 150                 155                 160

Leu Ser Ala Ala Leu Thr Ile Ala Ile Ala Ser Pro Leu Leu Ser Ile
                165                 170                 175

Ser Ser Arg Trp Gly Glu Thr Arg Met Leu Ser Ile Trp Arg Thr Pro
            180                 185                 190

Ser Leu Tyr Asp Ile Val Trp Gly Ala Leu Ala Thr Arg Gly Arg Phe
        195                 200                 205
```

```
Leu Pro Leu Ser Thr Ser Thr Ser Cys Val Thr Ala Pro Ala Leu Gly
    210                 215                 220

Ala Arg Thr His Pro His His His His Thr Gly Arg Leu Gln Trp Ser
225                 230                 235                 240

Ala Gly Thr Gln Gln Phe Arg Gly Ala Tyr Leu Tyr Leu Ser Trp Glu
                245                 250                 255

Arg Gln Met Tyr Arg Gly Arg Arg Phe Pro Gln Glu Met Gly Ala Leu
            260                 265                 270

Thr Pro Ile Leu Glu Asp His Val Ser Thr Ala His Gln His Gln Leu
        275                 280                 285

Asn Tyr Ala Lys Glu Ala Ala Thr Gly Lys Ile Phe His Pro Ser Asp
    290                 295                 300

Pro Trp Ala Met Leu Gln Asp Val Pro Arg Ala Glu Gly Leu Gly Ala
305                 310                 315                 320

Lys Asp Ala Gln Ala Gly Lys Gln Pro Glu Gly Lys Arg Ala Gln Ser
                325                 330                 335

Ser Leu Pro Lys Ser Lys Lys Arg Gln Phe Thr Ser Arg His Arg Arg
            340                 345                 350

Leu Met Phe Lys Arg Glu Gln Pro Asp Leu Asp
        355                 360
```

<210> SEQ ID NO 44
<211> LENGTH: 1130
<212> TYPE: DNA
<213> ORGANISM: Loxodonta africana

<400> SEQUENCE: 44

```
atggaggagc ccgagtcaga tctcagtact gagctccctc tgagtcaaga gactttttg     60

tacttgggga aactccttcc tgagaagctg gttctgtccc cctcactgtc cccagcagcg    120

gaggcaggag acgatctgct actcccagaa gatgctgcag actggctaga aagccaagct    180

ggggctcaag aaacatcagc agcccctgca ccagccaccc ttataccagc ctcctcctgg    240

acactctcgt cctctgtccc ttcccagaag acctactgca gcaactgtgg tttccgtctt    300

ggcttcctgc attctgggac agccaagtct gtcacctgca tgtactcccc tgaccttaac    360

aagctgtttt gccagctggc aaagacctgt ccagtgcagc cgtagctcag ctcaccaccc    420

caccccagca cctgtgttca caccatggcc atctaccaga cgtcagcata tgacagaggt    480

catgcagcac tgcccccacc ttgagtgctg ctctgactat agcgacggcc tggccgctcc    540

tcagcatctt atccaggtgg gagaaatcct gtgtgctgat atttgtagga caccatcact    600

ctttgacata gtgtggggta ccctatgagc tacctcaggt cggctctgac taccaccatc    660

cacttcaact tcatgtgtag cagctcctgc aagggggga ggaacccatc ctcaccatca    720

tcacactgga agactccagt ggtaatctgc taggacacaa cagtttcgaa gtgcatattt    780

gtacctgttc tgggagagac agacgtacag aggaagaaaa tttccacaac aagtgggagc    840

caccctctga gaggatcact aagtaagcac tgccaccagc actagctccc ctaccgagcc    900

aaagaagaag ccagtggatg aaaaatattt cacccttcag atccatgggc atgaatgatt    960

caagatattc ctagagttga atgaggcact ggagctgaag gatgcccagg ctgggaagca   1020

gccagagggg agcagggctc aatgcagcct tccaaactct aagaaagggg aatctaccac   1080

ccactgtaaa aactaatgt tcaagagaga ggggcctgac tcagactgac               1130
```

<210> SEQ ID NO 45

```
<211> LENGTH: 361
<212> TYPE: PRT
<213> ORGANISM: Loxodonta africana

<400> SEQUENCE: 45

Met Glu Glu Pro Glu Ser Asp Leu Ser Thr Glu Leu Pro Leu Ser Gln
1               5                   10                  15

Glu Thr Phe Leu Tyr Leu Gly Lys Leu Leu Pro Glu Lys Leu Val Leu
            20                  25                  30

Ser Pro Ser Leu Ser Pro Ala Ala Glu Ala Gly Asp Asp Leu Leu Leu
        35                  40                  45

Pro Glu Asp Ala Ala Asp Trp Leu Glu Ser Gln Ala Gly Ala Gln Glu
    50                  55                  60

Thr Ser Ala Ala Pro Ala Pro Ala Thr Leu Ile Pro Ala Ser Ser Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Asp Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Thr Ser Ala Tyr Asp Arg Gly His
145                 150                 155                 160

Ala Ala Leu Pro Pro Pro Val Leu Leu Leu Arg Arg Pro Gly Arg Ser
                165                 170                 175

Ser Ala Ser Tyr Pro Gly Gly Arg Asn Pro Val Cys Tyr Leu Asp Thr
            180                 185                 190

Ile Thr Leu His Ser Val Gly Tyr Pro Met Ser Tyr Leu Arg Ser Ala
        195                 200                 205

Leu Thr Thr Thr Ile His Phe Asn Phe Met Cys Ser Ser Ser Cys Lys
    210                 215                 220

Gly Gly Arg Asn Pro Ser Ser Pro Ser Ser His Trp Lys Thr Pro Val
225                 230                 235                 240

Val Ile Cys Asp Thr Thr Val Ser Lys Cys Ile Phe Val Pro Val Leu
                245                 250                 255

Gly Glu Thr Asp Val Gln Arg Lys Lys Ile Ser Thr Thr Ser Gly Ser
            260                 265                 270

His Pro Leu Arg Gly Ser Leu Ser Lys His Cys His Gln His Leu Pro
        275                 280                 285

Tyr Arg Ala Lys Glu Glu Ala Ser Gly Lys Ile Phe His Pro Ser Asp
    290                 295                 300

Pro Trp Ala Met Ile Gln Asp Ile Pro Arg Val Glu Gly Thr Gly Ala
305                 310                 315                 320

Glu Gly Cys Pro Gly Trp Glu Ala Ala Arg Gly Glu Gln Gly Ser Met
                325                 330                 335

Gln Pro Ser Lys Leu Glu Arg Gly Ile Tyr His Pro Leu Lys Thr Asn
            340                 345                 350

Val Gln Glu Arg Gly Ala Leu Arg Leu
        355                 360


<210> SEQ ID NO 46
<211> LENGTH: 1131
<212> TYPE: DNA
```

<213> ORGANISM: Loxodonta africana

<400> SEQUENCE: 46

```
aatggaggag cccaagtcag atctcagtac tgagctccct ctgagtcaag agactttttc     60
atgcttgggg aaactccttc ctgagaaggt ggttctgtcc ccctcactgt ccccagcagc    120
ggaggcagta gacgatctgc tactcccaga agatgctgca gactgcctag aaagccaagc    180
tggggctcaa ggaatatcag cagcccctgc accagccacc cttacaccag ccacctcctg    240
gacactctca tcctctgtcc cttcccagaa gacctactgc agcaactgtg gtttccgtct    300
tggcttcctg cattctggga cagccaagtc tgtcacctgc atgtactccc ctggccttaa    360
caagctgttt tgccagctgg caaagacctg tccagtgcag ccgtagctca cctcaccagc    420
ccaccccagc acctgtgttc acaccatggc catctaccag atgtcagcat atgacagagg    480
tcgtgcagca ctgcccccac cttgagtgct gctccgacta tagcgatggc ctggccgctc    540
ctcagcatct tatccaggtg ggaggaatcc tgcgtgctga tatttgtagg acaccatcac    600
tcttcgacat agtgtggggt atcctatgag ctacctcagg tcggttctga ctaccaccat    660
ccacttcaac ttcatgtgta gcagctcctg catggggcgg ggggaaccca tcctcaccat    720
catcacactg gaagactccg atggtaatct gctaggacac aacagtttcg aggtgcatat    780
ttgtactgtt ctgggagaga cagacgtaca gaggaagaaa atttccacaa caagtgggag    840
ccaccctctg agaggatcac taagtaagca ctgcccacca gcaccagctc ctctaccgag    900
ccaaagaaga agccagtgga tgaaaaatat ttcaccctta agatccgtgg gcatgaatgc    960
ttcaagatgt tcctagagtt gaatgaggca ttggagctga aggatgccca ggctgggaag   1020
cagccagaag ggagcagggc ccaatgcagc cttccaaact ctaagaaagg ggaatctacc   1080
acccactgta aaaaactaat gttcaagaga gaggggcctg actcagactg a            1131
```

<210> SEQ ID NO 47
<211> LENGTH: 367
<212> TYPE: PRT
<213> ORGANISM: Loxodonta africana

<400> SEQUENCE: 47

```
Met Glu Glu Pro Lys Ser Asp Leu Ser Thr Glu Leu Pro Leu Ser Gln
1               5                   10                  15

Glu Thr Phe Ser Cys Leu Gly Lys Leu Leu Pro Glu Lys Val Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Cys Leu Glu Ser Gln Ala Gly Ala Gln Gly
    50                  55                  60

Ile Ser Ala Ala Pro Ala Pro Ala Thr Leu Thr Pro Ala Thr Ser Trp
65                  70                  75                  80

Thr Leu Ser Ser Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Thr Ser Pro Ala His Pro Ser Thr Cys
    130                 135                 140

Val His Thr Met Ala Ile Tyr Gln Met Ser Ala Tyr Asp Arg Gly Arg
145                 150                 155                 160
```

```
Ala Ala Leu Pro Pro Pro Val Leu Leu Arg Leu Arg Trp Pro Gly Arg
                165                 170                 175

Ser Ser Ala Ser Tyr Pro Gly Gly Arg Asn Pro Ala Cys Tyr Leu Asp
            180                 185                 190

Thr Ile Thr Leu Arg His Ser Val Gly Tyr Pro Met Ser Tyr Leu Arg
        195                 200                 205

Ser Val Leu Thr Thr Thr Ile His Phe Asn Phe Met Cys Ser Ser Ser
    210                 215                 220

Cys Met Gly Arg Gly Glu Pro Ile Leu Thr Ile Ile Thr Leu Glu Asp
225                 230                 235                 240

Ser Asp Gly Asn Leu Leu Gly His Asn Ser Phe Glu Val His Ile Cys
                245                 250                 255

Thr Val Leu Gly Glu Thr Asp Val Gln Arg Lys Lys Ile Ser Thr Thr
            260                 265                 270

Ser Gly Ser His Pro Leu Arg Gly Ser Leu Ser Lys His Cys Pro Pro
        275                 280                 285

Ala Pro Ala Pro Leu Pro Ser Gln Arg Arg Ser Gln Trp Met Lys Asn
    290                 295                 300

Ile Ser Pro Leu Arg Ser Val Gly Met Asn Ala Ser Arg Cys Ser Ser
305                 310                 315                 320

Met Arg His Trp Ser Arg Met Pro Arg Leu Gly Ser Ser Gln Lys Gly
                325                 330                 335

Ala Gly Pro Asn Ala Ala Phe Gln Thr Leu Arg Lys Gly Asn Leu Pro
            340                 345                 350

Pro Thr Val Lys Asn Cys Ser Arg Glu Arg Gly Leu Thr Gln Thr
        355                 360                 365
```

<210> SEQ ID NO 48
<211> LENGTH: 1128
<212> TYPE: DNA
<213> ORGANISM: Loxodonta africana

<400> SEQUENCE: 48

```
aatggaggag cctcagtcag atctcagcac tgagctccct ctgagtcaag agacgttttc      60

atacttgggg aaactccttc ctgagaagct ggttctgttc ccctcactgt ccccagcagc     120

agaggcaata gacgatctgc tactcccaga agatgctgca gactggctag aaagccaagc     180

tggggctcaa ggaatatcag aagcctctac actagccacc tcctggacgc tgtcatcctc     240

tgtcccttct cagaagacct acccagcacc tatcgtttct gtctgggctt cttgcattct     300

gggacagcca agttcgtcac ctacacgtac tcccctgaac ttaacatgct gttttgccag     360

ctggcaaagg cctgtccagt gcagctgtgg gtcacctcaa cacccccgcc cagcacctgt     420

gttcacacca tggccatcta ccagacgtca gcatatgatg gaggtcgtga agcattgccc     480

cccaccttga gtgccgctct aactatagcg attgcttgga ccctactcag cacctcatgc     540

agtgggagga aacctgcatg ctgagtattt ggaggacacc atcactctat gacatagtgt     600

ggggtgccct atgagccacc agaggtcggt tctgactacc accatccact tcaacttcat     660

gtgtaacagc tcctgcatgg ggcgcatgaa cccattctca ccattatgac aatggaagac     720

tccaatggta atccgctggg acacaacagt ttcgaggtgc atatttgtac ctgtcctggg     780

agacacagat gtacagagga agacaatttc cacaacaagt gggagccttg ccctgagcca     840

ccctctggga ggatcactac gcaaacactg cccaccagca ccagctcctc tacgaagcca     900

aagaagaagc cactggatga aaaatacttc acccttcaga tccatgggca tgaatgtttc     960
```

```
aagatgttcc taaagctcaa tgaggccttg gagctgaagg atgcccaggc cgggaaacag   1020

ccagagggga gcagggctca atctagcctt cccaagtcta agaaaaggca atctacctcc   1080

cgccataaaa aactaatgtt caagagagag cagcctgact cagactga                1128


<210> SEQ ID NO 49
<211> LENGTH: 367
<212> TYPE: PRT
<213> ORGANISM: Loxodonta africana

<400> SEQUENCE: 49

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Phe Pro Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Ser Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Ser Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

Pro Pro Val Pro Leu Leu Arg Leu Leu Gly Pro Tyr Ser Ala Pro His
                165                 170                 175

Ala Val Gly Gly Asn Leu His Ala Glu Tyr Leu Glu Asp Thr Ile Thr
            180                 185                 190

Leu His Ser Val Gly Cys Pro Met Ser His Gln Arg Ser Val Leu Thr
        195                 200                 205

Thr Thr Ile His Phe Asn Phe Met Cys Asn Ser Ser Cys Met Gly Arg
    210                 215                 220

Met Asn Pro Phe Ser Pro Leu Gln Trp Lys Thr Pro Met Val Ile Arg
225                 230                 235                 240

Trp Asp Thr Thr Val Ser Arg Cys Ile Phe Val Pro Val Leu Gly Asp
                245                 250                 255

Thr Asp Val Gln Arg Lys Thr Ile Ser Thr Thr Ser Gly Ser Leu Ala
            260                 265                 270

Leu Ser His Pro Leu Gly Gly Ser Leu Arg Lys His Cys Pro Pro Ala
        275                 280                 285

Pro Ala Pro Leu Arg Ser Gln Arg Arg Ser His Trp Met Lys Asn Thr
    290                 295                 300

Ser Pro Phe Arg Ser Met Gly Met Asn Val Ser Arg Cys Ser Ser Ser
305                 310                 315                 320

Met Arg Pro Trp Ser Arg Met Pro Arg Pro Gly Asn Ser Gln Arg Gly
                325                 330                 335

Ala Gly Leu Asn Leu Ala Phe Pro Ser Leu Arg Lys Gly Asn Leu Pro
```

```
            340                 345                 350

Pro Ala Ile Lys Asn Cys Ser Arg Glu Ser Ser Leu Thr Gln Thr
        355                 360                 365


<210> SEQ ID NO 50
<211> LENGTH: 1121
<212> TYPE: DNA
<213> ORGANISM: Loxodonta africana

<400> SEQUENCE: 50

aatggaggag cctcagtcag atctcagcac tgagctccct ctgagtcaag ggacgttttc      60

atacttgggg aaactccttc ctgagaagct ggttctgtcc ccctcattgt ccccagcagc     120

ggaggcagta gatgatctgc tactctcaga agatgctgca gactggctag aaagccaagc     180

tggggctcaa ggaatatcag aagcgcctac actagccacc tcctggacgc tgtcatcctc     240

tgttccttct cagaagacct acccagcacc tatcatttct gtctgggctt cttgcattct     300

gggacagcca agtccgtcac ctacacgtac tcccctgaac ttaacatgct gttttgccag     360

ctggcaaagg cctgtccagt gcagccgtgg gtcacctcaa aaccccgtc cagcacctgt      420

gttcacacca tggccatcta ctagacgtca gcatatgatg gaggtcgtga agcactgccc     480

ccaccttgag tgccgctgtg actatagcga ttgcttggac cctcctcagc acctcatgca     540

gtgggaggaa acctgcatgc tgagtatttg gaggacacta tcactctatg acatagtgtg     600

gggtgcccta tgagccacca gaggtcagtt ctgactacca ccatccactt catgtgtaac     660

agctcctgca tgggggcag gaacccatcc tcaccatcat cacactggaa gactccaatg     720

gtaatccgct gggacacaac agtttcgagg tgcatatttg tacctgtcct gggagacgca     780

gatgtacaga ggaagacaat ttccacaaga agtgggagcc ttgccctgag ccaccctctg     840

ggaggatcac taagcaaaca ctgcccacca gcaccagctc ctctaccaag ccaaagaaga     900

agccactgga tgaaaaatac ttcacccttc agatccatgg gcatgaatgt ttcaagatgt     960

tcctaaagct caacgagacc ttggagctga aggatgccca ggctgggaag caaccagagg    1020

ggagcagggc tcaatgcagc cttcccaagt ctaagaaaag gcaatctatc tcccgccata    1080

aaaaaataat gttcaagaga gagcagcctg actcagactg a                        1121


<210> SEQ ID NO 51
<211> LENGTH: 363
<212> TYPE: PRT
<213> ORGANISM: Loxodonta africana

<400> SEQUENCE: 51

Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Ser Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Pro Ser Pro Thr Arg Thr Pro Leu
            100                 105                 110
```

```
Asn Leu Thr Cys Cys Phe Ala Ser Trp Gln Arg Pro Val Gln Cys Ser
        115                 120                 125

Arg Gly Ser Pro Gln Asn Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Cys Asp Tyr Ser Asp Cys Leu Asp Pro Pro Gln
                165                 170                 175

His Leu Met Gln Trp Glu Glu Thr Cys Met Leu Ser Ile Trp Arg Thr
            180                 185                 190

Leu Ser Leu Tyr Asp Ile Val Trp Gly Ala Leu Ala Thr Arg Gly Gln
        195                 200                 205

Phe Leu Pro Pro Ser Thr Ser Cys Val Thr Ala Pro Ala Trp Gly Ala
    210                 215                 220

Gly Thr His Pro His His His His Thr Gly Arg Leu Gln Trp Ser Ala
225                 230                 235                 240

Gly Thr Gln Gln Phe Arg Gly Ala Tyr Leu Tyr Leu Ser Trp Glu Thr
                245                 250                 255

Gln Met Tyr Arg Gly Arg Gln Phe Pro Gln Glu Val Gly Ala Leu Pro
            260                 265                 270

Ala Thr Leu Trp Glu Asp His Ala Asn Thr Ala His Gln His Gln Leu
        275                 280                 285

Leu Tyr Gln Ala Lys Glu Glu Ala Thr Gly Lys Ile Leu His Pro Ser
    290                 295                 300

Asp Pro Trp Ala Met Phe Gln Asp Val Pro Lys Ala Gln Arg Asp Leu
305                 310                 315                 320

Gly Ala Glu Gly Cys Pro Gly Trp Glu Ala Thr Arg Gly Glu Gln Gly
                325                 330                 335

Ser Met Gln Pro Ser Gln Val Glu Lys Ala Ile Tyr Leu Pro Pro Lys
            340                 345                 350

Asn Asn Val Gln Glu Arg Ala Ala Leu Arg Leu
        355                 360
```

<210> SEQ ID NO 52
<211> LENGTH: 1129
<212> TYPE: DNA
<213> ORGANISM: Loxodonta africana

<400> SEQUENCE: 52

```
aatggaggag cctcagtcag atctcagcac tgagctccct ctgagtcaag agacgttttc     60

atacttgggg aaactccttc ctgagaagct ggttctgtcc ccctcactgt ccccagaagc    120

ggaggcagta gacaatctgc tactcccaga agatgctgca gactggctag aaagccaagc    180

tggggctcaa ggaatatcag aagcccctac actagccacc tcctggatgc tgtcatcctc    240

tgtcccttct cagaagacct gcccagcacc tatcgtttct gtctgggctt cttgcattct    300

gggacagcca agtccgtcac ctacacatac tcccctgaac ttaacatgct gttttgccag    360

ctggcaaagg cctgcccagt gcagctgtgg gtcacctcaa cacccccgcc cagcacctgt    420

gttcacacca tggccatcta ccagacgtca gcatatgatg gaggtcatga agcactgccg    480

ccaccttgag tgccgctctg actatagcaa ttgcttggac cctcctcagc acctcatcca    540

gtgggaggaa acctgcatgc tgagtatttg gaggacacca tcactctatg acatagtgtg    600

gggtgcccta gtagccacca gaggtcggtt ctgactacca ccatccactt caacttcatg    660
```

```
tgtaacagct cctgcatggg gggcaggaac ctatcctcac catcatcaca ctggaagact    720

ccaacggtaa tccgctggga cacaacagtt tcgaggtgca tatttgtacc tgtcctggga    780

gacacagatg tacagaggaa gacagtttcc acaagaagtg ggagccttgc cctgagccag    840

cctctgggag gatcactaag cgaacactgc ccaccagcac cagctcctct accaagccaa    900

agaagaagcc actggataaa aaatacttca cccttcagat ccatgggcat gaatgattca    960

agatgttcct aaagctcaac gaggccttgg agctgaagga tgcccaggct gggaggcagc   1020

cagaggggag cagggctcaa cccagccttc ccaagtctaa gaaaaggcaa tctacctcct   1080

gccataaaaa aaactaatgt tctagagaga gcagcctgac tcagactga              1129


<210> SEQ ID NO 53
<211> LENGTH: 366
<212> TYPE: PRT
<213> ORGANISM: Loxodonta africana

<400> SEQUENCE: 53

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Glu Ala Glu Ala Val Asp Asn Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Met Leu Ser Ser Ser
65                  70                  75                  80

Val Pro Ser Gln Lys Thr Cys Pro Ala Pro Ile Val Ser Val Trp Ala
                85                  90                  95

Ser Cys Ile Leu Gly Gln Pro Ser Pro Ser Pro Thr His Thr Pro Leu
            100                 105                 110

Asn Leu Thr Cys Cys Phe Ala Ser Trp Gln Arg Pro Ala Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Met Lys His Cys Arg
145                 150                 155                 160

His Leu Glu Cys Arg Ser Asp Tyr Ser Asn Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Val Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr Tyr Pro His His His His Thr Gly Arg Leu Gln
225                 230                 235                 240

Arg Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Gln Glu Val Gly
            260                 265                 270

Ala Leu Pro Ala Ser Leu Trp Glu Asp His Ala Asn Thr Ala His Gln
        275                 280                 285

His Gln Leu Leu Tyr Gln Ala Lys Glu Glu Ala Thr Gly Lys Ile Leu
```

```
    290                 295                 300

His Pro Ser Asp Pro Trp Ala Met Ile Gln Asp Val Pro Lys Ala Gln
305                 310                 315                 320

Arg Gly Leu Gly Ala Glu Gly Cys Pro Gly Trp Glu Ala Ala Arg Gly
                325                 330                 335

Glu Gln Gly Ser Thr Gln Pro Ser Gln Val Glu Lys Ala Ile Tyr Leu
            340                 345                 350

Leu Pro Lys Lys Leu Met Phe Arg Glu Gln Pro Asp Ser Asp
        355                 360                 365


<210> SEQ ID NO 54
<211> LENGTH: 1127
<212> TYPE: DNA
<213> ORGANISM: Loxodonta africana

<400> SEQUENCE: 54

atggaggagc ctcagtcaga tctcagcact gagctccctt tgagtcaagg gacgttttca     60

tacttgggga aactccttcc tgagaagctg gttctgtccc tctcactgtc cccagcagca    120

gaggcagtag acgatctgtt actcccagaa gatgctgcag actggctaga aagccaagct    180

ggggctcaag gagtatcaga agcccctaca ctagccacct cctggacgtt gtcatcctct    240

gtcccttctc agaagaccta cccagcacct atcgtttctg tctgggcttc ttgcattctg    300

ggacagccaa gtccgtcacc tacacgtact cccctgaact taacatgctg ttttgccagc    360

tggcaaaggc ctgtccagtg cagccgtggg tcacctcaac aaccccgccc agcacctgtg    420

ttcacaccat ggccatctac cagacgtcag catatgatgg aggtcacgaa gcactgccgc    480

caccttgagt gccgctgtga ctatagcgat tgcttggacc ctcctcagca cctcatgcag    540

tgggaggaaa cctgcatgct gagtatttgg aggacaccat cactctatga catagtgtgg    600

ggtgccctag gagccaccag aggtcggttc tgactaccac catccacttc aacttcatgt    660

gtaacagctc ctgcatgggg ggcaggaacc catcctcacc atcatcacac tggaagactc    720

caatggtaat ccgctgggac acaacagttt cgaggtgcat atttgtactt gtcctgggag    780

acacagatgt acagaggaag acaatttcca taagaagtgg gagccttgcc ctgagccagg    840

ctcggggagg ttcactaagc gaacactgcc caccagcacc agctcctcta ccaagccaaa    900

gaagaagcca ctggatgaaa aatacttcac tcttcagatc catggccatg aatgtttcaa    960

gatgttccta aagctcaacg aggccttgga gctgaaggat gcccaggctg ggaagcagcc   1020

agaggggagc agggctcaat ccagacttcc caagtctaag aaaaggcaat ctacctcccg   1080

ccataaaaaa ctaatgttca agagagagca gcctgactca gactgac                 1127


<210> SEQ ID NO 55
<211> LENGTH: 365
<212> TYPE: PRT
<213> ORGANISM: Loxodonta africana

<400> SEQUENCE: 55

Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Ser Leu Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60
```

```
Val Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Pro Ser Pro Thr Arg Thr Pro Leu
            100                 105                 110

Asn Leu Thr Cys Cys Phe Ala Ser Trp Gln Arg Pro Val Gln Cys Ser
        115                 120                 125

Arg Gly Ser Pro Gln Gln Pro Arg Pro Ala Pro Val Phe Thr Pro Trp
    130                 135                 140

Pro Ser Thr Arg Arg Gln His Met Met Glu Val Thr Lys His Cys Arg
145                 150                 155                 160

His Leu Glu Cys Arg Cys Asp Tyr Ser Asp Cys Leu Asp Pro Pro Gln
                165                 170                 175

His Leu Met Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr His Pro His His His His Thr Gly Arg Leu Gln
225                 230                 235                 240

Trp Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Glu Val Gly Ala
            260                 265                 270

Leu Pro Ala Arg Leu Gly Glu Val His Ala Asn Thr Ala His Gln His
        275                 280                 285

Gln Leu Leu Tyr Gln Ala Lys Glu Glu Ala Thr Gly Lys Ile Leu His
    290                 295                 300

Ser Ser Asp Pro Trp Pro Met Phe Gln Asp Val Pro Lys Ala Gln Arg
305                 310                 315                 320

Gly Leu Gly Ala Glu Gly Cys Pro Gly Trp Glu Ala Ala Arg Gly Glu
                325                 330                 335

Gln Gly Ser Ile Gln Thr Ser Gln Val Glu Lys Ala Ile Tyr Leu Pro
            340                 345                 350

Pro Lys Thr Asn Val Gln Glu Arg Ala Ala Leu Arg Leu
        355                 360                 365
```

<210> SEQ ID NO 56
<211> LENGTH: 1126
<212> TYPE: DNA
<213> ORGANISM: Loxodonta africana

<400> SEQUENCE: 56

```
agtggaggag cctcagtcag atctcagcac tgagctccct ctgagtcaag ggatgttttc     60

atacttgggg aaactccttc ctgagaagct ggttctgtcc ctctcactgt ccccagcagc    120

agaggcagta gacgatctgc tactcccaga agatgctgca gactggctag aaagccaagc    180

tggggctcaa ggaatatcag aagcccctac gctagccacc tcctggacgc tgtcatcctc    240

tgtcccttct cagaagacct acccagcacc tatcacttct gtctgggctt cttgcattct    300

gggacagcca agtctgtcac ctacacgtac tcccctgaac ttaacgtgct gttttgccag    360

ctggcaaagg cctgtccagt gcagctgtgg gtcacctcaa catccctgcc cagcacctgt    420
```

```
gttcacacca tggccatcta ccagacgtca gcatatgatg gaggtcgtga agcactgccc    480

ccaccttgag tgccgctctg actatagcga ttgcttagac cctcctcagc accttatcca    540

gtgggaggaa acctgcatgc tgagtatttg gaggacacca tcactctatg acatagcgtg    600

gggtgcccta tgagccacca gaggtcggtt ctgactacca ccatccactt caacttcatg    660

tgtaacagct cctgcatggg gggcaggaac ccatcctcac catcatcaca ctggaagact    720

ccaatggtaa tccgctggga cacaacagtt tcgaggtgca tatttgtact tgtcctggga    780

gacacagatg tacagaggaa gacaatttcc ataagaagtg ggagccttgc cctgagccag    840

gctcggggag gatcactaag gaacactgcc caccagcacc agctcctcta ccaagccaaa    900

gaagaagcca ctggatgaaa aatacttcac tcttcagatc catggccatg aatgcttcaa    960

gatgttccta aagctcaatg aggccttgga gctcaaggat gcccaggctg ggaagcagcc   1020

agaggggaac agggctcaat ccagccttcc caagtctaag aaaaggcaat ctacctcccg   1080

ccataaaaaa cttatgttca agagagagca gcctgactca gactga                  1126


<210> SEQ ID NO 57
<211> LENGTH: 368
<212> TYPE: PRT
<213> ORGANISM: Loxodonta africana

<400> SEQUENCE: 57

Val Glu Glu Pro Gln Ser Asp Leu Ser Thr Glu Leu Pro Leu Ser Gln
1               5                   10                  15

Gly Met Phe Ser Tyr Leu Gly Lys Leu Leu Pro Glu Lys Leu Val Leu
            20                  25                  30

Ser Leu Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Thr Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Cys Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Ala Trp Gly Ala Leu Ala Thr Arg Gly Arg
        195                 200                 205

Phe Leu Pro Pro Ser Thr Ser Thr Ser Cys Val Thr Ala Pro Ala Trp
    210                 215                 220

Gly Ala Gly Thr His Pro His His His His Thr Gly Arg Leu Gln Trp
225                 230                 235                 240

Ser Ala Gly Thr Gln Gln Phe Arg Gly Ala Tyr Leu Tyr Leu Ser Trp
```

```
                245                 250                 255

Glu Thr Gln Met Tyr Arg Gly Arg Gln Phe Pro Glu Val Gly Ala Leu
            260                 265                 270

Pro Ala Arg Leu Gly Glu Asp His Gly Thr Leu Pro Thr Ser Thr Ser
        275                 280                 285

Ser Ser Thr Lys Pro Lys Lys Lys Pro Leu Asp Glu Lys Tyr Phe Thr
    290                 295                 300

Leu Gln Ile His Gly His Glu Cys Phe Lys Met Phe Leu Lys Leu Asn
305                 310                 315                 320

Glu Ala Leu Glu Leu Lys Asp Ala Gln Ala Gly Lys Gln Pro Glu Gly
                325                 330                 335

Asn Arg Ala Gln Ser Ser Leu Pro Lys Ser Lys Lys Arg Gln Ser Thr
            340                 345                 350

Ser Arg His Lys Lys Leu Met Phe Lys Arg Glu Gln Pro Asp Ser Asp
        355                 360                 365


<210> SEQ ID NO 58
<211> LENGTH: 1135
<212> TYPE: DNA
<213> ORGANISM: Loxodonta africana

<400> SEQUENCE: 58

atggaggagc ccgagtcaga tctcagtact gagctccttc tgagtcaaga gactttttcg      60

tacttgggga aactccttcc tgagaagctg gttctgtccc cctcactgtc cccagcagcg     120

gaggcagtag acgatctgct actcccagaa gatgctgcag actggctaga aagccaagct     180

ggggctcaag gaatatcagc agcccctgca ccagccaccc ttacaccagc cacctcctag     240

acactttcat cctctgtccc ttcccagaag acctactgca gcaactgtgg tttccatctt     300

ggcttcctgc attctgggac agccaagtct gtcacctgca cgtactcccc tgaccttaac     360

aagctgttct gccagctggc aaagacctgt ccagtgcagc cgtagctcag ctcaccaccc     420

cactccaccc cagcacctgt gttcacacca tggccatcta ccagatgtca gcacatgaca     480

gaggtcgtgc agcactgccc ccatcttgag tgctactccg actatagcga tggcctggcc     540

gctcctcagc atcttatcca ggtgggagga atcctgcgtg ctgatatttg taggacacca     600

ttactcttcg acatagtgtg gggtacccta tgagctacct caggtcggtt ctgactacca     660

ccatccactt caacttcatg tgtagcagct cctgcatggg gggggggaac ccatcctcac     720

catcatcaca ctggaagact ccgatggtaa tctgctagga cacaacagtt tcgaggtgca     780

tatttgtact gttctgggag agacagacgt acagaggaag aaaatttcca caacaagtgg     840

gagccagcct ctgagaggat cactgagtaa gcactgccca ccagcaccag ctcctctacc     900

gagccaaaga agaagccagt ggacgaaaaa tatttcaccc ttaagatcca tgggcatgaa     960

tgcttcaaga tgttcctaga gttgaacgag gcattggagc tgaaggatgc ccaggctggg    1020

aagcagtcag aggggagcag ggatcaatgc agccttccaa actctaggaa aggggaatct    1080

accacccact gtaaaaaact aatgttcaag agagaggggc ctgactcaga ctgac         1135


<210> SEQ ID NO 59
<211> LENGTH: 371
<212> TYPE: PRT
<213> ORGANISM: Loxodonta africana

<400> SEQUENCE: 59

Met Glu Glu Pro Glu Ser Asp Leu Ser Thr Glu Leu Leu Leu Ser Gln
1               5                   10                  15
```

```
Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Ala Ala Pro Ala Pro Ala Thr Leu Thr Pro Ala Thr Ser Thr
65                  70                  75                  80

Leu Ser Ser Ser Val Pro Ser Gln Lys Thr Tyr Cys Ser Asn Cys Gly
                85                  90                  95

Phe His Leu Gly Phe Leu His Ser Gly Thr Ala Lys Ser Val Thr Cys
            100                 105                 110

Thr Tyr Ser Pro Asp Leu Asn Lys Leu Phe Cys Gln Leu Ala Lys Thr
        115                 120                 125

Cys Pro Val Gln Pro Leu Ser Ser Pro Pro His Ser Thr Pro Ala Pro
    130                 135                 140

Val Phe Thr Pro Trp Pro Ser Thr Arg Cys Gln His Met Thr Glu Val
145                 150                 155                 160

Val Gln His Cys Pro His Leu Glu Cys Tyr Ser Asp Tyr Ser Asp Gly
                165                 170                 175

Leu Ala Ala Pro Gln His Leu Ile Gln Val Gly Gly Ile Leu Arg Ala
            180                 185                 190

Asp Ile Cys Arg Thr Pro Leu Leu Phe Asp Ile Val Trp Gly Thr Leu
        195                 200                 205

Ala Thr Ser Gly Arg Phe Leu Pro Pro Ser Thr Ser Thr Ser Cys Val
    210                 215                 220

Ala Ala Pro Ala Trp Gly Gly Gly Thr His Pro His His His His Thr
225                 230                 235                 240

Gly Arg Leu Arg Trp Ser Ala Arg Thr Gln Gln Phe Arg Gly Ala Tyr
                245                 250                 255

Leu Tyr Cys Ser Gly Arg Asp Arg Arg Thr Glu Glu Glu Asn Phe His
            260                 265                 270

Asn Lys Trp Glu Pro Ala Ser Glu Arg Ile Thr Glu Ala Leu Pro Thr
        275                 280                 285

Ser Thr Ser Ser Ser Thr Glu Pro Lys Lys Lys Pro Val Asp Glu Lys
    290                 295                 300

Tyr Phe Thr Leu Lys Ile His Gly His Glu Cys Phe Lys Met Phe Leu
305                 310                 315                 320

Glu Leu Asn Glu Ala Leu Glu Leu Lys Asp Ala Gln Ala Gly Lys Gln
                325                 330                 335

Ser Glu Gly Ser Arg Asp Gln Cys Ser Leu Pro Asn Ser Arg Lys Gly
            340                 345                 350

Glu Ser Thr Thr His Cys Lys Lys Leu Met Phe Lys Arg Glu Gly Pro
        355                 360                 365

Asp Ser Asp
    370
```

<210> SEQ ID NO 60
<211> LENGTH: 1127
<212> TYPE: DNA
<213> ORGANISM: Loxodonta africana

<400> SEQUENCE: 60

```
agtggaggag cctcagtcag atctcagcac tgagctccct ctgagtcaag ggacgttttc     60
```

```
atacttgggg aaactccttc ctgagaagct ggttctgtcc ctctcactgt ccccagcagc    120

agaggcagta gacgatctgc tactcccaga agatgctgca gactggctag aaagccaagc    180

tggggctcaa ggaatatcag aagcccctac actagccacc tcctggacgc tgtcatcctc    240

tgtcccttct cagaagacct acccagcacc tatcgtttct gtctgggctt cttgcattct    300

gggacagcca agtctgtcac ctacacgtac tcccctgaac ttaacatgct gttttgccgg    360

ctggcaaagg cctgtccagt gcagctgtgg gtcacctcaa cacccccgcc cagcacctgt    420

gttcacacca tggccatcta ccagacgtca gcatatgatg gaggtcgtga agcactgccc    480

ccaccttgag tgccgctgtg actatagcga ttgcttggac cctcctcagc acctcatcca    540

gtaggaggaa acctgcatgc tgagtatttg gaggacacca tcactctatg acatagtgtg    600

gggtgcccta ggagccacca gaggtcggtt ctgactacca ccatccactt caacttcatg    660

tgtaacagct cctgcatggg gggcaggaac ccatcctcac catcatcact ctggaatact    720

ccaatggtaa tccgctggga cacaacagtt tcgaggtgca tatttgtacc tgtcctggga    780

gacacagatg tacagaggaa gacaatttcc agaagaagtg ggagccttgc cctgagccac    840

cctctgggag gatcactaag caaacactgc ccaccagcac cagctcctct atcaagccaa    900

agaagaagcc actggatgaa aaatacttca cccttcagat ccatgggcat gaatgtttca    960

agatgttcct aaagctcaac gaggccttgg agctgaagga tgcccaggct gggaagcaac   1020

caggggggag cagggctcaa tccagccttc ccaagtctaa gaaaaggcaa tctatctccc   1080

accataaaaa aataatgttc aagagagagc agcctgactc agactga                 1127
```

<210> SEQ ID NO 61
<211> LENGTH: 365
<212> TYPE: PRT
<213> ORGANISM: Loxodonta africana

<400> SEQUENCE: 61

```
Val Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Ser Leu Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Gly Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Cys Asp Tyr Ser Asp Cys Leu Asp Pro Pro Gln
                165                 170                 175

His Leu Ile Gln Glu Glu Thr Cys Met Leu Ser Ile Trp Arg Thr Pro
```

```
            180                 185                 190

Ser Leu Tyr Asp Ile Val Trp Gly Ala Leu Gly Ala Thr Arg Gly Arg
        195                 200                 205

Phe Leu Pro Pro Ser Thr Ser Thr Ser Cys Val Thr Ala Pro Ala Trp
    210                 215                 220

Gly Ala Gly Thr His Pro His His His His Ser Gly Ile Leu Gln Trp
225                 230                 235                 240

Ser Ala Gly Thr Gln Gln Phe Arg Gly Ala Tyr Leu Tyr Leu Ser Trp
                245                 250                 255

Glu Thr Gln Met Tyr Arg Gly Arg Gln Phe Pro Glu Glu Val Gly Ala
            260                 265                 270

Leu Pro Ala Thr Leu Trp Glu Asp His Ala Asn Thr Ala His Gln His
        275                 280                 285

Gln Leu Leu Tyr Gln Ala Lys Glu Glu Ala Thr Gly Lys Ile Leu His
    290                 295                 300

Pro Ser Asp Pro Trp Ala Met Phe Gln Asp Val Pro Lys Ala Gln Arg
305                 310                 315                 320

Gly Leu Gly Ala Glu Gly Cys Pro Gly Trp Glu Ala Thr Arg Gly Glu
                325                 330                 335

Gln Gly Ser Ile Gln Pro Ser Gln Val Glu Lys Ala Ile Tyr Leu Pro
            340                 345                 350

Pro Lys Asn Asn Val Gln Glu Arg Ala Ala Leu Arg Leu
        355                 360                 365


<210> SEQ ID NO 62
<211> LENGTH: 1126
<212> TYPE: DNA
<213> ORGANISM: Loxodonta africana

<400> SEQUENCE: 62

aatggaggag cctcagtcag atctcagcac tgagctccct ctgagtcaag ggacgttttc     60

atacttgggg aaactccttc ctgagaagct ggttctgtcc ctctcactgt ccccagcagc    120

agaggcagta gacgatctgt tactcccaga agatgctgca gactggctag aaagccaagc    180

tggggctcaa ggagtatcag aagcccctac actagccacc tcctggacgt tgtcatcctc    240

tgtcccttct cagaagacct acccagcacc tatcgtttct gtctgggctt cttgcattct    300

gggacagcca agtctgtcac ctacacgtac tccctgaact taacatgctg ttttgccggc    360

tggcaaaggc ctgtccagtg cagctgtggg tcacctcaac acccccgccc agcacctgtg    420

ttcacaccat ggccatctac cagacgtcag catatgatgg aggtcgtgaa gcactgcccc    480

caccttgagt gccgctgtga ctatagcgat tgcttggacc ctcctcagca cctcatgcag    540

tgggaggaaa cctgcatgct gagtatttgg aggacaccat cactctatga catagtgtgg    600

ggtgccctag gagccaccag aggtcggttc tgactaccac catccacttc aacttcatgt    660

gtaacagctc ctgcatgggg agcatgaacc catcctcacc atcatcacac tggaagactc    720

caatggtaat ctgctgggac acaacacttt tgaggtgcat atttgtacct gtcccgggag    780

acacagatgt acagaggaag acaatttcca caacaagtgg gagccttgcc ctgagccacc    840

ctctgggagg atcactaagc aaacactgcc caccagcacc agctcctcta ccaagccaaa    900

gaagaagcca ctggatgaaa aatacttcac tcttcagatc catggccatg aatgcttcaa    960

gatgttccta aagctcaacg aggccttgga gttgaaggat gcccaggctg ggaagcagcc   1020

agaggggaac agggctcaat ccagccttcc caagtctaag aaaaggcaat ctacctccca   1080
```

ccataaaaaa ctaacgttca agagagagca gcctgactca gactga 1126

<210> SEQ ID NO 63
<211> LENGTH: 366
<212> TYPE: PRT
<213> ORGANISM: Loxodonta africana

<400> SEQUENCE: 63

Met Glu Glu Pro Gln Ser Asp Leu Ser Thr Glu Leu Pro Leu Ser Gln
1 5 10 15

Gly Thr Phe Ser Tyr Leu Gly Lys Leu Leu Pro Glu Lys Leu Val Leu
20 25 30

Ser Leu Ser Leu Ser Pro Ala Ala Glu Ala Val Asp Asp Leu Leu Leu
35 40 45

Pro Glu Asp Ala Ala Asp Trp Leu Glu Ser Gln Ala Gly Ala Gln Gly
50 55 60

Val Ser Glu Ala Pro Thr Leu Ala Thr Ser Trp Thr Leu Ser Ser Ser
65 70 75 80

Val Pro Ser Gln Lys Thr Tyr Pro Ala Pro Ile Val Ser Val Trp Ala
85 90 95

Ser Cys Ile Leu Gly Gln Pro Ser Leu Ser Pro Thr Arg Thr Pro Thr
100 105 110

His Ala Val Leu Pro Ala Gly Lys Gly Leu Ser Ser Ala Ala Val Gly
115 120 125

His Leu Asn Thr Pro Ala Gln His Leu Cys Ser His His Gly His Leu
130 135 140

Pro Asp Val Ser Ile Trp Arg Ser Ser Thr Ala Pro Thr Leu Ser Ala
145 150 155 160

Ala Val Thr Ile Ala Ile Ala Trp Thr Leu Leu Ser Thr Ser Cys Ser
165 170 175

Gly Arg Lys Pro Ala Cys Val Phe Gly Gly His His His Ser Met Thr
180 185 190

Cys Gly Val Pro Glu Pro Pro Glu Val Gly Ser Asp Tyr His His Pro
195 200 205

Leu Gln Leu His Val Gln Leu Leu His Gly Glu His Glu Pro Ile Leu
210 215 220

Thr Ile Ile Thr Leu Glu Asp Ser Asn Gly Asn Leu Leu Gly His Asn
225 230 235 240

Thr Phe Glu Val His Ile Cys Thr Cys Pro Gly Arg His Arg Cys Thr
245 250 255

Glu Glu Asp Asn Phe His Asn Lys Trp Glu Pro Cys Pro Glu Pro Pro
260 265 270

Ser Gly Arg Ile Thr Lys Gln Thr Leu Pro Thr Ser Thr Ser Ser Ser
275 280 285

Thr Lys Pro Lys Lys Lys Pro Leu Asp Glu Lys Tyr Phe Thr Leu Gln
290 295 300

Ile His Gly His Glu Cys Phe Lys Met Phe Leu Lys Leu Asn Glu Ala
305 310 315 320

Leu Glu Leu Lys Asp Ala Gln Ala Gly Lys Gln Pro Glu Gly Asn Arg
325 330 335

Ala Gln Ser Ser Leu Pro Lys Ser Lys Lys Arg Gln Ser Thr Ser His
340 345 350

His Lys Lys Leu Thr Phe Lys Arg Glu Gln Pro Asp Ser Asp
355 360 365

<210> SEQ ID NO 64
<211> LENGTH: 1126
<212> TYPE: DNA
<213> ORGANISM: Loxodonta africana

<400> SEQUENCE: 64

```
atggaagagc ctcagtcaga tctcagcact gagctccctc tgagtcaagg gacgttttca      60
tacttgggga aactccttcc tgagaagctg gttctgtccc tctcactgtc cccagcagca     120
gaggcaatag acgatctact actcccagaa gatgctgcag actggctaga aagccaagct     180
ggggctcaag gagtatcaga agcccctaca ctagccacct cctggacgtt gtcatcctct     240
gtcccttctc agaagaccta cccagcacct atcgtttctg tctgggcttc ttgcattctg     300
ggacagccaa gtctgtcacc tacacgtact ccctgaactt aacatgctgt tttgccagct     360
ggcaaaggcc tgtccagtgc agctgtgggt cacctcaaca cccccgccaa gcacctgtgt     420
tcacaccatg gccatctacc agacgtcagc atatgatgga ggtcgtgaag cactgccccc     480
accttgagtg ccgctctgac tatagcgatt gcttggaccc tcctcagcac ctcatccagt     540
gggaggaaac ctgcatgctg agtatttgga ggacaccatc actctatgac atagcgtggg     600
gtgccctatg agccaccaga ggtcggttct gactaccacc atccacttca acctcatgtg     660
taacagctcc tgcatggggg gcaggaagcc atcctcacca tcatcacact ggaagactcc     720
aatggtaatc cgctgggaca caacagtttc gaggtgcata tttgtacttg tcctgggaga     780
cacagatgta cagaggaaga caatttccat aagaagtggg agccttgccc tgagccaggc     840
tcggggagga tcactaagcg aacactgccc accagcacca gctcctctat caagccaaag     900
aagaagccac tggatgaaaa atacttcact cttcagatcc atggccatga atgcttcaag     960
atgttcctaa agctcaacga ggccttggag ctgaaggatg cccaggctgg gaagcagcca    1020
gaggggagca gggctcaatc cagccttccc aagtctaaga aaaggcaatc tacctcccgc    1080
cataaaaaac ttatgttcaa gagagagcag cctgactcag actgat                  1126
```

<210> SEQ ID NO 65
<211> LENGTH: 367
<212> TYPE: PRT
<213> ORGANISM: Loxodonta africana

<400> SEQUENCE: 65

```
Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Ser Leu Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Val Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Leu Ser Pro Thr Arg Thr Pro Thr
            100                 105                 110

His Ala Val Leu Pro Ala Gly Lys Gly Leu Ser Ser Ala Ala Val Gly
        115                 120                 125

His Leu Asn Thr Pro Ala Lys His Leu Cys Ser His His Gly His Leu
```

```
    130                 135                 140

Pro Asp Val Ser Ile Trp Arg Ser Ser Thr Ala Pro Thr Leu Ser Ala
145                 150                 155                 160

Ala Leu Thr Ile Ala Ile Ala Trp Thr Leu Leu Ser Thr Ser Ser Ser
                165                 170                 175

Gly Arg Lys Pro Ala Cys Val Phe Gly Gly His His His Ser Met Thr
            180                 185                 190

Arg Gly Val Pro Tyr Glu Pro Pro Glu Val Gly Ser Asp Tyr His His
        195                 200                 205

Pro Leu Gln Pro His Val Gln Leu Leu His Gly Gly Gln Glu Ala Ile
    210                 215                 220

Leu Thr Ile Ile Thr Leu Glu Asp Ser Asn Gly Asn Pro Leu Gly His
225                 230                 235                 240

Asn Ser Phe Glu Val His Ile Cys Thr Cys Pro Gly Arg His Arg Cys
                245                 250                 255

Thr Glu Glu Asp Asn Phe His Lys Lys Trp Glu Pro Cys Pro Glu Pro
            260                 265                 270

Gly Ser Gly Arg Ile Thr Lys Arg Thr Leu Pro Thr Ser Thr Ser Ser
        275                 280                 285

Ser Ile Lys Pro Lys Lys Lys Pro Leu Asp Glu Lys Tyr Phe Thr Leu
    290                 295                 300

Gln Ile His Gly His Glu Cys Phe Lys Met Phe Leu Lys Leu Asn Glu
305                 310                 315                 320

Ala Leu Glu Leu Lys Asp Ala Gln Ala Gly Lys Gln Pro Glu Gly Ser
                325                 330                 335

Arg Ala Gln Ser Ser Leu Pro Lys Ser Lys Lys Arg Gln Ser Thr Ser
            340                 345                 350

Arg His Lys Lys Leu Met Phe Lys Arg Glu Gln Pro Asp Ser Asp
        355                 360                 365
```

<210> SEQ ID NO 66
<211> LENGTH: 1129
<212> TYPE: DNA
<213> ORGANISM: Loxodonta africana

<400> SEQUENCE: 66

```
aatggagaag cccaagtcag atctcagtac tgagctccct ctgagtcaag agactttttc     60

atacttgggg aaactccttc ctgagaagct ggttctgtcc ccctcactgt ccccagcagc    120

ggaggcagta gacgatctgc tgctcccagg agatgctgca gactgcctag aaagccaagc    180

tggggctcaa ggaatatcag cagcccctgc accagccacc ctgacaccag ccacctcctg    240

gacactctca ttctctgtcc cttcccagaa gacctactgc agtaactgtg gtttccgtct    300

tggcttcctg cattctggga cagccaagtc tgtcacctgc atgtactccc ctggccttaa    360

caagctgttt tgccagctgg caaagacctg tccagtgcag ccgtagctca gctcaccacc    420

ccaccccagc acctgtgttc acaccatggc catctaccag acgtcagcat atgacagagg    480

tcgtgcagca ctgcccccac cttgagtgct gctccgacta tagcgatggc ctggccgctc    540

ctcagcatct tatccaggtg ggaggaatcc tgcgtgctga tatttgtagg acaccatcac    600

tcttcgacat agtgtggggt accgtatgag ctacctcagg tcggttctga ctaccaccat    660

ccacttcaac ttcatgtgta gcagctcctg catggcgggg ggaacccatc ctcaccatca    720

tcacactgga agactccgat ggtaatctgc taggacacaa cagttttgag gtgcatattt    780

gtactgttct gggagagaca gacgtacaga ggaagaaaat ttccacaaca agtgggagcc    840
```

```
accctctgag aggatcacta agtaagcact gcacaccagc accagctcct ctaccgagcc    900

aaagaagaag ccagtggatg aaaaatattt caccccttaag atccgtgggc atgaatgctt    960

caagatgttc ctagagttga atgaggcatt ggagctgaag gatgcccagg ctgggaagca   1020

gccagagggg agcagggctc aatgcagcct tccaaactct aagaaagggg aatctaccac   1080

ccactgtaaa aaactaatgt tcaagagaga ggggcctgac tcagactga               1129


<210> SEQ ID NO 67
<211> LENGTH: 367
<212> TYPE: PRT
<213> ORGANISM: Loxodonta africana

<400> SEQUENCE: 67

Met Glu Lys Pro Lys Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Gly Asp Ala Ala Asp Cys Leu Glu Ser Gln Ala Gly Ala Gln Gly
    50                  55                  60

Ile Ser Ala Ala Pro Ala Pro Ala Thr Leu Thr Pro Ala Thr Ser Trp
65                  70                  75                  80

Thr Leu Ser Phe Ser Val Pro Ser Gln Lys Thr Tyr Cys Ser Asn Cys
                85                  90                  95

Gly Phe Arg Leu Gly Phe Leu His Ser Gly Thr Ala Lys Ser Val Thr
            100                 105                 110

Cys Met Tyr Ser Pro Gly Leu Asn Lys Leu Phe Cys Gln Leu Ala Lys
        115                 120                 125

Thr Cys Pro Val Gln Pro Leu Ser Ser Pro Pro His Pro Ser Thr Cys
    130                 135                 140

Val His Thr Met Ala Ile Tyr Gln Thr Ser Ala Tyr Asp Arg Gly Arg
145                 150                 155                 160

Ala Ala Leu Pro Pro Pro Val Leu Leu Arg Leu Arg Trp Pro Gly Arg
                165                 170                 175

Ser Ser Ala Ser Tyr Pro Gly Gly Arg Asn Pro Ala Cys Tyr Leu Asp
            180                 185                 190

Thr Ile Thr Leu Arg His Ser Val Gly Tyr Arg Met Ser Tyr Leu Arg
        195                 200                 205

Ser Val Leu Thr Thr Thr Ile His Phe Asn Phe Met Cys Ser Ser Ser
    210                 215                 220

Cys Met Ala Gly Gly Thr His Pro His His His His Thr Gly Arg Leu
225                 230                 235                 240

Arg Trp Ser Ala Arg Thr Gln Gln Phe Gly Ala Tyr Leu Tyr Cys Ser
                245                 250                 255

Gly Arg Asp Arg Arg Thr Glu Glu Glu Asn Phe His Asn Lys Trp Glu
            260                 265                 270

Pro Pro Ser Glu Arg Ile Thr Lys Ala Leu His Thr Ser Thr Ser Ser
        275                 280                 285

Ser Thr Glu Pro Lys Lys Lys Pro Val Asp Glu Lys Tyr Phe Thr Leu
    290                 295                 300

Lys Ile Arg Gly His Glu Cys Phe Lys Met Phe Leu Glu Leu Asn Glu
305                 310                 315                 320
```

```
Ala Leu Glu Leu Lys Asp Ala Gln Ala Gly Lys Gln Pro Glu Gly Ser
                325                 330                 335

Arg Ala Gln Cys Ser Leu Pro Asn Ser Lys Lys Gly Glu Ser Thr Thr
            340                 345                 350

His Cys Lys Lys Leu Met Phe Lys Arg Glu Gly Pro Asp Ser Asp
        355                 360                 365


<210> SEQ ID NO 68
<211> LENGTH: 1126
<212> TYPE: DNA
<213> ORGANISM: Loxodonta africana

<400> SEQUENCE: 68

atggaggagg ctcagtcaga tctcagcact gagctccctc tgagtcaaga gacgttttca      60

tacttgggga aactccttcc tgagaagctg gttctgttcc cctcactgtc cccagcagca     120

gaggcagtag acgatctgct actcccagaa gatgctgcag actggctaga aagccaagct     180

ggggctcaag gaatatcaga agcccctacg ctagccacct cctggacgct gtcatcctct     240

gtcccttctc agaagaccta cccagcacct atcacttctg tctgggcttc ttgcattctg     300

ggacagccaa gtctgtcacc tacacgtact cccctgaact taacgtgctg ttttgccagc     360

tggcaaaggc ctgtccagtg cagctgtggg tcacctcaac acccccgccc agcacctgtg     420

ttcacaccat ggccatctac cagatgtcag catatgatgg aggtcgtgca gcactgtccc     480

caccttgagt gccgctctga ctatagcgat tgcttagacc ctcctcagca ccttatccag     540

tgggaggaaa cctgcatgct gagtatttgg aggacaccat cactctatga catagtgtgg     600

ggtgccctag gagccaccag aggtcggttc tgactaccac catccacttc aacttcatgt     660

gtaacagctc ctgcatgggg ggcaggaacc catcctcacc atcatcacac tggaagactc     720

caatggtaat ccgctgggac acaacagttt cgaggtgcat atttgtactt gtcctgggag     780

acacagatgt acagaggaag acaatttcca taagaagtgg gagccttgcc ctgagccagg     840

ctcggggagg atcactaagg aacactgccc accagcacca gctcctctac caagccaaag     900

aagaagccac tggatgaaaa atacttcact cttcagatcc atggccatga atgcttcaag     960

atgttcctaa agctcaacga ggccttggag ctcaaggatg cccaggctgg gaagcagcca    1020

gaggggaaca gggctcaatc cagccttccc aagtctaaga aaaggcaatc tacctcccgc    1080

cataaaaaac ttatgttcaa gagagagcag cctgactcag actgat                   1126


<210> SEQ ID NO 69
<211> LENGTH: 369
<212> TYPE: PRT
<213> ORGANISM: Loxodonta africana

<400> SEQUENCE: 69

Met Glu Glu Ala Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Phe Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Thr Ser Val Trp Ala
```

```
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Arg Pro Ala Pro Val Phe Thr Pro Trp
    130                 135                 140

Pro Ser Thr Arg Cys Gln His Met Met Glu Val Val Gln His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Thr His Pro His His His His Thr Gly Arg Leu Gln
225                 230                 235                 240

Trp Ser Ala Gly Thr Gln Gln Phe Arg Gly Ala Tyr Leu Tyr Leu Ser
                245                 250                 255

Trp Glu Thr Gln Met Tyr Arg Gly Arg Gln Phe Pro Glu Val Gly Ala
            260                 265                 270

Leu Pro Ala Arg Leu Gly Glu Asp His Gly Thr Leu Pro Thr Ser Thr
        275                 280                 285

Ser Ser Ser Thr Lys Pro Lys Lys Lys Pro Leu Asp Glu Lys Tyr Phe
    290                 295                 300

Thr Leu Gln Ile His Gly His Glu Cys Phe Lys Met Phe Leu Lys Leu
305                 310                 315                 320

Asn Glu Ala Leu Glu Leu Lys Asp Ala Gln Ala Gly Lys Gln Pro Glu
                325                 330                 335

Gly Asn Arg Ala Gln Ser Ser Leu Pro Lys Ser Lys Lys Arg Gln Ser
            340                 345                 350

Thr Ser Arg His Lys Lys Leu Met Phe Lys Arg Glu Gln Pro Asp Ser
        355                 360                 365

Asp


<210> SEQ ID NO 70
<211> LENGTH: 1154
<212> TYPE: DNA
<213> ORGANISM: Loxodonta africana

<400> SEQUENCE: 70

aatggaggag ccccagtcag atctcagcac tgagctccct ctgagtcaag agaccttttc      60

atacttgggg aaactccttc ctgagaagct ggttctgtcc ccaccactgt ccccagcagt     120

ggaggtagca gacgatctgc tactcccaga agatgctgca gactggctag aaagccaagc     180

tggggctcaa ggaatatcag tagcccctgc accagcctct cctgagccag ccacctcctg     240

gacactgtca tcctctgtcc cttctcagaa gacctacccc agcatctatg gtttccatct     300

gggcttcttg cattctggga cagccaagtc catcacctac atgtactccc ctgaccttaa     360

caagctgttt tgacagctag caaagacctg tccagtgcag ccgtgggtca cctcaccaac     420

cctgcccagc acctgtgttc acaccatggc catttaccat aagtcagcat atgacggcgg     480
```

```
ttgtgcagca ctgcccccac cttgggcgct gctctgacta tagcgatggc ctcgtccctc    540

ctcagcacct catccagcgg ggagaaaacc tgcgtgctga gtatttggag gacactatca    600

ctctttgaca tagtgtgggg tgccctatga gccaccagag gtcggtgccc tatgagccac    660

cagaggtcgg ttctgactac caccatccac ttcatgtgta acagctcctg cagcaaccca    720

tcctcaccat catcacactg gaagactcca atggtaatct gctgggatgc aacaggttcg    780

aggtgcatat ttgtacctgt cctgggagag gcagatgtat agaggaagac aatttccaca    840

tgaagtggga gccttgcccc gagctaccct ctgggaggat cactaagcga gtgctgccca    900

ccagcaccag ctcctctacc aagccaaaga agccgccact ggatgaaaga tatttcaccc    960

ttcagatccg tggacatgaa tgctacaaga tgttctagag ctgaatgcgg ccttggagct   1020

gaaggatgcc gaggctggga agcagccaga ggggagcagg gctcaattca gccttcccaa   1080

gccttagaaa gggcaatcta cctcccacca taaaaaaaca aacattcaag agagaagggc   1140

ctgactcaga ctaa                                                     1154


<210> SEQ ID NO 71
<211> LENGTH: 371
<212> TYPE: PRT
<213> ORGANISM: Loxodonta africana

<400> SEQUENCE: 71

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Pro Leu Ser Pro Ala Val Glu Val Ala Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Val Ala Pro Ala Pro Ala Ser Pro Glu Pro Ala Thr Ser Trp
65                  70                  75                  80

Thr Leu Ser Ser Ser Val Pro Ser Gln Lys Thr Tyr Pro Ser Ile Tyr
                85                  90                  95

Gly Phe His Leu Gly Phe Leu His Ser Gly Thr Ala Lys Ser Ile Thr
            100                 105                 110

Tyr Met Tyr Ser Pro Asp Leu Asn Lys Leu Phe Gln Leu Ala Lys Thr
        115                 120                 125

Cys Pro Val Gln Pro Trp Val Thr Ser Pro Thr Leu Pro Ser Thr Cys
    130                 135                 140

Val His Thr Met Ala Ile Tyr His Lys Ser Ala Tyr Asp Gly Gly Cys
145                 150                 155                 160

Ala Ala Leu Pro Pro Pro Trp Ala Leu Leu Leu Arg Trp Pro Arg Pro
                165                 170                 175

Ser Ser Ala Pro His Pro Ala Gly Arg Lys Pro Ala Cys Val Phe Gly
            180                 185                 190

Gly His Tyr His Ser Leu Thr Cys Gly Val Pro Tyr Glu Pro Pro Glu
        195                 200                 205

Val Gly Ala Leu Ala Thr Arg Gly Arg Phe Leu Pro Pro Ser Thr Ser
    210                 215                 220

Cys Val Thr Ala Pro Ala Ala Thr His Pro His His His His Thr Gly
225                 230                 235                 240

Arg Leu Gln Trp Ser Ala Gly Met Gln Gln Val Arg Gly Ala Tyr Leu
                245                 250                 255
```

```
Tyr Leu Ser Trp Glu Arg Gln Met Tyr Arg Gly Arg Gln Phe Pro His
            260                 265                 270

Glu Val Gly Ala Leu Pro Arg Ala Thr Leu Trp Glu Asp His Ala Ser
        275                 280                 285

Ala Ala His Gln His Gln Leu Leu Tyr Gln Ala Lys Glu Ala Ala Thr
    290                 295                 300

Gly Lys Ile Phe His Pro Ser Asp Pro Trp Thr Met Leu Gln Asp Val
305                 310                 315                 320

Leu Glu Leu Asn Ala Ala Leu Glu Leu Lys Asp Ala Glu Ala Gly Lys
                325                 330                 335

Gln Pro Glu Gly Ser Arg Ala Gln Phe Ser Leu Pro Lys Pro Lys Gly
            340                 345                 350

Gln Ser Thr Ser His His Lys Lys Thr Asn Ile Gln Glu Arg Arg Ala
        355                 360                 365

Leu Arg Leu
    370


<210> SEQ ID NO 72
<211> LENGTH: 1127
<212> TYPE: DNA
<213> ORGANISM: Loxodonta africana

<400> SEQUENCE: 72

agtggaggag cctcagtcag atctgagcat tgagctccct ctgagtcaag agacattttc     60

atacttgggg aaactccttt ctgagaagct ggttctatcc ccctcactgt ccccagcagc    120

ggaggcagta gtcaatctgc tactcccaga agatgctgca gactggctag aaagccaagg    180

tggggctcaa ggaatatcag aagcacctac actagccacc tcctggacgc tgtcatcctc    240

tgttccttct cagaagacct acccagcacc tatcatttct gtctgggctt cttgcattct    300

gggacagcca agtccgtcac ctacacgtac tcccctgaac ttaacatgct gttttgccag    360

ctggcaaagg cctgtccagt gcagccgtgg gtcacctcaa cacccccgcc cagcacctgt    420

gttcacacca tggccatcta ccagacgtca gcatatgatg gaggtcgtga agcactgccc    480

ccaccttgag tgccgctctg actatagcga ttgcttggac cctcctcagc acctcatgca    540

gtgggaggaa acctgcatgc tgagtatttg gaggacacca tcactctatg acatagtgtg    600

gggtgcccta ggagccacca gaggtcggtt ctgactacca ccatccactt caacttcatg    660

tgtaacagct cctgcatggg gcgcatgaac ccattctcac cattatgaca atggaagact    720

ccaatggtaa tccgctggga cacaacagtt tcgaggtgca tatttgtacc tgtcctggga    780

gacacagatg tacagaggaa gacaatttcc acaacaagtg ggagccttgc cctgagccac    840

cctctgggag gatcactacg caaacactgc ccaccagcac cagctcctct acgaagccaa    900

agaagaagcc actggatgaa aaatacttca cccttcagat ccatgggcat gaatgcttca    960

agatgttcct aaagctcaac gaggccttgg agctgaagga tgcccaggct gggaagcagc   1020

cagaggggaa cagggctcaa tccagccttc ccaagtctaa gaaaaggcaa tctacctccc   1080

accataaaaa actaacgttc aagagagagc agcctgactc agactga                 1127


<210> SEQ ID NO 73
<211> LENGTH: 366
<212> TYPE: PRT
<213> ORGANISM: Loxodonta africana

<400> SEQUENCE: 73
```

```
Val Glu Glu Pro Gln Ser Asp Leu Ser Ile Glu Leu Pro Leu Ser Gln
1               5                   10                  15

Glu Thr Phe Ser Tyr Leu Gly Lys Leu Leu Ser Glu Lys Leu Val Leu
            20                  25                  30

Ser Pro Ser Leu Ser Pro Ala Ala Glu Ala Val Val Asn Leu Leu Leu
        35                  40                  45

Pro Glu Asp Ala Ala Asp Trp Leu Glu Ser Gln Gly Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Ile Ser Val Trp Ala
                85                  90                  95

Ser Cys Ile Leu Gly Gln Pro Ser Pro Ser Pro Thr Arg Thr Pro Leu
            100                 105                 110

Asn Leu Thr Cys Cys Phe Ala Ser Trp Gln Arg Pro Val Gln Cys Ser
        115                 120                 125

Arg Gly Ser Pro Gln His Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Met Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Thr His Ser His His Tyr Asp Asn Gly Arg Leu Gln Trp
225                 230                 235                 240

Ser Ala Gly Thr Gln Gln Phe Arg Gly Ala Tyr Leu Tyr Leu Ser Trp
                245                 250                 255

Glu Thr Gln Met Tyr Arg Gly Arg Gln Phe Pro Gln Gln Val Gly Ala
            260                 265                 270

Leu Pro Ala Thr Leu Trp Glu Asp His Tyr Ala Asn Thr Ala His Gln
        275                 280                 285

His Gln Leu Leu Tyr Glu Ala Lys Glu Glu Ala Thr Gly Lys Ile Leu
    290                 295                 300

His Pro Ser Asp Pro Trp Ala Met Leu Gln Asp Val Pro Lys Ala Gln
305                 310                 315                 320

Arg Gly Leu Gly Ala Glu Gly Cys Pro Gly Trp Glu Ala Ala Arg Gly
                325                 330                 335

Glu Gln Gly Ser Ile Gln Pro Ser Gln Val Glu Lys Ala Ile Tyr Leu
            340                 345                 350

Pro Pro Lys Thr Asn Val Gln Glu Arg Ala Ala Leu Arg Leu
        355                 360                 365
```

<210> SEQ ID NO 74
<211> LENGTH: 1127
<212> TYPE: DNA
<213> ORGANISM: Loxodonta africana

<400> SEQUENCE: 74

```
aatggaggag cctcagtcag atctcagcac tgagctccct ctgagtcaag agacattttc     60
```

```
atacttgggg aaactccttc ctgagaagct ggttctgtcc ccctcactgt ccccagcagc    120

ggaggcagta gatgatctgc tactcccaga agatgctgca gactggctag aaagccaagc    180

tggggctcaa ggaatatcag aagcccctac actagccacc tcctggacgc tgtcatcctc    240

tgtcccttct cagaagacct acccagcacc tatcgtttct gtctgggctt cttgcattct    300

gggacagcca agtctgtcac ctacacgtac tcccctgaac ttaacatgct gttttgccgg    360

ctggcaaagg cctgtccagt gcagctgtgg gtcacctcaa caaccccgcc cagcacctgt    420

gttcacacca tggccatcta ccagacgtca gcatatgatg gaggtcgtga agcactgccc    480

ccaccttgag tgccgctgtg actatagcga ttgcttggac cctcctcagc acctcatcca    540

gtaggaggaa acctgcatgc tgagtatttg gaggacacca tcactctatg acatagtgtg    600

gggtgcccta ggagccacca gaggtcggtt ctgactacca ccatccactt caacttcatg    660

tgtaacagct cctgcatggg gggcatgaac ccatcctcac catcatcact ctggaatact    720

ccaatggtaa tccgctggga cacaacagtt tcgaggtgca tatttgtacc tgtcctggga    780

gacacagatg tacagaggaa gacaatttcc agaagaagtg ggagccttgc cctgagccac    840

cctctgggag gatcactaag caaacactgc ccaccagcac cagctcctct atcaagccaa    900

agaagaagcc actggatgaa aaatacttca cccttcagat ccatggccat gaatgtttca    960

agatgttcct aaagctcaac gaggccttgg agctgaagga tgcccaggct gggaagcaac   1020

caggggggag cagggctcaa tccagccttc ccaagtctaa gaaaaggcaa tctatctccc   1080

accataaaaa actaatgttc aagaaagagc agcctgactc agactga                 1127


<210> SEQ ID NO 75
<211> LENGTH: 364
<212> TYPE: PRT
<213> ORGANISM: Loxodonta africana

<400> SEQUENCE: 75

Met Glu Glu Pro Gln Ser Asp Leu Ser Thr Glu Leu Pro Leu Ser Gln
1               5                   10                  15

Glu Thr Phe Ser Tyr Leu Gly Lys Leu Leu Pro Glu Lys Leu Val Leu
            20                  25                  30

Ser Pro Ser Leu Ser Pro Ala Ala Glu Ala Val Asp Asp Leu Leu Leu
        35                  40                  45

Pro Glu Asp Ala Ala Asp Trp Leu Glu Ser Gln Ala Gly Ala Gln Gly
    50                  55                  60

Ile Ser Glu Ala Pro Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Leu Ser Pro Thr Arg Thr Pro Leu
            100                 105                 110

Asn Leu Thr Cys Cys Phe Ala Gly Trp Gln Arg Pro Val Gln Cys Ser
        115                 120                 125

Cys Gly Ser Pro Gln Gln Pro Arg Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Cys Asp Tyr Ser Asp Cys Leu Asp Pro Pro Gln
                165                 170                 175

His Leu Ile Gln Glu Glu Thr Cys Met Leu Ser Ile Trp Arg Thr Pro
            180                 185                 190
```

```
Ser Leu Tyr Asp Ile Val Trp Gly Ala Leu Gly Ala Thr Arg Gly Arg
        195                 200                 205

Phe Leu Pro Pro Ser Thr Ser Thr Ser Cys Val Thr Ala Pro Ala Trp
    210                 215                 220

Gly Ala Thr His Pro His His His His Ser Gly Ile Leu Gln Trp Ser
225                 230                 235                 240

Ala Gly Thr Gln Gln Phe Arg Gly Ala Tyr Leu Tyr Leu Ser Trp Glu
                245                 250                 255

Thr Gln Met Tyr Arg Gly Arg Gln Phe Pro Glu Glu Val Gly Ala Leu
            260                 265                 270

Pro Ala Thr Leu Trp Glu Asp His Ala Asn Thr Ala His Gln His Gln
        275                 280                 285

Leu Leu Tyr Gln Ala Lys Glu Glu Ala Thr Gly Lys Ile Leu His Pro
    290                 295                 300

Ser Asp Pro Trp Pro Met Phe Gln Asp Val Pro Lys Ala Gln Arg Gly
305                 310                 315                 320

Leu Gly Ala Glu Gly Cys Pro Gly Trp Glu Ala Thr Arg Gly Glu Gln
                325                 330                 335

Gly Ser Ile Gln Pro Ser Gln Val Glu Lys Ala Ile Tyr Leu Pro Pro
            340                 345                 350

Lys Thr Asn Val Gln Glu Arg Ala Ala Leu Arg Leu
        355                 360


<210> SEQ ID NO 76
<211> LENGTH: 1127
<212> TYPE: DNA
<213> ORGANISM: Loxodonta africana

<400> SEQUENCE: 76

aatggaggag cctcagtcag atctcagcac tgagctccct ctgagtcaag ggacgttttc      60

atacttgggg aaactccttc ctgagaagct ggttctgttc ccctcactgt ccccagcagc     120

agaggcaata gacgatctgc tactcccaga agatgctgca gactggctag aaagccaagc     180

tggggctcaa ggactatcag aagcctctac actagccacc tcctggacgc tgtcatcctc     240

tgtcccttct cagaagacct acccagcacc tatcgtttct gtctgggctt cttgcattct     300

gggacagcca agttcgtcac ctacacgtac tcccctgaac ttaacatgct gttttgccag     360

ctggcaaagg cctgtccagt gcagctgtgg gtcacctcaa cacccctgcc cagcacctgt     420

gttcacacca tggccatcta ccagacgtca gcatatgatg gaggtcgtga agcactgccc     480

ccaccttgag tgccgctctg actatagcga ttgcttggac cctcctcagc acctcatcca     540

gtgggaggaa acctgcatgc tgagtatttg gaggacacca tcactctatg acatagtgtg     600

gggtgcccta ggagccacca gaggtcggtt ctgactacca ccatccactt caacttcatg     660

tgtaacagct cctgcatggg gggcaggaag ccatcctcac catcatcaca ctggaaaact     720

ccaatggtaa tccgctgaga cacaacagtt tcgaggtgca tatttgtact tgtcctggga     780

gacacagata tacagaggaa gacaatttcc ataagaagtg ggagccttgc cctgagccag     840

gctcggggag gatcactaag cgaacactgc ccaccagcac cagctcctct accaagccaa     900

agaagaagcc actggatgaa aaatacttca ctcttcagat ccatggccat gaatgcttca     960

agatgttcct aaagctcaac gaggccttgg agctcaagga tgcccagact gggaagcagc    1020

cagaggggaa cagggctcaa tccagccttc ccaagtctaa gaaaaggcaa tctacctccc    1080

gccataaaaa acttatgttc aagagagagc agcctgactc agactga                  1127
```

<210> SEQ ID NO 77
<211> LENGTH: 365
<212> TYPE: PRT
<213> ORGANISM: Loxodonta africana

<400> SEQUENCE: 77

```
Met Glu Glu Pro Gln Ser Asp Leu Ser Thr Glu Leu Pro Leu Ser Gln
1               5                   10                  15

Gly Thr Phe Ser Tyr Leu Gly Lys Leu Leu Pro Glu Lys Leu Val Leu
            20                  25                  30

Phe Pro Ser Leu Ser Pro Ala Ala Glu Ala Ile Asp Asp Leu Leu Leu
        35                  40                  45

Pro Glu Asp Ala Ala Asp Trp Leu Glu Ser Gln Ala Gly Ala Gln Gly
    50                  55                  60

Leu Ser Glu Ala Ser Thr Leu Ala Thr Ser Trp Thr Leu Ser Ser Ser
65                  70                  75                  80

Val Pro Ser Gln Lys Thr Tyr Pro Ala Pro Ile Val Ser Val Trp Ala
                85                  90                  95

Ser Cys Ile Leu Gly Gln Pro Ser Ser Ser Pro Thr Arg Thr Pro Leu
            100                 105                 110

Asn Leu Thr Cys Cys Phe Ala Ser Trp Gln Arg Pro Val Gln Cys Ser
        115                 120                 125

Cys Gly Ser Pro Gln His Pro Cys Pro Ala Pro Val Phe Thr Pro Trp
    130                 135                 140

Pro Ser Thr Arg Arg Gln His Met Met Glu Val Val Lys His Cys Pro
145                 150                 155                 160

His Leu Glu Cys Arg Ser Asp Tyr Ser Asp Cys Leu Asp Pro Pro Gln
                165                 170                 175

His Leu Ile Gln Trp Glu Glu Thr Cys Met Leu Ser Ile Trp Arg Thr
            180                 185                 190

Pro Ser Leu Tyr Asp Ile Val Trp Gly Ala Leu Gly Ala Thr Arg Gly
        195                 200                 205

Arg Phe Leu Pro Pro Ser Thr Ser Thr Ser Cys Val Thr Ala Pro Ala
    210                 215                 220

Trp Gly Ala Gly Ser His Pro His His His His Thr Gly Lys Leu Gln
225                 230                 235                 240

Trp Ser Ala Glu Thr Gln Gln Phe Arg Gly Ala Tyr Leu Tyr Leu Ser
                245                 250                 255

Trp Glu Thr Gln Ile Tyr Arg Gly Arg Gln Phe Pro Glu Val Gly Ala
            260                 265                 270

Leu Pro Ala Arg Leu Gly Glu Asp His Ala Asn Thr Ala His Gln His
        275                 280                 285

Gln Leu Leu Tyr Gln Ala Lys Glu Glu Ala Thr Gly Lys Ile Leu His
    290                 295                 300

Ser Ser Asp Pro Trp Pro Met Leu Gln Asp Val Pro Lys Ala Gln Arg
305                 310                 315                 320

Gly Leu Gly Ala Gln Gly Cys Pro Asp Trp Glu Ala Ala Arg Gly Glu
                325                 330                 335

Gln Gly Ser Ile Gln Pro Ser Gln Val Glu Lys Ala Ile Tyr Leu Pro
            340                 345                 350

Pro Lys Thr Tyr Val Gln Glu Arg Ala Ala Leu Arg Leu
        355                 360                 365
```